(12) United States Patent
Bromberg et al.

(10) Patent No.: US 7,204,997 B2
(45) Date of Patent: Apr. 17, 2007

(54) RESPONSIVE MICROGEL AND METHODS RELATED THERETO

(75) Inventors: Lev E. Bromberg, Swampscott, MA (US); Marina Temchenko, Swampscott, MA (US)

(73) Assignee: Supratek Pharma Inc., Quebec (CA)

( * ) Notice: Subject to any disclaimer, the term of this patent is extended or adjusted under 35 U.S.C. 154(b) by 447 days.

(21) Appl. No.: 10/298,808

(22) Filed: Nov. 18, 2002

(65) Prior Publication Data

US 2003/0152623 A1    Aug. 14, 2003

Related U.S. Application Data

(60) Provisional application No. 60/352,200, filed on Jan. 29, 2002.

(51) Int. Cl.
*A61K 9/14*     (2006.01)

(52) U.S. Cl. .................. 424/487; 424/486; 424/484; 424/400; 514/772; 514/772.1; 514/772.3; 514/772.4

(58) Field of Classification Search .................. None
See application file for complete search history.

(56) References Cited

U.S. PATENT DOCUMENTS 5,252,318 A    10/1993  Joshi et al.
5,688,855 A *  11/1997  Stoy et al. .................. 524/505
5,939,485 A     8/1999  Bromberg et al.
6,316,011 B1   11/2001  Ron et al.

FOREIGN PATENT DOCUMENTS

WO    WO 97/00275    1/1997

OTHER PUBLICATIONS

Gorelikov, et al., "Hybrid Microgels Photoresponsive in the Near-Infrared Spectral Range" Journal of the American Chemical Society, 2004, p. 15938.*

"Poly(ethylene glycol) Block Copolymers by Atom Transfer Radical Polymerization-Synthesis, Kinetics and Characterization" Journal of Macromolecular Science Part A: Pure and Applied Chemistry vol. 42, No. 4 (2005) 495-508.*

(Continued)

*Primary Examiner*—Michael P. Woodward
*Assistant Examiner*—Eric E. Silverman
(74) *Attorney, Agent, or Firm*—Mathews, Shepherd, McKay & Bruneau, P.A.

(57) ABSTRACT

A responsive microgel is provided which responds volumetrically and reversibly to a change in one or more aqueous conditions selected from the group consisting of (temperature, pH, and ionic conditions) comprised of an ionizable network of covalently cross-linked homopolymeric ionizable monomers wherein the ionizable network is covalently attached to an amphiphilic copolymer to form a plurality of 'dangling chains' and wherein the 'dangling chains' of amphiphilic copolymer form immobile micelle-like aggregates in aqueous solution. A responsive microgel is further provided that comprises at least one therapeutic entity and delivers a substantially linear and sustained release of the therapeutic entity under physiological conditions.

15 Claims, 16 Drawing Sheets

OTHER PUBLICATIONS

Lev Bromberg, "Synthesis & Self-Assembly of Poly(ethylene oxide)-b-poly(propylene oxide)-b-poly(ethylene oxide)-g-poly(acrylic acid) Gels," Ind. Eng. Chem. Res. 2001, 40, 2437-2444.

Lev Bromberg, "Polyether-Modified Poly(acrylic acid): Synthesis & Applications," Ind. Eng. Chem. Res. 1998, 37, 4267-4274.

Lev Bromberg, "Novel Family of Thermogelling Materials via C-C Bonding between Poly(acrylic acid) and Poly(ethylene oxide)-b-poly(propylene oxide)-b-poly(ethylene oxide)," J. Phys. Chem. B 1998, 102, 1956-1963.

Lev Bromberg, "Self-Assembly in Aqueous Solutions of Polyether-Modified Poly(acrylic acid)", Langmuir 1998, 14, 5806-5812.

Lev Bromberg, et al., "Bioactive Surface via Immobilization of Self-Assembling Polymers onto Hydrophobic Materials," Bioconjugate Chem., 1999, 10, 678-686.

Paul D.T. Huibers, et al, "Reversible Gelation in Semidilute Aqueous Solutions of Associative Polymers: A Small-Angle Neutron Scattering Study," Macromolecules, 1999, 32, 4889-4894.

Lev Bromberg, "Scalling of Rheological Properties of Hydrogels from Associating Polymers," Macromolecules, 1998, 31, 6148-6156.

Lev E. Bromberg, et al., "Aggregation Phenomena in Aqueous Solutions of Hydrophobically Modified Polyelectrolytes. A Probe Solubilization Study," Macromolecules 1999, 32, 3649-3657.

Lev Bromberg, " Properties of Aqueous Solutions and Gels of Poly(ethylene oxide)-b-poly(propylene oxide)-b-poly(ethylene oxide)-g-poly(scrylic acid)", J. Phys. Chem. B 198, 102, 10736-10744.

* cited by examiner

A. Structure I

B. Structure II

Structure III

FIG.4

Initiation

R-R ⟶ 2R·

Propagation

R· + nM + qX ⟶ RMMMXMM·
                |
                RMMXMMMM·

Chain transfer via hydrogen abstraction

R· + P-H ⟶ RH + P·

Polymer grafting onto microgel network

RMMMXMMH              RMMMXMMH
    |         + P· ⟶      |
RMMXMMMM·             RMMXMMMM
                             |
                             P

R-R — free-radical intiator

M — vinyl monomer

X — divinyl cross-linker

P-H — polymer

RESPONSIVE MICROGEL AND METHODS RELATED THERETO

CROSS-REFERENCE TO RELATED APPLICATION

This application claims the benefit of U.S. Provisional Application No. 60/352,200, filed on Jan. 29, 2002, and entitled "Useful Responsive Microgel Particulates and Methods Related Thereto," the disclosure of which is hereby incorporated by reference in its entirety.

FIELD OF THE INVENTION

The present invention relates to microgels comprised of an ionizable network covalently attached to an amphiphilic copolymer, which forms aggregates capable of solubilizing drugs in aqueous solution. The responsive microgel reversibly responds volumetrically to factors such as temperature, pH, and ionic conditions. Particularly, the responsive microgel is able to imbibe or solubilize a large amount of therapeutic agent and deliver a substantially linear and sustained release of therapeutic agent under physiological conditions.

BACKGROUND OF THE INVENTION

Volumetric changes (shrinking or swelling) of temperature-sensitive microgel particles dispersed in water is an intraparticle phenomenon, but it is known in the art that also interparticle aggregation takes place during the collapse transition. Very stable polymer dispersions have been synthesized, for instance, using poly(ethylene oxide), PEO, as a stabilizing agent. Ottewill, R. H., et al., Colloid Polym. Sci. 1995, 273, 379.

The most widely studied class of responsive polymers are temperature responsive poly(alkylacrylamides), specifically poly(N-isopropylacrylamide). Shibayama, M., et al., *Advances in Polymer Science*; Springer-Verlag: Berlin, 1993; 109, pp 1–62; Pelton, R. *Adv. Colloid Interface Sci.* 2000, 85, 1–33. However, poly(alkylacrylamides) are perceived to be toxic, especially in biomedical applications. L. E. Bromberg and E. S. Ron, *Adv. Drug Delivery Revs.*, 1998, 31, 197–221. Furthermore, nonionic nature of poly(alkylacrylamides) prevents creating ion-sensitive microgels.

Synthesis of polymers comprised of polyethers such as poly(ethylene oxide), poly(propylene oxide) and their copolymers grafted onto poly(acrylic acid) and other polyelectrolytes such as poly(2-acrylamido-2-methylpropanesulfonic acid), polyethyleneimine and the like are known in the art. See, e.g., Hourdet, D., et al., Polymer (1994), 35(12), 2624–30; L'Alloret, et al., Colloid Polym. Sci. (1995), 273(12), 1163–73; L'alloret, F.; Maroy, P., et al., Revue de l'Institut Francais du Petrole (1997), 52(2), 117–128; Hourdet, D. et al., Macromolecules; 1998; 31(16); 5323–5335; Schlumberger, D. C., EPO Publication 0 583 814 A1, 1993; 0 629 649 A1, 1994; Hoffman, et al., Advanced Biomaterials in Biomedical Engineering and Drug Delivery Systems, Ogata, N., et al., Kim, S. W., Feijen, J., Okano, T., Eds., Springer: Tokyo, 1996; pp 62–66; Hoffman, A. S., et al., Proc. Int. Symp. Controlled Release Bioact. Mater. (1995), 22, 159; Chen, G., et al., Proc. Int. Symp. Controlled Release Bioact. Mater. (1995), 22, 167; Hoffman, A. S.; E. S. Ron, L. E. Bromberg, M. Temchenko, End Modified Thermal Responsive Microgels, U.S. Pat. No. 6,316,011.

These polymers are synthesized by conversion of one or both terminal OH-groups of a polyether into a more active group such as $NH_2$—, $SH$—, followed by grafting of the resulting modified polyether onto the backbone of a chosen polyelectrolyte. Structures that could result from these syntheses may comprise, for example, un-cross-linked PLURONIC® copolymer bonded to poly(acrylic acid). See, e.g., A. S. Hoffman, et al., Advanced Biomaterials in Biomedical Engineering and Drug Delivery Systems, N. Ogata, S. W. Kim, J. Feijen, T. Okano, eds., Springer, Tokyo, 1996, pp. 62–66; A S Hoffman, et al., Polym. Prepr., 38: 524–525, (1997); G. Chen, et al., Poly(ethylene glycol) Chemistry and Biological Applications, edited by J. Milton Harris, S. Zalipsky, eds., American Chemical Society, Washington, D.C., (1997), ACS Symposium Series 680, Chapter 27, pp. 441–457; A. S. Hoffman, et al., Frontiers in Biomedical Polymer Applications, edited by R. M. Ottenbrite, Technomic Publishing Co., Lancaster, Pa. 1999, Vol. 2, pp. 17–29; A. S. Hoffman, et al., Block and graft copolymers and methods related thereto, Int. Pat. Appl. WO 95/24430.

Alternatively, syntheses known in the art can result in chemically cross-linked networks (gels, microgels, or nanogels) if both termini of the polyether are chemically modified. See, e.g., U.S. Pat. No. 6,316,011; L. Bromberg, Crosslinked poly(ethylene glycol) networks as reservoirs for protein delivery, J. Appl. Polym. Sci., 59(1996)459–466; L. Bromberg, Temperature-sensitive star-branched poly(ethylene oxide)-b-poly(propylene oxide)-b-poly(ethylene oxide) networks, Polymer, 39(23)(1998) 5663–5669; Law, T. K., et al., Int. J. Pharm., 1984, 21, 277; Ping, Q.,; Law, T. K., et al., Int. J. Pharm., 1990, 61, 79.

However, chemical moieties (amide or other) required to accomplish linkage between an amphiphilic copolymer such as polyether and the polyelectrolyte (i.e. a chemical group absent in parent polyether and polyelectrolyte) are generally toxic and unacceptable for use in pharmaceutical and other applications. Copolymers that comprise chemically unmodified amphiphilic copolymer and polyelectrolyte bonded only through carbon-carbon bond, where such toxicity issues are avoided, are known in the art. See, e.g., L Bromberg, et al., Responsive polymer networks and methods of their use, U.S. Pat. No. 5,939,485; E. S. Ron, et al., Compositions for pharmaceutical applications, Int. Patent Appl. WO 98/06438; E. S. Ron, et al., T. H. E. Mendum, Compositions for cosmetic applications, Int. Patent Appl. WO 98/50005; L Bromberg, *Hydrophobically modified polyelectrolytes and polyelectrolyte block-copolymers*, Handbook of Surfaces and Interfaces of Materials, H. S. Nalwa, ed., Academic Press, 2001, Vol. 4, Chapter 7; L Bromberg, *Biomedical applications of hydrophobically modified polyelectrolytes and polyelectrolyte block-copolymers*, S. Tripathy, J. Kumar, H. S. Nalwa, eds. Handbook of Polyelectrolytes and Their Applications. American Scientific Publishers, Stevenson Ranch, Calif., 2002, Vol. 1, Chapter 51; L. E. Bromberg, T. H. E. Mendum, M. Orkisz, E. S. Ron, E. C. Lupton, *Applications of poly(oxyethylene-b-oxypropylene-b-oxyethylene)-g-poly(acrylic acid) polymers (Smart Responsive microgel™) in drug delivery*, Proc. Polym. Mater. Sci. Eng., 76: 273–275, 1997; M. J. Orkisz, et al., *Rheological properties of reverse thermogelling poly(acrylic acid)-g-poly(oxyethylene-b-oxypropylene-b-oxyethylene) polymers (Smart Responsive microgel™)*, Proc. Polym. Mater. Sci. Eng., 76: 276–277, 1997; L. Bromberg, et al., *Interpenetrating networks of Poloxamer copolymers and poly(acrylic acid) as vehicles in controlled drug delivery*, J. Control. Release, 48 (2,3): 305–308, 1997; L. E. Bromberg, T. H. E. Mendum, M. J. Orkisz, E. C. Lupton, E. S. Ron, *Polyoxyethylene-b-polyoxypropylene-b-polyoxyethylene-g-poly(acrylic acid) polymers (Smart Responsive microgel™) as a* carrier in controlled delivery of proteins and peptides, Polym. Prepr., 38(2): 602–603, 1997; L. E. Bromberg, et al., *Bioadhesive properties of polyoxyethylene-b-polyoxypropylene-b-polyoxyethylene-g-poly(acrylic acid) polymers (Smart Responsive microgel™)*, Polym. Prepr., 38(2): 626–627, 1997; L. Bromberg, *A novel family of thermogelling materials via C—C bonding between poly(acrylic acid) and poly(ethylene oxide)-b-poly(propylene oxide)-b-poly(ethylene oxide)*, J. Phys. Chem. B, 102: 1956–1963, 1998; L. E. Bromberg, E. S. Ron, *Protein and peptide release from temperature-responsive gels and thermogelling polymer matrices*, Adv. Drug Delivery Revs., 31:197–221, 1998; L. E. Bromberg, M. G. Goldfeld, *Self-assembly in aqueous solutions of hydrophobically modified poly(acrylic acid)*, Polym. Prepr., 39(2):681–682, 1998; L. Bromberg, *Scaling of rheological properties of responsive microgels from associating polymers*, Macromolecules, 31: 6148–6156, 1998; L. Bromberg, *Self-assembly in aqueous solutions of polyether-modified poly(acrylic acid)*, Langmuir, 14: 5806–5812, 1998; L. Bromberg, *Polyether-modified poly(acrylic acid): synthesis and properties*, Ind. Eng. Chem. Res., 37: 4267–4274, 1998; L. Bromberg, *Properties of aqueous solutions and gels of poly(ethylene oxide)-b-poly(propylene oxide)-b-poly(ethylene oxide)-g-poly(acrylic acid)*, J. Phys. Chem B, 102: 10736–10744, 1998; L. Bromberg, L. Salvati, *Bioactive surfaces via immobilization of self-assembling polymers onto hydrophobic materials*, Bioconjugate Chem., 10: 678–686, 1999; L. E. Bromberg, *Interactions between hydrophobically modified polyelectrolytes and mucin*, Polym. Prepr., 40(2): 616–617, 1999; L. E. Bromberg, D. P. Barr, *Aggregation phenomena in aqueous solutions of hydrophobically modified polyelectrolytes*. Macromolecules, 32: 3649–3657, 1999; P. D. T. Huibers, et al., *Reversible gelation in semidilute aqueous solutions of associative polymers: a small-angle neutron scattering study*, Macromolecules, 32: 4889–4894, 1999; L. Bromberg, E. Magner, *Release of hydrophobic compounds from micellar solutions of hydrophobically modified polyelectrolytes*, Langmuir, 15: 6792–6798, 1999; L. Bromberg, M. Temchenko, *Loading of hydrophobic compounds into micellar solutions of hydrophobically modified polyelectrolytes*, Langmuir, 15: 8627–8632, 1999; L. E. Bromberg, M. Temchenko, R. H. Colby, *Interactions among hydrophobically modified polyelectrolytes and surfactants of the same charge*, Langmuir, 16: 2609–2614, 2000; N. Plucktaveesak, et al., *Effect of surfactants on gelation threshold temperature in aqueous solutions of hydrophobically modified polyelectrolyte*, Proc. XIIIth International Congress on Rheology, Cambridge, UK, 2000, Vol. 3, pp. 307–309; L. Bromberg, *Enhanced nasal retention of hydrophobically modified polyelectrolytes*, J. Pharm. Pharmacol., 53: 109–114, 2001; L. Bromberg, *Interactions among proteins and hydrophobically modified polyelectrolytes*, J. Pharm. Pharmacol., 53: 541–547, 2001; A. K. Ho, L. E. Bromberg, et al., *Solute diffusion in solutions of associative polymers*, Langmuir, 17: 3538–3544, 2001; R. H. Colby, et al., *Critical incorporation concentration of surfactants added to micellar solutions of hydrophobically modified polyelectrolytes of the same charge*, Langmuir, 17: 2937–2941, 2001; L. Bromberg, *Synthesis and self-assembly of poly(ethylene oxide)-b-poly(propylene oxide)-b-poly(ethylene oxide)-g-poly(acrylic acid) gels*, Ind. Eng. Chem. Res., 40: 2437–2444, 2001; L. Olivieri, et al., *Study of the breakup under shear of a new thermally reversible W/O/W multiple emulsion*, Pharm. Res., 18: 689–693, 2001; A. K. Ho, et al., *Hydrophobic domains in thermogelling solutions of polyether-modified poly(acrylic acid)*, Langmuir, 18: 3005–3013, 2002.

One-step methods of copolymer synthesis are known in the art, e.g., L. Bromberg, *J. Phys. Chem. B*, 1998, 102, 1956–1963; L. Bromberg, *Ind. Eng. Chem. Res.*, 1998, 37, 4267–4274; P. D. T. Huibers, et al., *Macromolecules*, 1999, 32, 4889–4894. However, these prior art graft-comb copolymers are not permanently cross-linked and therefore cannot respond volumetrically to changes in their environment.

Previous Work

A variety of formulation approaches have been developed aiming at the enhancement of the drug residence time and to lowering the release rate, while maintaining the mucoadhesive properties of the polyelectrolyte. See, e.g., K. J. Himmelstein, et al., U.S. Pat. No. 5,599,534; T X Viegas, et al., U.S. Pat. No. 5,292,516; R Joshi, et al., Pharm Dev Technol. 4: 515–522 (1999); Joshi, et al., U.S. Pat. No. 5,252,318. Typically, a polyelectrolyte is mixed with more hydrophobic polymer to result in a blend with enhanced drug-polymer interactions and higher viscosity. It is preferred, however, that a liquid drug-polymer formulation gel at the site of administration. Such in situ gelling systems undergo reversible sol-gel transitions in response to temperature, pH, or ion composition of the fluids. However, physical blends are colloidally unstable and either phase separate or dissociate at physiological pH. See, e.g., L Bromberg, Handbook of Surfaces and Interfaces of Materials, H. S. Nalwa, ed., Academic Press, 2001, Vol. 4, Chapter 7. Therefore, these blends fail to provide a linear, sustained release of a hydrophobic or amphiphilic compound such as imbibed or loaded drug, for example, in drug delivery applications.

Previous structures that result from the linking of the amphiphilic copolymers and polyelectrolyte though carbon-carbon bond (See FIG. 1, structure I (A.) and FIG. 2 structure III, for example) can form physical gels in water due to aggregation of the hydrophobic segments of the amphiphilic copolymers at certain temperatures and concentrations. However, by definition, previous gels are unstable upon dilution due to dissociation of the physical aggregates below a certain concentration. Accordingly, due to dissociation under physiological conditions, previous gels were not able to provide a linear, sustained release of a hydrophobic or amphiphilic compound such as imbibed or loaded drug, for example, in drug delivery applications. Further, previous structures that result from chemical linking on both termini (See FIG. 1, structure II (B.), for example) can form stable, chemically cross-linked networks. However, due to the steric constrains imposed by chemical linking on both termini, the hydrophobic parts of the amphiphilic copolymer are unable to aggregate at well-defined temperatures and concentrations. Therefore, nanosized aggregates do not form within the gel network. As a result, such previous gels also were not able to provide a linear, sustained release of a hydrophobic or amphiphilic compound such as imbibed or loaded drug, for example, in drug delivery applications.

SUMMARY OF THE INVENTION

A responsive microgel is provided which responds volumetrically and reversibly to a change in one or more aqueous conditions selected from the group consisting of (temperature, pH, and ionic conditions) comprised of an ionizable network of covalently cross-linked homopolymeric ionizable monomers wherein the ionizable network is covalently attached to an amphiphilic copolymer to form a plurality of 'dangling chains' and wherein the 'dangling chains' of amphiphilic copolymer form immobile micelle-like aggregates in aqueous solution.

A responsive microgel is further provided that comprises at least one therapeutic entity and delivers a substantially linear and sustained release of the therapeutic entity under physiological conditions.

A responsive microgel is also provided wherein the ionizable network of covalently cross-linked homopolymeric ionizable monomers is selected from the group consisting essentially of (poly(acrylic acid), poly(methacrylic acid), poly(4-vinylpyridinium alkyl halide), poly(sodium acrylate), poly(sodium methacrylate), sulfonated polyisoprene, and sulfonated polystyrene).

A further responsive microgel is provided wherein an amphiphilic copolymer is comprised of (poly(ethylene oxide) and a monomer selected from the group consisting essentially of (poly(propylene oxide), poly(butylene oxide), polystyrene, polyisobutylene, poly(methyl methacrylate), and poly(tert-butyl acrylate)).

A method of making a responsive microgel is also provided comprising:

a) providing, an ionizable monomer, a divinyl cross-linker, a free radical, and a amphiphilic copolymer; and b) copolymerizing the ionizable monomer with the divinyl cross-linker to produce an ionizable network, while c) abstracting hydrogen from the amphiphilic copolymer with the free radical to progress a chain transfer reaction wherein the amphiphilic copolymer is covalently bonded onto the ionizable network to produce the responsive microgel.

A method of administering an effective amount of at least one therapeutic entity to a patient is further provided which comprises administering a responsive microgel comprising an effective amount of at least one therapeutic entity.

A method is provided for administering at least one therapeutic entity to a patient which entity is selected from the group consisting of substrates of ABC transporters such as P-glycoprotein, MRP1–MRP9; ABC half-transporters such as BCRP; other transporters that are involved into a limited drug transport across small intestinal epythlium; cerebral endothelium and other barrier tissues in the body, as well as substrates of metabolic enzyme isoforms without limitation, cytochrome P-450; esterase; epoxide hydrolase; alcohol dehydrogenase; aldehyde dehydrogenase; dihydropyrimidine dehydrogenase; NADPH-quinone oxidoreductase; uridine 5'-triphosphat glucoronosyltransferase; sulfotransferase; glutathione S-transferase; N-aceltiltransferase; histamine methyltransferase; catechol-o-methyl transferase; thiopurine methyltransferase. This group of therapeutic agents include without limitation doxorubicin and other anthracyclines, mitoxantrone, mitomycin C, metatrexate, paclitaxel, docetaxel and other taxanes, topotecan ant other camptotecines, cysplatin, carboplatin, oxaliplatin and other platinum complexes; megesterol acetate and other steroids; carvedilol and other beta-blocking agents; azidothymidine, fludarabine and other nucleoside containing agents in their dephospho, mono-, di- and tri-phosphorylated forms; vinblastine, vincristine and other vinka alkaloids; etoposide and other podophilotoxins.

BRIEF DESCRIPTION OF THE FIGURES

FIG. 4 is a flowchart illustration of one-step synthesis of responsive microgels of the present invention.

DETAILED DESCRIPTION OF THE INVENTION

The present invention relates to stable chemically cross-linked networks (gels) of a polyelectrolyte wherein 'dangling chains' of at least one amphiphilic co-polymer are bonded thereto through carbon-carbon bonding. The dangling chains are capable of forming intra-network micelle-like aggregates. The aggregates possess the ability to imbibe a large quantity of, for example, hydrophobic or amphiphilic compounds. Due to the formation of mixed aggregates, the responsive-microgel networks of the present invention display linear and sustained release of hydrophobic or amphiphilic compounds in aqueous milieu. Further, the formation of micelle-like aggregates within the chemically cross-linked polyelectrolyte network of the present invention is reversible.

The responsive microgel described herein is, for example, (1) able to imbibe large quantities of at least one ionic, amphiphilic, or hydrophobic compound, and (2) forms micelle-like aggregates within its structure when in aqueous solution and (3) allows for a sustained, substantially linear release of the compound in vitro and/or in vivo, for example, under the temperature, pH, and ionic composition of physiological conditions. A preferred embodiment of the present invention is method of delivering an effective amount of at least one therapeutic agent to a patient comprising administering an effective amount of a responsive microgel of the present invention, which comprises at least one therapeutic agent. The responsive microgels of the present invention are suitable for oral administration, for example, and hence the oral delivery of therapeutic agents.

Figure 7:
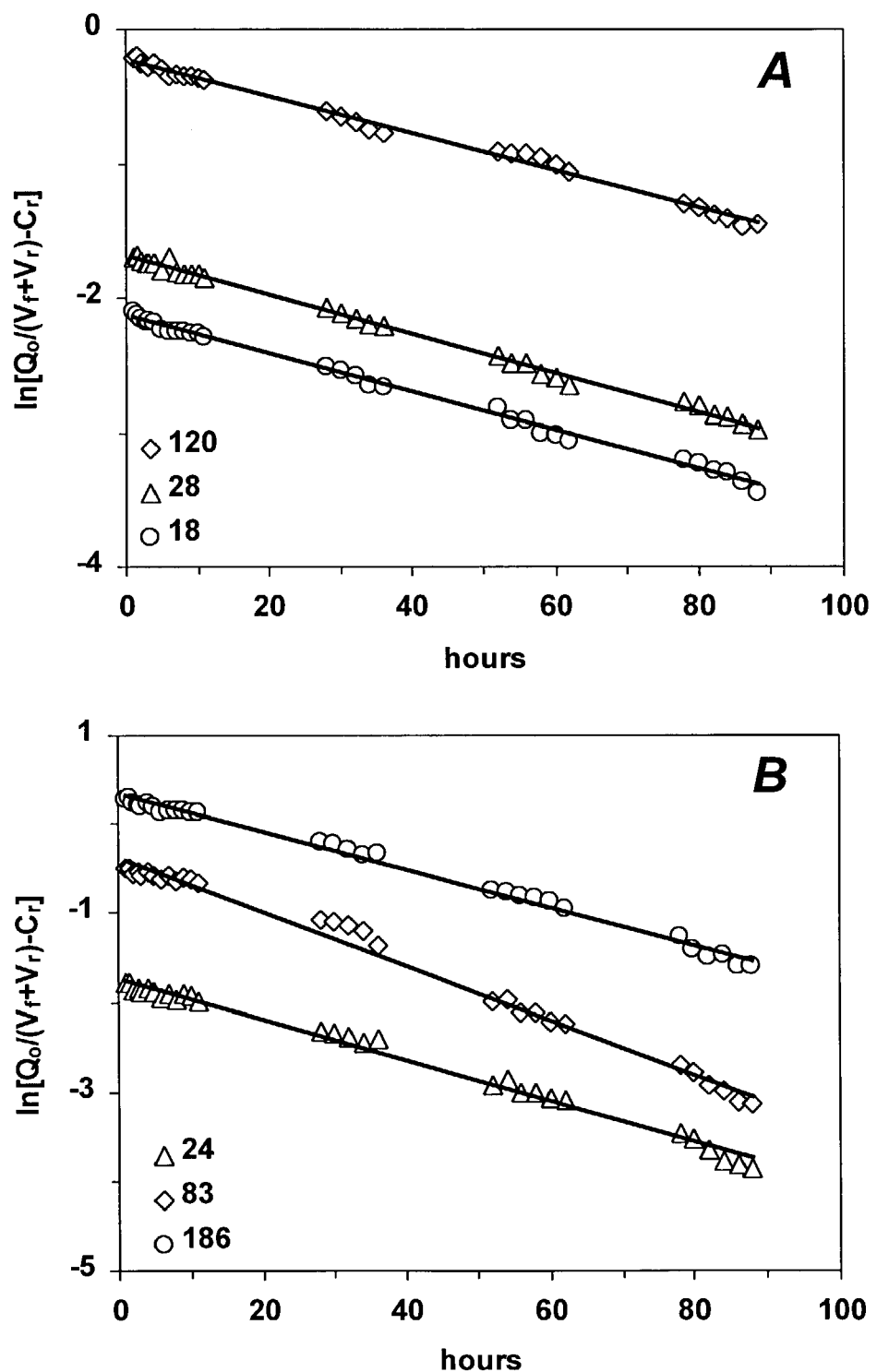
FIG. 7 shows the kinetics of doxorubicin release from a responsive microgel.

Drug release kinetics from example responsive microgels of the present invention are provided herein. Example I shows that loading of corresponding drugs into a responsive microgel greatly affected the kinetics of release. The drugs loaded into the microgel exhibited slow, sustained release kinetics. Kinetics of doxorubicin release from a responsive microgel is shown in FIG. 7. Three cationic and one uncharged drug was loaded onto the microgel in Example VII, all of which are currently in clinical use as anticancer drugs. Doxorubicin, mitoxantrone, and mitomycin C are mono-, di-, and trivalent cationic weak bases, respectively. Taxol is uncharged (hydrophobic). The ability of responsive microgels of the invention to effectively load and hold taxol, combined with mucoadhesive properties is a feature important for delivery of taxol and other hydrophobic solutes such as steroid hormones. The taxol loading capacity provides additional evidence to the mechanism of taxol solubilization into micelle-like aggregates within the responsive microgels. Drug loading via ion-exchange are illustrated using the potent chemotherapeutic drug doxorubicin.

The responsive microgel of the present invention comprises two responsive components: An amphiphilic copolymer (nonionic copolymer) capable of aggregation in response to a change in temperature; and, an ionizable, covalently cross-linked polymeric network of monomers which responds volumetrically to changes in aqueous conditions such as pH or ionic composition by swelling or collapsing. Since both responsive components, i.e., the nonionic copolymer and the cross-linked polymermeric network of monomers which contain ionizable groups are bound through covalent bonds, each polymer has a chemical or mechanical influence over the swelling of the other polymeric component. The resulting responsive microgel exhibits volumetric changes in response to variations in pH as well as temperature. See, Examples III–V. These responsive microgel graft-comb copolymers dissolve freely in aqueous solutions and self-assemble in response to changes in conditions such as pH and temperature.

Figure 1:
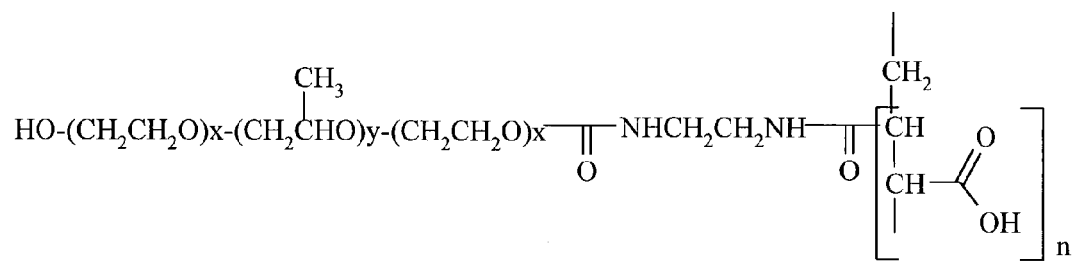
FIG. 1 shows previous structures (A.) (structure I) and (B.) (structure II) that result from the linking of amphiphilic copolymers and polyelectrolyte though carbon-carbon bonds.
Figure 1:
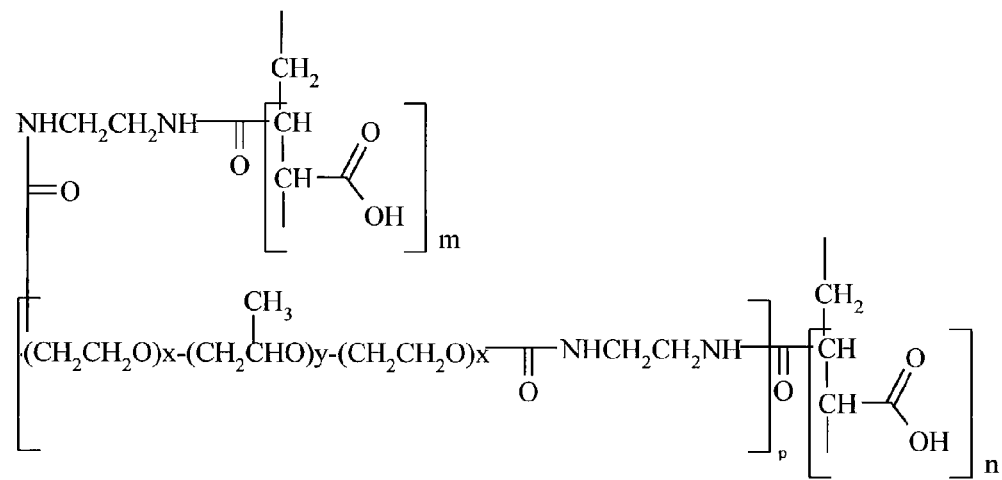
Figure 2:
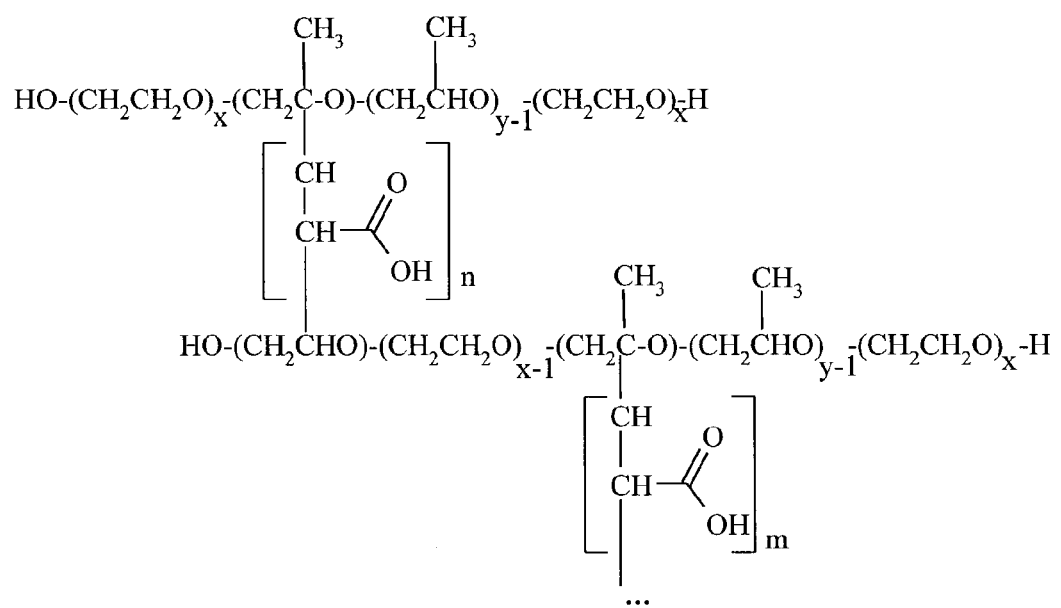
FIG. 2 shows another previous structure (structure III) that results from the linking of amphiphilic copolymers and polyelectrolyte though carbon-carbon bonds.
Figure 3:
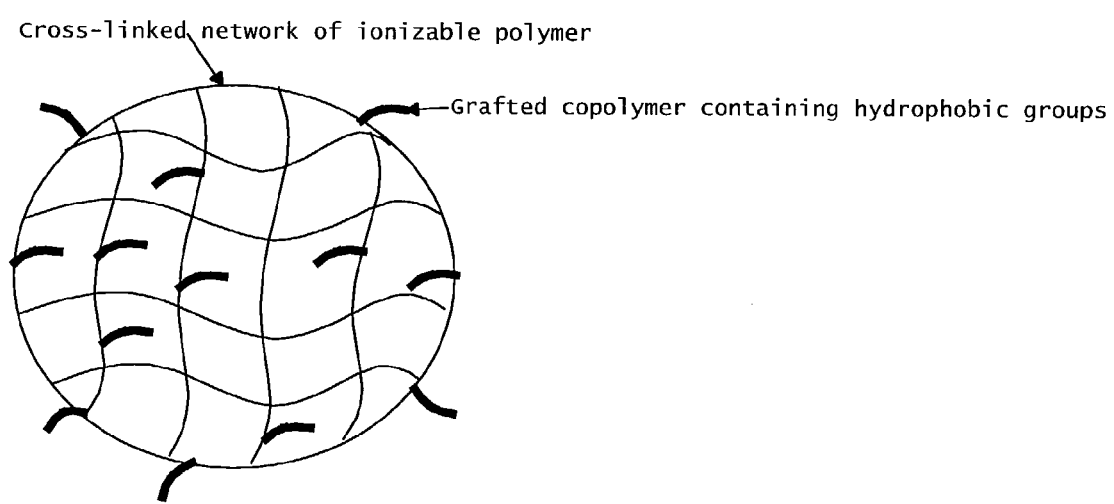
FIG. 3 is a general macro-illustration of the overall ionizable network and the covalently attached 'dangling chains' (amphiphilic copolymer) structure of the responsive microgel described herein.

The microgel covalently cross-linked polymer network of the present invention is comprised of at least one amphiphilic copolymer covalently attached (preferably a carbon-carbon bond from a single terminal region of each amphiphilic copolymer) to an ionizable network (polyelectrolyte). The amphiphilic copolymer forms the 'dangling chain' component of the responsive microgel which forms micelle-like aggregates within the covalently cross-linked polymer network in aqueous solution. See, FIG. 3 (structure of the responsive microgel).

The term "responsive" in reference to the microgel of the present invention refers to reversible phase transition characteristics, e.g., volumetric change, which result from exposure to a change in one or more environmental factors under aqueous conditions, such as temperature, pH, and ionic conditions. The microgels operate as described herein within the temperature range of about −4° C. to about 55° C., preferably from about 0 to about 37° C. The microgels will be collapsed at pH 1–3 such as in stomach and swollen at pH exceeding the pKa of their carboxylic groups, i.e. at pH>4.5 (fully swollen at pH 7.4, for example). The gel is collapsed (swelling degree preferably not exceeding 50 v/v % of water per polymer) at acidic pH such as in stomach, but fully swollen (swelling degree preferably exceeding 100–5000 v/v % of liquid per polymer) in the intestine. The gels protect the therapeutic entity, e.g., embedded drug, and hold it without release when collapsed, but rapidly release when swollen. The range of operation of the microgels of the present invention are solutions of ionic strength preferably below 1 M, or from 0M to 5 M, for example. A change in these environmental factor(s) affects the responsive microgel by causing the structure to undergo a reversible volumetric change in which the gel increases volume by expanding (swelling) or decreases volume by collapsing (contraction).

Phase transitions in gels may be explained, for example, by the following equation. One may determine the effect of ionic groups on the reduced chemical potential ($\Delta\mu_1$) for solvent in an isotropically swollen gel network:

$$\Delta\mu_1 = (\mu_1 - \mu_1^0)/RT = \ln(1 - v_2) + v_2 + \chi v_2^2 + f(\lambda) + \frac{\Delta\mu_i}{RT} = \ln a_i$$

where $a_1$ is the activity of the solvent in the network, $\chi$ is the interaction parameter, $V_2$ is the volume fraction of the polymer, $f(\lambda)$ is the function of the deformation tensor, $\Delta\mu_i$ is the contribution to the total chemical potential by the presence of ionic groups on the chains.

Example I describes the favorable linear release of monomeric PLURONIC® from the microgels. It was discovered that PLURONIC® 161, for example, has exceptionally low release rate and sustained release for over 10 days due to the formation of mixed micelles between added PLURONIC® 161 and PLURONIC® covalently grafted to a poly(acrylic acid) network in the process of synthesis. Such mixed, immobile micelles can provide thermodynamically stable environment for the PLURONIC® solute, making its effective partition coefficient between micelles and water to be very low. These results are unique and exceptionally well suited for the intended application of the novel microgels in drug delivery.

Compositions

I. Ionizable Network

The ionizable network is a covalently cross-linked homopolymeric network of ionizable monomers. The monomers of the ionizable network each contain at least one ionizable group. The ionizable network responds volumetrically to changes in aqueous conditions such as pH or ionic composition by swelling or collapsing. Preferred embodiments of this polyelectrolyte network (onto which the amphiphilic copolymer 'dangling chains' are attached via C—C bond to form the responsive microgel) are comprised of a monomer selected from the group consisting essentially of (poly(acrylic acid), poly(methacrylic acid), poly(4-vinylpyridinium alkyl halide), poly(sodium acrylate), poly (sodium methacrylate), sulfonated polyisoprene, and sulfonated polystyrene).

Preferred polyanion-forming compounds include poly (acrylic acid), poly(methacrylic acid), and poly(2-ethylacrylic acid); preferred polycation-forming compounds include polyethyleneimine and polyethylenepiperazine. The hydrophilic blocks recited infra, (i.e., A. Hydrophilic Monomers and Polymers), can also be used in the compositions described herein either as an element of the ionizable network (polyelectrolyte).

A. Polyanion Forming Compounds

Ionizable compounds for the ionizable network of the present invention also include, but are not limited to, polyanion-forming compounds such as poly(acrylic acid), poly (methacrylic acid), poly(maleic acid), poly(styrenesulfonic acid), poly(itaconic acid), poly(vinyl sulfate), poly(vinylsulfonic acid), poly(vinyl phosphate), poly(acrylic acid-co-maleic acid), poly(styrenesulfonic acid-co-maleic acid), poly(ethylene-co-acrylic acid), poly(phosphoric acid), poly (silicic acid), hectorite, bentonite, alginic acid, pectic acid, kappa-, lambda- and iota-carrageenans, xanthan, gum arabic, dextran sulfate, carboxymethyldextran, carboxymethylcellulose, cellulose sulfate, cellulose xanthogenate, starch sulfate and starch phosphate, lignosulfonates, karaya gum; polygalacturonic acid, polyglucuronic acid, polyguluronic acid, polymannuronic acid and copolymers thereof; chondroitin sulfate, heparin, heparan sulfate, hyaluronic acid, dermatan sulfate, keratan sulfate; poly-(L)-glutamic acid, poly-(L)-aspartic acid, deoxyribonucleic acid, ribonucleic acid, acidic gelatins (A-gelatins); starch, amylose, amylopectin, cellulose, guar, gum arabic, karaya gum, guar gum, pullulan, xanthan, dextran, curdlan, gellan, carubin, agarose, as well as chitin and chitosan derivatives having the following functional groups in various degrees of substitution: carboxymethyl and carboxyethyl, carboxypropyl, 2-carboxyvinyl, 2-hydroxy-3-carboxypropyl, 1,3-dicarboxyisopropyl, sulfomethyl, 2-sulfoethyl, 3-sulfopropyl, 4-sulfobutyl, 5-sulfopentyl, 2-hydroxy-3-sulfopropyl, 2,2-disulfoethyl, 2-carboxy-2-sulfoethyl, maleate, succinate, phthalate, glutarate, aromatic and aliphatic dicarboxylates, xanthogenate, sulfate, phosphate, 2,3-dicarboxy, N,N-di(phosphatomethyl) aminoethyl, N-alkyl-N-phosphatomethylaminoethyl. These derivatives may additionally comprise nonionic functional groups in various degrees of substitution, such as methyl, ethyl, propyl, isopropyl, 2-hydroxyethyl, 2-hydroxypropyl and 2-hydroxybutyl groups, for example, as well as esters with aliphatic carboxylic acids, e.g., ($C_2$ to $C_{18}$).

B. Polycation Forming Compounds

Examples of polycation-forming compounds for the ionizable network of the present invention also include, but are not limited to, poly(alkyleneimines), especially poly(ethyleneimine), poly-(4-vinylpyridine), poly(2-vinylpyridine), poly(2-methyl-5-vinylpyridine), poly(4-vinyl-N—$C_1$–$C_{18}$-alkylpyridinium salt), poly(2-vinyl-N—$C_1$–$C_{18}$-alkylpyridinium salt), polyallylamine, polyvinylamine, aminoacetylated polyvinyl alcohol; the polysulfone dialkylammonium salts; basic proteins, poly-(L)-lysine, poly-(L)-arginine, poly (ornithine), basic gelatins (B-gelatins), chitosan; chitosan with various degrees of acetylation; starch, amylose, amylopectin, cellulose, guar, gum arabic, karaya gum, guar gum, dextran, pullulan, xanthan, curdlan, gellan, carubin, agarose, as well as chitin and chitosan derivatives having the following functional groups in various degrees of substitution: 2-aminoethyl, 3-aminopropyl, 2-dimethylaminoethyl, 2-diethylaminoethyl, 2-diisopropylaminoethyl, 2-dibutylaminoethyl, 3-diethylamino-2-hydroxypropyl, N-ethyl-N-methylaminoethyl, N-ethyl-N-methylaminopropyl, 2-diethylhexylaminoethyl, 2-hydroxy-2-diethylaminoethyl, 2-hydroxy-3-trimethylammonionopropyl, 2-hydroxy-3-triethylammonionopropyl, 3-trimethylammonionopropyl, 2-hydroxy-3-pyridiniumpropyl and S,S-dialkylthioniumalkyl. These derivatives may additionally comprise nonionic functional groups in various degrees of substitution, such as methyl, ethyl, propyl, isopropyl, 2-hydroxymethyl, 2-hydroxypropyl and 2-hydroxybutyl groups, for example, and also esters with aliphatic carboxylic acids ($C_2$ to $C_{18}$); and also n,m-ionenes, poly(aniline); poly(pyrrole); poly (viologens) and also poly(amidoamines) based on piperazine.

II. Amphiphilic Copolymer

A preferred amphiphilic copolymer (nonionic copolymer) component for use in the methods and compositions in the present invention is a copolymer of an ionizable monomer and a hydrophobic monomer. The amphiphilic copolymer is preferably comprised of a nonionic hydrophilic monomer and nonionic hydrophobic monomer. Amphiphilic copolymers for use in constructing microgels of the present invention are selected from amphiphilic diblock copolymers, amphiphilic triblock copolymers, amphiphilic multiblock copolymers, and amphiphilic graft copolymers. The amphiphilic copolymer is preferably a di- or triblock copolymer. The amphiphilic copolymer is preferably comprised of (poly(ethylene oxide) and a monomer selected from the group consisting essentially of (poly(propylene oxide), poly (butylene oxide), polystyrene, polyisobutylene, poly(methyl methacrylate), and poly(tert-butyl acrylate)).

Amphiphilic copolymers for use in constructing responsive microgels of the present invention generally have a molecular weight in the range of from about 200 to about 1,000,000, preferably from about 500 to about 500,000, and more preferably from about 200 to about 200,000. The amphiphilic copolymers generally have a hydrophilic/lipophilic balance in the range of from about 0.001 to about 100.

A preferred embodiment of the present invention comprises an amphiphilic copolymer comprised of a diblock, triblock, or multiblock copolymer, preferably a diblock or triblock copolymer, more preferably a diblock copolymer. A particularly preferred embodiment comprises a triblock copolymer wherein one block comprises polyoxyethylene. Another particularly preferred embodiment comprises a triblock copolymer wherein one block comprises polyoxypropylene.

Any of the hydrophilic blocks of various chemistry and formula weight of the amphiphilic copolymers herein can be used in combination with any of the hydrophobic blocks of various chemistry and formula weight to compose an amphiphilic 'dangling chain'. The hydrophilic blocks recited infra (i.e., A. Hydrophilic Monomers and Polymers) can be used in the compositions described herein either as an element of the ionizable network (polyelectrolyte) and/or an element of an amphiphilic 'dangling chain' copolymer.

The hydrophilic blocks of the amphiphilic diblock, triblock, or multiblock copolymers can have formula weights in the range from about 200 to about 500,000, preferably from about 2,500 to about 250,000, more preferably from about 500 to about 100,000. The hydrophobic blocks of the amphiphilic diblock, triblock, or multiblock copolymers useful in the present invention can have formula weights in the range of from about 1,000 to about 500,000, preferably from about 2,500 to about 250,000, more preferably from about 500 to about 100,000.

Amphiphilic graft copolymers useful in the present invention possess rotatable side chain block regions that can rotate or fold to become part of the aggregates within the microgels of the present invention. The number of side chains present in each of the amphiphilic graft copolymers can be in the range of from about 1 to about 10000. The formula weights of the various blocks in the amphiphilic copolymers can be varied independently of each other.

A. Hydrophilic Monomers and Polymers

Examples of monomer repeat units that can be used in the preparation of hydrophilic blocks of the amphiphilic copolymer (or as monomers of the ionizable network) are set forth as follows. Poly(acrylic acid) and poly(metal acrylates) are preferred.

1. Example Monomer Units Useful as Repeat Units in Hydrophilic Blocks

Polyacrylic acid Poly(metal acrylate), M=Li, Na, K, Cs
Polyacrylamide Poly(methacrylic acid), R=H, alkyl
Poly(metal methacrylate) Polymethacrylamide
M=Li, Na, K, Cs R=H, alkyl
Polystyrene sulfonic acid Polystyrene sulfonic acid metal salt, M=Li, Na, K, Cs
Polystyrene carboxylic acid Polystyrene carboxylic acid, metal salt M=Li, Na, K, Cs
Poly(vinyl alcohol), R=H, alkyl
Poly(4-vinyl-N-alkyllpyridinium halide), R=H, alkyl
Poly(2-vinyl-N-alkyllpyridinium halide)\Poly(hydroxyethyl methacrylate)
Poly(itaconic acid)
Poly(N,N,N-trialkyl-4-vinylphenylammonium halide)
Poly(N,N,N-trialkyl-4-vinylbenzylammonium halide)
Percent quaternization 10% to 70%
Poly(N,N,N-trialkyl-4-vinylphenethylammonium halide)
Poly(L-glutamic acid) Poly(L-aspartic acid) Hyaluronic acid Amino acids used to compose hydrophilic blocks of the amphiphilic copolymer:
Serine Threonine
Tyrosine Lysine
Arginine Histidine
Aspartic acid Glutamic acid 2. Example Polymers Useful as Hydrophilic Blocks Polymers as hydrophilic blocks of the nonionic copolymer (amphiphilic copolymer) for employment in the 'dangling chains' of the responsive microgel of the present invention also include, but are not limited to:
Poly(sodium 1-carboxylatoethylene), Poly(5-hydroxy-1-pentene), 5,8-poly-5,7-dodecadiynediol, 10,13-poly-10,12-heptacosadiynoic acid, 2,5-poly-2,4-hexadienedioic acid, 2,5-poly-2,4-hexadienoic acid, (6-amino)-2,5-poly-2,4-hexadienoic acid, (6-amino)2,5-poly-2,4-hexadienoic acid, hydrochloride, 2,5-poly-2,4-hexadiynediol, 10,13-poly-10,12-nonacosadiynoic acid, 2,5-poly-2,4,6-octatriynediol, 10,13-poly-10,12-pentacosadiynoic acid, 2,5-poly-5-phenyl-2,4-pentadienoicacid, Poly(2-aminoisobutyric acid), dichloroacetic acid complex, Poly(L-arginine), Poly(L-nitroarginine), Poly(L-aspartic acid), Poly(beta-benzyl-L-aspartic acid), Poly[beta-(p-chlorobenzyl)-L-aspartic acid], Poly(beta-ethyl-L-aspartic acid), Poly[beta-(2-phenyl-ethyl)-L-aspartic acid], Poly(alpha-isobutyl-L-aspartic acid), Poly(beta-N-propyl-L-aspartic acid), Poly(2,4-diaminobutyric acid), Poly(N-benzyloxycarbonyl-2,4-diaminobutyric acid), Poly(D-glutamic acid), Poly(gamma-benzyl-D-glutamic acid), Poly(gamma-m-chloro-benzyl-D-glutamic acid), Poly(gamma-o-chloro-benzyl-D-glutamic acid), Poly(gamma-p-chloro-benzyl-D-glutamic acid), Poly(gamma-methyl-D-glutamic acid), Poly(gamma-phthalimidomethyl-L-glutamic acid), Poly(gamma-N-amyl-L-glutamic acid), Poly(gamma-benzyl-L-glutamic acid), Poly(gamma-m-chloro-benzyl-L-glutamic acid), Poly(gamma-o-chloro-benzyl-L-glutamic acid), Poly(gamma-p-chloro-benzyl-L-glutamic acid), Poly(gamma-N-butyl-L-glutamic acid), Poly(gamma-N-dodecyl-L-glutamic acid), Poly(gamma-N-ethyl-L-glutamic acid), Poly[gamma-N-(2-chloroethyl)-L-glutamic acid], Poly[gamma-N-(2-phenyl-ethyl)-L-glutamic acid], Poly(gamma-N-hexyl-L-glutamic acid), Poly(gamma-methyl-L-glutamic acid), Poly(gamma-methyl-L-glutamic acid), dimethylphthalate complex, Poly(gamma-N-octyl-L-glutamic acid), Poly(gamma-N-propyl-L-glutamic acid), Poly[gamma-N-(3-phenyl-propyl)-L-glutamic acid], Poly(L-glutamine), Poly[N5-(4-hydroxybutyl)-L-glutamine], Poly[N5-(2-hydroxyethyl)-L-glutamine], Poly[N5-(3-hydroxypropyl)-L-glutamine], Poly(D-glutamyl-L-glutamic acid), Poly(gamma-benzyl-D-glutamyl-L-glutamic acid), Poly(gamma-ethyl-D-glutamyl-L-glutamic acid), Poly[gamma-(2-phenyl-ethyl)-D-glutamyl-L-glutamic acid], Poly(L-histidine), Poly(1-benzyl-L-histidine), Poly(L-histidine), hydrochloride, Poly(gamma-hydroxy-L-alpha-aminovaleric acid), Poly(L-lysine), Poly(E-benzyloxycarbonyl-L-lysine), Poly(L-lysine), hydrobromide, Poly(L-methionine-s-carboxymethylthetin), Poly(L-methionine-s-methylsulfonium bromide), Poly(L-serine), Poly(gamma-hydroxy-L-proline), Poly(hydroxymethylene), Poly(1-hydroxytrimethylene), Poly(3,3-bishydroxymethyltrimethylene oxide), Poly(3-hydroxytrimethylene oxide), Poly(vinyl alcohol), Poly(ethylene glycol), Poly(2-methyl-vinyl alcohol), Poly(hydroxymethylene), Poly(cinnamic acid), Poly(crotonic acid), Poly(3-bromo acrylic acid), Poly(3-ethyl acrylic acid), Poly(N-acetyl-alpha-amino acrylic acid), Poly(alpha-bromoacrylic acid), Poly(alpha-chloroacrylic acid), Poly(alpha-fluoroacrylic acid), Poly(sodium alpha-chloroacrylate), Poly(3-oxa-5-hydroxypentyl methacrylate), Poly(2-hydroxyethyl acrylate), Poly(2-hydroxypropyl acrylate), Poly(beta-chloro-2-hydroxypropyl acrylate), Poly[N-(2-hydroxyethyl)-3,6-dichlorocarbazolyl acrylate], Poly[N-(2-hydroxyethyl)carbazolyl acrylate], Poly(acryloyl-beta-hydroxyethyl-3,5-dimitrobenzoat), Poly(methacryloyl-beta-hydroxyethyl-3,5-dimitrobenzoat), Poly(N-(2-hydroxyethyl)carbazolyl methacrylate), Poly(2-hydroxyethyl methacrylate), Poly(2-hydroxypropyl methacrylate), Poly(3-methoxy-2-hydroxypropyl methacrylate), Poly[1-(2-hydroxyethyl)pyridiniumbenzene sulfonate methacrylate], Poly[1-(2-hydroxyethyl)trimethylammoniumbenzene sulfonate methacrylate], Poly[N-(2-hydroxyethyl)phthalimido methacrylate], Poly[N-(hydroxyethyl)carbazolyl methacrylate], Poly(N-ethyl-3-hydroxymethylcarbazolyl methacrylate), Poly(2-sulfonic acid-ethyl methacrylate), Poly(2-trimethylammonium ethyl methacrylate chloride), Poly(2-trimethylammoniummethyl methacrylate chloride), Poly(methacrylonitrile), Poly(thiolacrylic acid), Poly(acrylonitrile), Poly(acrylamide), Poly(methacrylamide), Poly(N,N-dimethylacrylamide), Poly[(N-methylol)acrylamide], Poly[N-methoxymethyl methacrylamide], Poly(N-methyl methacrylamide), Poly(N-2-methoxyethyl methacrylamide), Poly[N-(2-hydroxypropyl)methacrylamide], Poly(2-methylpropanesulfonate sodium 2-acrylamido), Poly(2-methylpropanesulfonic acid 2-acrylamido), Poly[(p-amino)-styrene], Poly[4-(4-hydroxybutoxymethyl)styrene], Poly[4-(2-hydroxyethoxymethyl)styrene], Poly[4-(2-hydroxyiminoethyl)styrene], Poly[4-(1- hydroxyiminoethyl)styrene], Poly[4-(n-2-hydroxybutyl) styrene], Poly[4-(1-hydroxy-3-dimethylaminopropyl)styrene], Poly [4-(1-hydroxy-1-methylbutyl)styrene], Poly [4-(1-hydroxy-1-methylethyl)styrene], Poly[4-(1-hydroxy-1-methylhexyl)styrene], Poly[4-(1-hydroxy-1-methylpentyl)styrene], Poly[4-(1-hydroxy-1-methylpropyl)styrene], Poly(2-hydroxymethylstyrene), Poly(3-hydroxymethylstyrene), Poly(4-hydroxymethylstyrene), Poly(4-hydroxy styrene), Poly[p-1-(2-hydroxybutyl)-styrene], Poly[p-1-(2-hydroxypropyl)-styrene], Poly[p-2-(2-hydroxypropyl)-styrene], Poly[4-(1-hydroxy-3-morpholinopropyl)styrene], Poly[4-(1-hydroxy-3-piperidinopropyl)styrene], Poly(p-octylamine sulfonate styrene), Poly(2-carboxystyrene), Poly(4-carboxystyrene), Poly(styrene sulfonic acid), Poly(vinyl sulfonic acid), Poly[N-(2-hydroxypropyl)methacrylamide], Poly[oxy(hydroxyphosphinylidene)], Poly(9-vinyladenine), Poly(vinyl carbamate), Poly(vinylpyrrolidone), Poly(vinyl succinamic acid), Poly(N-isopropylacrylamide), Poly (methacrylic acid), Poly(itaconic acid), Poly(glycidyl methyl itaconate), Poly(monomethyl itaconate), Poly[N-(p-chlorophenyl)itaconimide], Poly[N-(p-tolyl)itaconimide], Poly[N-(2-chloroethyl)itaconimide], Poly[N-(4-acetoxyphenyl)itaconimide], Poly[N-(4-chlorophenyl) itaconimide], Poly[N-(4-ethoxycarbonylphenyl) itaconimide], Poly(N-benzylitaconimide), Poly(N-butylitaconimide), Poly(N-ethylitaconimide), Poly(N-isopropylitaconimide), Poly(N-isobutylitaconimide), Poly(N-methylitaconimide), Poly(N-naphthylitaconimide), Poly(N-phenylitaconimide), Poly(N-propylitaconimide), Poly(N-tolylitaconimide), Poly(alpha-chlorovinyl acetic acid), Poly(carboxychloromethyl ethylene), Poly (4-vinyl phenol), Poly(o-hydroxy-vinylphenylketone), Poly(alpha-phenylvinyl phosphonic acid), Poly[(1,2,5-trimethyl-4,4i-hydroxypyridiumchlorideethynyl)ethylene], Poly(allyl alcohol), Poly(acrylic acid), Poly[2-(3-sodium sulfonato-2-methylpropyl)methacrylamide], Poly(3-sodium sulfonatopropyl methacrylate), Poly(3-oxa-5-hydroxypentyl methacrylate), Poly(diethyleneglycol dimethacrylate), Poly(trimethyleneglycol dimethacrylate), Poly(triethyleneglycol dimethacrylate), Poly(ethyleneglycol N-phenylcarbamate methacrylate), Poly(acryloyl-L-glutamic acid), Poly(methacryloyl-L-glutamic acid), Poly(butadiene-1-carboxylic acid), Poly(crotonate acid), Poly(trans-4-ethoxy-2,4-pentadienoicacid), Poly (alpha-phenylvinyl phosphonic acid), Poly(vinylbenzoic acid), Poly(2-acryloyloxybenzoic acid), Poly[1-(2-hydroxyethylthio)-1,3-butadiene], Poly(2,5-dicarboxylic acid-1-hexene), Poly(3-hydroxyisoprene), Poly(alpha-phenylvinylphosphonic acid), Poly(2-chloro-3-hydroxy propene), Poly(2-p-vinylphenylpropanol), Poly(o-hydroxy-vinylphenylketone), Poly(1-vinyl-3-benzyl-imidazolium chloride), Poly(4-vinylbenzyltrimethylammonium chloride), Poly(4-vinylbenzyldimethyl vinylbenzyl ammonium chloride), Poly(4-vinylbenzyldimethyl methacryloyl ammonium chloride), Poly(4-vinylbenzyldimethyl acryloyl ammonium chloride), Poly(4-vinylbenzyldimethyl allyl ammonium chloride), Poly(4-vinylphenyltrimethylammonium chloride), Poly(4-vinylphenyl dimethyl vinylbenzyl ammonium chloride), Poly(4-vinylphenyl dimethyl methacryloyl ammonium chloride), Poly(4-vinylphenyl dimethyl acryloyl ammonium chloride), Poly(4-vinylphenyl dimethyl allyl ammonium chloride), Poly(4-vinylphenyltrimethylammonium chloride), Poly(4-vinylphenethyldimethyl vinylbenzyl ammonium chloride), Poly(4-vinylphenethyldimethyl methacryloyl ammonium chloride), Poly(4-vinylpheneth-yldimethyl acryloyl ammonium chloride), Poly(4-vinylphenethyldimethyl allyl ammonium chloride), Poly (vinyl acetate), Poly(vinyl butyral), Poly(acetaldehyde), Poly(ethylene oxide), Poly(2-cyanoethyloxymethylene oxide), Poly[(methoxymethyl)ethylene oxide], Poly(methylene sulfide), Poly(ethylene disulfide), Poly(ethylene sulfide), Poly(ethylene tetrasulfide), Poly(methylene disulfide), Poly(trimethylene disulfide), Poly(ethylene amine), Poly(propylene amine), Poly(4-vinyl-N-methylpyridinium chloride), Poly(4-vinyl-N-ethylpyridinium chloride), Poly[4-(2-dimethylaminoethoxycarbonyl)styrene], hydrochloride, Poly(4-vinylpyridine), hydrogen chloride, Poly(4-vinyl-N-vinylbenzylpyridinium chloride), Poly(4-vinyl-N-methacryloylpyridinium chloride), Poly(4-vinyl-N-acryloylpyridinium chloride), Poly(4-vinyl-N-allylpyridinium chloride), Poly(2-vinyl-N-methylpyridinium chloride), Poly(2-vinyl-N-ethylpyridinium chloride), Poly(2-vinyl-N-vinylbenzylpyridinium chloride), Poly(2-vinyl-N-methacryloylpyridinium chloride), Poly(2-vinyl-N-acryloylpyridinium chloride), Poly(2-vinyl-N-allylpyridinium chloride), and Poly(2-vinylpyridine) hydrogen chloride.

B. Hydrophobic Monomers and Polymers

The hydrophobic blocks of the amphiphilic diblock, triblock, or multiblock copolymers useful in the present invention can have formula weights in the range of from about 500 to about 500,000, preferably from about 500 to about 250,000, more preferably from about 500 to about 100,000. Examples of monomer repeat units that can be used in the preparation of hydrophobic blocks are set forth as follows.

1. Example Monomers Units Useful as Repeat Units in Hydrophobic Blocks or Hydrophobic Repeat Units Poly(2-vinylnaphthalene) Poly(caprolactam), R=H, $CH_3$, alkyl, or aryl group Polystyrene Poly(amide)

poly(p-X-styrene), X=alkyl, $CH_3$, t-Bu, O $CH_3$, $CH_2$ Cl, Cl, CN, CHO poly(alpha-methylstyrene)

poly(4-vinylpyridine) poly(2-vinylpyridine)

polybutadiene polybutadiene
 1,4-addition 1,2-addition polyisoprene polychloroprene polyethylene polypropylene polyvinylchloride polyvinylidenechloride polyvinylfluoride polyvinylidenefluoride polyhexafluoropropene polypropyleneoxide polypropyleneoxide poly(N-vinylcarbazol) polytetrafluoroethane polysiloxane polyacrylates R=$CH_3$, alkyl or aryl group R'=$CH_3$, any alkyl or aryl group
R'=$CH_3$, alkyl or aryl group R=$CH_3$, $CH_2$ $CH_3$, t-Butyl, any alkyl or aryl group Amino acids used to compose hydophobic blocks of the amphiphilic copolymer:

Alanine Valine

Leucine Tryptophan

Phenylalanine Methionine

Proline

2. Example Polymers Useful as Hydrophobic Blocks

Polymers as hydrophobic blocks of the nonionic copolymer (amphiphilic copolymer) for employment in the 'dangling chains' of the responsive microgel of the present invention also include, but are not limited to:

Poly[thio(2-chlorotrimethylene)thiotrimethylene], Poly[thio (1-iodiethylene)thio(5-bromo-3-chloropentamethylene), Poly[imino(1-oxoethylene)silylenetrimethylene], Poly (oxyiminomethylenehydrazomethylene), Poly[oxy(1,1-dichloroethylene)imino(1-oxoethylene)], Poly [(6-chloro-1-cyclohexen-1,3-ylene)-1-bromoethylene], Poly [(dimethylimino)ethylenebromide], Poly [(oxycarbonyloxymethyl)ethylene], Poly(1,1-dimethylethylene), Poly(1-methyl-butenylene), Poly[(2-propyl-1,3-dioxane-4,6-diyl) methylene], Poly[1-(methoxycarbonyl)ethylene], Poly(glycyl-6-aminocaproic acid), Poly(glycyl-6-aminocaproic acid-3-amino-propionic acid), Poly(L-alanyl-4-aminobutyric acid), Poly(L-alanyl-6-aminocaproic acid), Poly(L-alanyl-3-aminopropionic acid), Poly(L-alanyl-5-aminovaleric acid), Poly(2-aminocyclopentylenecarboxy acid), Poly(2-aminoethylenesulfonic acid), Poly(3-aminopropionic acid), Poly(1-methyl-3-aminopropionic acid), Poly [(3-aminocyclobutylene)-propionic acid], Poly[(2,2-dimethyl-3-aminocyclobutylene)-propionic acid], Poly(2-aminoisobutyric acid), Poly(3-aminobutyric acid), Poly(4-aminobutyric acid), Poly(5-aminovaleric acid), Poly(6-aminocaproic acid), Poly(D-(–)-3-methyl-6-aminocaproic acid), Poly(6-methyl-6-aminocaproic acid), Poly(6-aminothiocaproic acid), Poly(7-aminoenanthic acid), Poly((R)-3-methyl-7-aminoenanthic acid), Poly((S)-4-methyl-7-aminoenanthic acid), Poly((R)-5-methyl-7-aminoenanthic acid), Poly((R)-6-methyl-7-aminoenanthic acid), Poly(N-methyl-7-aminoenanthic acid), Poly(7-aminothioenanthic acid), Poly(8-aminocaprylic acid), Poly(9-aminopelargonic acid), Poly(10-aminocapric acid), Poly(11-aminoundecanoic acid), Poly(N-allyl-11-aminoundecanoic acid), Poly(N-ethyl-11-aminoundecanoic acid), Poly(2-methyl-11-aminoundecanoic acid), Poly(N-methyl-11-aminoundecanoic acid), Poly(N-phenyl-11-aminoundecanoic acid), Poly(N-piperazinyl-11-aminoundecanoic acid), Poly(12-aminolauric acid), Poly(aminoformic acid), Poly(N-butyl-aminoformic acid), Poly(2-methyl-N-butyl-aminoformic acid), Poly(N-phenyl-aminoformic acid), Poly[imino-(1-oxo-2,3-dimethyltrimethylene)], Poly[imino-(1-oxo-3-ethyltrimethylene)], Poly[imino-(1-oxo-4-methylhexamethylene)], Poly[imino-(1-oxo-3-methylhexamethylene)], Poly[imino-(1-oxo-5-methylhexamethylene)], Poly[imino-(1-oxo-3-methyl-6-isopropylhexam ethylene)], Poly[imino-(1-oxo-3-methyltrimethylene)], Poly[imino-(1-oxo-3-vinyltrimethylene)], Poly[N-(2-methylbutyl) iminocarbonyl], Poly[N-(phenylpropyl)iminocarbonyl], Poly(N-methyldodecane lactam), Poly(L-alanine), Poly(beta-L-alanine), Poly(N-methyl-L-alanine), Poly(L-phenylalanine), Poly(2-butyl-2-methyl-beta-alanine), Poly(2,2-dimethyl-beta-alanine), Poly(3,3-dimethyl-beta-alanine), Poly(2-ethyl-2-methyl-beta-alanine), Poly(2-methyl-2-propyl-beta-alanine), Poly(N-isopropyl-beta-alanine), Poly(3-methyl-beta-alanine), Poly(N-methyl-beta-alanine), Poly(N-phenyl-beta-alanine), Poly(mathacryloyl-D-alanine), Poly(M-methacryloyl-L-alanine), Poly(L-cysteine), Poly(L-glycine), Poly(L-leucine), Poly(isoleucine), Poly(N-trifluoroacetal-L-lysine), Poly(N-carbobenzoxy-L-lysine), Poly(methionine), Poly(L-tyrosine), Poly(o-acetal-hydroxyproline), Poly(o-acetal-L-serine), Poly(alpha-amino-n-butyric acid), Poly(s-carbobenzoxymethyl-L-cysteine), Poly(3,4-dihydro-L-proline), Poly(o-p-tolylsulfonyloxy-L-proline), Poly(gamma-hydroxy-o-acetyl-L-alpha-aminovaleric acid), Poly(L-valine), Poly(L-proline), Poly(L-proline), acid complex, Poly(L-proline), acetic acid complex, Poly(L-proline), formic acid complex, Poly(L-proline), propionic acid complex, Poly(o-acetyl-hydroxy-L-proline), Poly(o-acetyl-L-serine), Poly(o-benzyloxycarbonyl-L-tyrosine), Poly(s-benzyloxycarbonyl-L-cysteine), Poly(s-benzylthio-L-cysteine), Poly(methylphosphinidene-trimethylene), Polymalonate, Polysuccinate, Polyglutarate, Polyadipate, Poly(methylene), Poly(diphenylmethylene), Poly(di-p-tolyl-methylene), Poly(ethylene), Poly(chlorotrifluoroethylene), Poly(1-butoxy-2-methyl-ethylene), Poly(1-t-butoxy-2-methyl-ethylene), Poly(1-ethoxy-2-methoxyethylene), Poly(1-ethoxy-2-methyl-ethylene), Poly(1-isobutoxy-2-methyl-ethylene), Poly(1-isopropoxy-2-methyl-ethylene), Poly(1-methoxy-2-methyl-ethylene), Poly(1-methyl-2-propoxy-ethylene), Poly(tetrafluoroethylene), Poly(trifluoroethylene), Poly(butylethylene), Poly(t-butylethylene), Poly(cyclohexylethylene), Poly(2-cyclohexylethylene), Poly[(cyclohexylmethyl)ethylene], Poly(3-cyclohexylpropylethylene), Poly(decylethylene), Poly(dodecylethylene), Poly(isobutyl ethylene), Poly(neopentylethylene), Poly(4,4-dimethylpentylethylene), Poly(nonylethylene), Poly(octylethylene), Poly(propylethylene), Poly(propyl-2-propylene), Poly(tetradecylethylene), Poly(vinylbromide), Poly(N-vinyl carbazole), Poly(vinyl chloride), Poly(vinyl fluoride), Poly(vinylidene bromide), Poly(vinylidene chloride), Poly(vinylidene fluoride), Poly(vinylcyclobutane), Poly(vinylcycloheptane), Poly(vinylcyclohexane), Poly(o-methoxyvinylcyclohexane), Poly(3-methyl-vinylcyclohexane), Poly(4-methyl-vinylcyclohexane), Poly(vinylcyclohexene), Poly(vinylcyclohexylketone), Poly(vinylcyclopentane), Poly[3-(2-vinyl)-6-methyl pyridazinone], Poly[3-(2-vinyl)-6-methyl-4,5-pyridazinone], Poly(cyclopentylmethylethylene), Poly(heptylethylene), Poly(hexyldecylethylene), Poly(hexylethylene), Poly(cyclohexylethylene), Poly(cyclopentylethylene), Poly(cyclopropylethylene), Poly(isopentylethylene), Poly(isopropylethylene), Poly(3,3-dimethylbutylethylene), Poly(isohexylethylene), Poly(1,1-dimethylethylene), Poly(benzylethylene), Poly(N-carbazoylylethylene), Poly(ferrocenylethylene), Poly(indazol-2-ylethylene), Poly[dimethylamino(ethoxy)phosphinylethylene], Poly[dimethylamino(phenoxy)phosphinylethylene], Poly(4,4-dimethyl-oxazolonylethylene), Poly(4,4-dimethyl-oxazolonyl-2-propylene), Poly[(2-methyl-5-pyridyl) ethylene], Poly[(2-methyl-6-pyridyl)ethylene], Poly(2,4-dimethyl-1,3,5-triazinylethylene), Poly(1-naphthylethylene), Poly(2-naphthylethylene), Poly(phenethylethylene), Poly(phenethylmethylethylene), Poly(phenylacetylene), Poly(diphenylphosphinylethylene), Poly(phenylvinylene), Poly(phthalimidoethylene), Poly(2-pyridylethylene), Poly(4-pyridylethylene), Poly(N-pyrrolidinylethylene), Poly(m-tolylmethylethylene), Poly(o-tolylmethylethylene), Poly(p-tolylmethylethylene), Poly(vinyltrimethylgermanium), Poly(vinylcyclopropane), Poly(N-vinyldiphenylamine), Poly(1-vinylene-3-cyclopentylene), Poly(o-hydroxy-vinylphenylketone), Poly(3-vinyl pyrene), Poly(2-vinylpyridine), Poly(4-vinylpyridine), Poly(2-vinyl-5-methylpyridine), Poly(2-vinyl-5-ethylpyridine), Poly(1-cyano-2-phenylvlnylene), Poly(vinyl 3-trimethylsilylbenzoat), Poly(vinylfuran), Poly(vinylindole), Poly(2-vinyltetrahydrofuran), Poly(N-vinylphthalimide), Poly(1-vinylimidazlo), Poly(1-vinyl-2-methyl imidazole), Poly(5-vinyl-2-methylpyridine), Poly(1-vinylnaphthalene), Poly(2-vinylnaphthalene), Poly(5-vinyl-2-picoline), Poly(3-vinylpyrene), Poly(2-vinylpyridine), Poly(4-vinylpyridine), Poly(2-methyl-5-vinylpyridine), Poly(N-vinyl carbazole), Poly(1-vinyl naphthalene), Poly(styryl pyridine), Poly(N-vinyl succinimide), Poly(1,3-divinyl-imidazolid-2-one), Poly(1-ethyl- 3-vinyl-imidazolid-2-one), Poly(p-vinyl benzophenone), Poly(vinyl N,N-diethyl-carbamate), Poly(vinyl cymantrene), Poly[vinyl-tris(trimethoxysiloxy)silane], Poly(alpha-chlorovinyl triethoxysilane), Poly(p-vinylbenzylethylcarbinol), Poly(p-vinylbenzylmethylcarbinol), Poly(divinylaniline), Poly(vinylferrocene), Poly(9-vinylanthracene), Poly(vinylmercaptobenzimidazole), Poly(vinylmercaptobenzoxazole), Poly(vinylmercaptobenzothiazole), Poly(p-vinyl benzophenone), Poly(2-vinyl quinoline), Poly(vinylidene cyanide), Poly(1,2,5-trimethyl-vinylethylnyl-4-piperidinol), Poly(2-vinyl-1,1-dichlorocyclopropane), Poly(2-vinyl-2-methyl-4,4,6,6-tetraphenylcyclotrisiloxane), Poly(N-vinyl-N-methylacetamide), Poly(triethoxysilyl ethylene), Poly(trimethoxysilyl ethylene), Poly(1-acetoxy-1-cyanoethylene), Poly(1,1-dichloroethylene), Poly(1,1-dichloro-2-fluoroethylene), Poly(1,1-dichloro-2,2-difluoroethylene), Poly(1,2-dichloro-1,2-difluoroethylene), Poly[(pentafluoroethyl)ethylene], Poly(tetradecafluoropentylethylene), Poly(hexafluoropropylene), Poly(2,3,3,3-tetrafluoropropylene), Poly(3,3,3-trifluoropropylene), Poly[(heptafluoropropyl)ethylene], Poly(2-iodoethylethylene), Poly(9-iodononylethylene), Poly(3-iodopropyl-ethylene), Poly[(2-acetoxybenzoyloxy)ethylene], Poly(4-acetoxybenzoyloxyethylene), Poly[(1-acetylindazol-3-ylcarbonyloxy) ethylene], Poly(4-benzoylbutyryloxyethylene), Poly(3-bromobenzoyloxyethylene), Poly(4-bromobenzoyloxyethylene), Poly[(t-butoxycarbonylamino)ethylene], Poly(4-t-butylbenzoyloxyethylene), Poly(4-butyryloxybenzoyloxyethylene), Poly(2-chlorobenzoyloxyethylene), Poly(3-chlorobenzoyloxyethylene), Poly(4-chlorobenzoyloxyethylene), Poly(cyclohexanoyloxyethylene), Poly(cyclohexylacetoxyethylene), Poly(4-cyclohexylbutyryloxyethylene), Poly(cyclopentanoyloxyethylene), Poly(cyclopentylacetoxyethylene), Poly(4-ethoxybenzoyloxyethylene), Poly(4-ethylbenzoyloxyethylene), Poly[(2-ethyl-2,3,3-trimethylbutyryloxy)ethylene], Poly(trifluoroacetoxyethylene), Poly(heptafluorobutylryloxyethylene), Poly[(undecafluorodecanoyloxy)ethylene], Poly[(nonadecafluorodecanoyloxy)ethylene], Poly[(undecafluorohexanoyloxy)ethylene], Poly[(pentadecafluorooctanyloxy)ethylene], Poly[(pentafluoropropionyloxy)ethylene], Poly[(heptafluoroisopropoxy)ethylene], Poly(formyloxyethylene), Poly(isonicotinoyloxyethylene), Poly(4-isopropylbenzoyloxyethylene), Poly[(2-isopropyl-2,3-dimethylbutyryloxy)ethylene], Poly[(2-methoxybenzoyloxy)ethylene], Poly[(3-methoxybenzoyloxy)ethylene], Poly[(4-methoxybenzoyloxy)ethylene], Poly[(2-methylbenzoyloxy)ethylene], Poly[(3-methylbenzoyloxy)ethylene], Poly[(4-methylbenzoyloxy)ethylene], Poly[(1-methylcyclohexanoyloxy)ethylene], Poly(3,3-dimethyl-3-phenylpropionyloxyethylnene), Poly[(3-trimethylsilylbenzoyloxy)ethylene], Poly[(4-trimethylsilylbenzoyloxy)ethylene], Poly[(2,2-dimethylvaleryloxy)ethylene], Poly[(2,2,3,3-tetramethylvaleryloxy)ethylene], Poly[(2,2,3,4-tetramethylvaleryloxy)ethylene], Poly[(2,2,4,4-tetramethylvaleryloxy)ethylene], Poly(nicotinoyloxyethylene), Poly(nitratoethylene), Poly[(3-nitrobenzoyloxy)ethylene], Poly[(4-nitrobenzoyloxy)ethylene], Poly[(4-phenylbenzoyloxy)ethylene], Poly(pivaloyloxyethylene), Poly[(4-propionyloxybenzoyloxy)ethylene], Poly(propionyloxyethylene), Poly[(4-p-toluoylbutyryloxy)ethylene], Poly[(1,2-diethoxycarbonyl)ethylene], Poly[(1,2-dimethoxycarbonyl)ethylene], Poly[(1,2-dipropoxycarbonyl)ethylene], Poly(2-bromotetrafluoroethyliminotetrafuoroethylene), Poly[(biphenyl-4-yl)-ethylene], Poly(2-chloroethoxyethylene), Poly(hexadecyloxyethylene), Poly(isobutoxyethylene), Poly(1-methoxycarbonyl-1-phenylethylene), Poly(9-acrydinylethylene), Poly(4-methoxybenzylethylene), Poly[(3,6-dibromocarbazoyl)ethylene] Poly(propylene oxide) Poly(dimethylpentylsilylethylene), Poly(3,5-dimethylpyrozoylylethylene), Poly(2-diferrocenyl-furyl-methylene), Poly(ethoxyoxaloyloxymethyl ethylene), Poly(9-ethyl-3-carbazoyl ethylene), Poly(fluorenylethylene), Poly(imidazoethylene), Poly[(8-methoxycarbonyloctyl)ethylene], Poly(1-methoxy-4-naphthyl ethylene), Poly(2-methyl-5-pyridyl ethylene), Poly(propoxyoxaloyloxymethyl ethylene), Poly(1,1-diphenyl-2-vinylcyclopropane), Poly(p-anthrylphenylethylene), Poly[1-(N-ethyl-N-(1,4,7,10,13-pentaoxacyclopentadecyl)-carbamoyl)ethylene], Poly(N-carbazolylcarbonyl ethylene), Poly(morpholinocarbonyl ethylene), Poly(piperidinocarbonyl ethylene), Poly(N-benztriazolylethylene), Poly[6-(N-carbazoyl)hexyl ethylene], Poly(2,4-dimethyl-6-triazinylethylene), Poly(diphenylthiophosphinylideneethylene), Poly(2-methyl-5-pyridylethylene), Poly(N-thiopyrrolidonylethylene), Poly(N-1,2,4-triazolylethylene), Poly(phenothiazinyl ethylene), Poly(L-menthyloxycarbonylaminoethylene), Poly(N-3-methyl-2-pyrrolidone ethylene), Poly(p-vinyl-1,1-diphenyl ethylene), Poly(S-vinyl-O-ethylthioacetal formaldehyde), Poly(N-vinylphthalimide), Poly[N-(4-vinylphenyl)phthalimide], Poly[2-methyl-5-(4'-vinyl)phenyltetrazole], Poly[5-phenyl-2-(4'-vinyl)phenyltetrazole], Poly(N,N-methyl-vinyltoluenesulfonamide), Polyallene, Poly(1-butene), Poly(1-bromo-1-butene), Poly(1-butyl-1-butene), Poly(1-t-butyl-1-butene), Poly(1-chloro-1-butene), Poly(2-chloro-1,4,4-trifluoro-1-butene), Poly(1-decyl-1-butene), Poly(1-ethyl-butene), Poly(1,4,4-trifluoro-1-butene), Poly(octafluoro-1-butene), Poly(1-heptyl-1-butene), Poly(4-p-chlorophenyl-1-butene), Poly(4-p-methoxyphenyl-1-butene), Poly(4-cyclohexyl-1-butene), Poly(4-phenyl-1-butene), Poly(2-butene), Poly(isoprene), Poly(3-acetoxyisoprene), Poly(1-isopropyl-1-butene), Poly[3-(1-cyclohexenyl)isopropenyl acetate], Poly(4-methoxy-1-butene), Poly(4-methoxyyarbonyl-3-methyl-1-butene), Poly(1,2-dimethyl-butene), Poly(1-phenyl-butene), Poly(1-propyl-butene), Poly[(3-methyl)-1-butene)], Poly[(4-methyl)-1-butene)], Poly[(4-phenyl)-1-butene)], Poly[(4-cyclohexyl)-1-butene)], Poly[(4-N,N-diisopropylamino)-1-butene)], Poly[(3,3-dimethyl)-1-butene)], Poly[(3-phenyl)-1-butene)], Poly[(4-o-tolyl)-1-butene)], Poly[(4-p-tolyl)-1-butene)], Poly[(4,4,4-trifluoro)-1-butene)], Poly[(3-trifluoromethyl)-1-butene)], Poly[(4-trimethylsilyl)-1-butene], Poly(1,3,3-trimethylbutene), Poly(1,4-p-methoxyphenylbutene), Poly(1,4-p-chlorophenylbutene), Poly(1,4-cyclohexylbutene), Poly(1,4-phenylbutene), Poly(1,2-diethylbutene), Poly(2,2-dimethylbutene), Poly(1,3-cyclobutylene), Poly[(1-cyano)-1,3-cyclobutylene], Poly(N- butenyl carbazole), Poly(1-decene), Poly(1-docosene), Poly(dodecamethylene), Poly(1,2-chloro-dodecamethylene), Poly(1-methyl-dodecamethylene), Poly(1-dodecene), Poly(1-nonene), Poly(1-heptene), Poly(6,6-dimethyl-1-heptene), Poly(5-methyl-1-heptene), Poly (heptamethylene), Poly(1,2-dichloro-heptamethylene), Poly [(5-methyl)-1-heptene], Poly(1-hexadecene), Poly (1-hexene), Poly[(3-methyl)-1-hexene], Poly[(4-methyl)-1-hexene], Poly[(4,4-dimethyl)-1-hexene], Poly[(4-ethyl)-1-hexene], Poly[(5-methyl)-1-hexene], Poly(1,2-cyclohexalene), Poly(1,2-cyclopentylene-alt-ethylene), Poly(1,3-cyclopentylene-alt-methylene), Poly(isobutene), Poly(1-octadecene), Poly(octamethylene), Poly[(1-methyl)octamethylene], Poly(1-octene), Poly(6,6-dimethyl-4,8-dioxaspiro-1-octene), Poly(1-octadecene), Poly(1-pentene), Poly(cyclopentene), Poly(1,3-dione-4-cyclopentene), Poly(3,3-dimethoxy cyclopentene), Poly (1-pentadecene), Poly(5-amino-1-pentene), Poly(5-cyclohexyl-1-pentene), Poly [5-(N,N-dimethyl)amino-1-pentene], Poly[5-(N,N-diisobutyl)amino-1-pentene], Poly [5-(N,N-dipropyl)amino-1-pentene], Poly(4,4-dimethyl-1-pentene), Poly(3-methyl-1-pentene), Poly(3-ethyl-1-pentene), Poly(4-methyl-1-pentene), Poly(5,5,5-trifluoro-1-pentene), Poly(4-trifluoromethyl-1-pentene), Poly(5-trimethylsilyl-1-pentene), Poly(2-methyl-1-pentene), Poly(5-phenyl-1-pentene), Poly(1,2-cyclopentylene), Poly(3-chloro-1,2-cyclopentylene), Poly(pentamethylene), Poly(1,2-dichloropentamethylene), Poly(hexafluoroisobutylene), Poly(chloroprene), Poly(propene), Poly(3-cyclohexylpropene), Poly(3-cyclopentylpropene), Poly (hexafluoropropene), Poly(3-phenylpropane), Poly[3-(2',5'-dimethylphenyl)propene], Poly(3-(3',4'-dimethylphenyl)propene], Poly[3-(3',5'-dimethylphenyl) propene], Poly(3-silylpropene), Poly(3-p-tolylpropene), Poly(3-m-tolylpropene), Poly(3-o-tolylpropene), Poly(3-trimethylsilylpropene), Poly(3,3,3-trifluoropropene), Poly(3,3,3-trichloropropene), Poly(1-chloropropene), Poly(2-chloropropene), Poly(2,3-dichloropropene), Poly (3-chloro-2-chloromethylpropene), Poly(ethyl-2-propylene), Poly(1-nitropropylene), Poly(2-trimethylsilylpropene), Poly[1-(heptafluoroisopropoxy)methylpropylene], Poly[(1-heptafluoroisopropoxy)propylene], Poly(N-propenyl carbazole), Poly(propylidene), Poly(isopropenyltoluene), Poly(1-tridecene), Poly(1-tetradecene), Poly(vinylcyclobutane), Poly(vinylcycloheptane), Poly (vinylcyclohexane), Poly(vinylcyclopentane), Poly (vilnylcyclopropane), Poly(1-vinylene-3-cyclopentylene), Poly(octamethylene), Poly(1-methyloctamethylene), Poly(decamethylene), Poly(1,2-dichloro-decamethylene), Poly(2,5-pyrazinecyclobutylene), Poly(2,4-diphenyl-2,5-pyrazinecyclobutylene), Poly(1-undecene), Poly[(R)(–)-3,7-dimethyl-1-octene], Poly[(S)(+)-5-methyl-1-heptene], Poly[(S)(+)-4-methyl-1-hexene], Poly[(S)(+)-4-methyl-1-hexyne], Poly [(S)(+)-6-methyl-1-octene], Poly [(S)(+)-3-methyl-1-pentene], Poly[(R)-4-phenyl-1-hexene], Poly(dimethyl2,5-dicarboxylate-1-hexene), Poly [(S)-5-phenyl-1-heptene], Poly(1-ethyl-1-methyltetramethylene), Poly(1,1-dimethyltetramethylene), Poly(1,1-dimethyltrimethylene), Poly(1,1,2-trimethyltrimethylene), Poly(acryloylchloride), Poly (allylacrylate), Poly(allyl chloride), Poly(allylbenzene), Poly(diallyl phthalate), Poly(diallylcyanamide), Poly (acryloylpyrriolidone), Poly(allylcyclohexane), Poly(N-allylstearamide), Poly(allyl chloroacetate), Poly(allyl glycidyl phthalate), Poly(allylcyclohexane), Poly (allyltriethoxysilane), Poly(allylurea), Poly (allylbenzene), Poly(acetylene), Poly(beta-iodophenylacetylene), Poly(diacetylene), Poly(phenyl acetylene), Poly(3-methyl-1-pentyne), Poly(4-methyl-1-hexyne), Poly(5-methyl-1-heptyne), Poly(6-methyl-1-octyne), Poly(3,4-dimethyl-1-pentyne), Poly(2,3-dihydrofuran), Poly(N,N-dibutylacrylamide), Poly(N-docosylacrylamide), Poly(N-dodecylacrylamide), Poly (N-formylacrylamide), Poly(N-hexadecylacrylamide), Poly(N-octadecylacrylamide), Poly(N-octylacrylamide), Poly(N-phenylacrylamide), Poly(N-propylacrylamide), Poly(N-tetradecylacrylamide), Poly(N-butylacrylamide), Poly(N-sec-butylacrylamide), Poly(N-t-butylacrylamide), Poly(isodecylacrylamide), Poly(isohexylacrylamide), Poly(isononylacrylamide), Poly(isooctylacrylamide), Poly[N-(1,1-dimethyl-3-oxobutyl)acrylamide], Poly[1-oxy-(2,2,6,6-tetramethyl-4-piperidyl)acrylamide], Poly(N,N-dibutylacrylamide), Poly(N,N-diethylacrylamide), Poly(N,N-diisopropylacrylamide), Poly(N,N-diphenylacrylamide), Poly[N-(1,1-dimethyl-3-oxobutyl) acrylamide], Poly[N-(1-methylbutyl)acrylamide], Poly (N-methyl-N-phenylacrylamide), Poly(N-phenyl-N-1-naphthylacrylamide), Poly(N-phenyl-N-2-naphthylacrylamide), Poly(morpholylacrylamide), Poly (N-octadecylacrylamide), Poly(pipridylacrylamide), Poly (4-butoxycarbonylphenyl methacrylamide), Poly(N-t-butylmethacrylamide), Poly(N-benzyl methacrylamide), Poly(N-phenyl methacrylamide), Poly[N-(p-chlorophenyl)methacylamide], Poly[N-(p-methoxyphenyl)methacrylamide], Poly[N-(p-methylphenyl)methacrylamide], Poly[N-(p-nitrophenyl)methacrylamide], Poly[N-(p-stilbenyl)methacrylamide], Poly[N-(4'-nitro-p-stibenyl) methacrylamide], Poly(N-phenyl methacrylamide), Poly (1-deoxy-D-glucitol methacrylamide), Poly(4-carboxyphenylmethacrylamide), Poly(4-ethoxycarbonylphenylmethacrylamide), Poly(4-methoxycarbonylphenylmethacrylamide), Poly(N-allylmethacrylamide), Poly[1-(N-carbethoxyphenyl) methacrylamide], Poly(p-ethoxycarbonyl phenylmethacrylamide), Poly(carbethoxyphenyl methacrylamide), Poly(N-methyl-N-alpha-methylbenzyl-acrylamide), Poly(N-propyl-N-alpha-methylbenzyl-acrylamide), Poly(p-acrylamidomethylamino azobenzene), Poly(allyl acrylate), Poly(biphenyloxyhexamethylene acrylate), Poly(n-butylacrylate), Poly(2-nitrobutylacrylate), Poly(sec-butyl acrylate), Poly(t-butyl acrylate), Poly(p-carboxyphenyl acrylate), Poly(glycidyl acrylate), Poly(isobutyl acrylate), Poly(isopropyl acrylate), Poly (cresyl acrylate), Poly(decylacrylate), Poly(1,1-dihydroperfluoro-decylacrylate), Poly(docosylacrylate), Poly (dodecylacrylate), Poly(hexadecylacrylate), Poly (heptylacrylate), Poly(octadecylacrylate), Poly (octylacrylate), Poly(1,1-dihydroperfluorooctylacrylate), Poly(tetradecylacrylate), Poly(isopropyl acrylate), Poly (benzyl acrylate), Poly(4-biphenylyl acrylate), Poly(L-bornyl acrylate), Poly(4-butoxycarbonylphenyl acrylate), Poly(2-t-butylphenyl acrylate), Poly(4-t-butylphenyl acrylate), Poly[(1-chlorodifluoromethyl)tetrafuoroethyl acrylate], Poly[3-chloro-2,2-bis(chloromethyl)propyl acrylate], Poly(2-chlorophenyl acrylate), Poly(4-chlorophenyl acrylate), Poly(2,4-dichlorophenyl acrylate), Poly(pentachlorophenyl acrylate), Poly(4-cyanobenzyl acrylate), Poly(2-cyanobutyl acrylate), Poly(2-cyanoisobutyl acrylate), Poly(4-cyanobutyl acrylate), Poly (2-cyanoethyl acrylate), Poly(2-cyanoheptyl acrylate), Poly(2-cyanohexyl acrylate), Poly(cyanomethyl acrylate), Poly(2-cyanomethyl acrylate), Poly(5-cyano-3-oxapentyl acrylate), Poly(4-cyanophenyl acrylate), Poly(2- cyanoisopropyl acrylate), Poly(4-cyano-3-thiabutyl acrylate), Poly(6-cyano-3-thiahexyl acrylate), Poly(6-cyano-4-thiahexyl acrylate), Poly(8-cyano-7-thiaoctyl acrylate), Poly(5-cyano-3-thiapentyl acrylate), Poly(cyclododecyl acrylate), Poly(cyclohexyl acrylate), Poly(2-chloroethyl acrylate), Poly[di(chlorodifluoromethyl) fluoromethyl acrylate], Poly(2-ethoxycarbonylphenyl acrylate), Poly(3-ethoxycarbonylphenyl acrylate), Poly (4-ethoxycarbonylphenyl acrylate), Poly(2-ethoxyethyl acrylate), Poly(3-ethoxypropyl acrylate), Poly(ethyl acrylate), Poly(2-bromoethyl acrylate), Poly(2-ethylbutyl acrylate), Poly(2-ethylhexyl acrylate), Poly(ferrocenylethyl acrylate), Poly(ferrocenylmethyl acrylate), Poly(1H,1H-heptafluorobutyl acrylate), Poly(heptafluoroisopropyl acrylate), Poly[5-(heptafluroisopropoxy)pentyl acrylate], Poly[11-(heptafluoroisopropoxy)undecyl acrylate], Poly [2-(heptafluoropropoxy)ethyl acrylate], Poly[(2-(heptatluorobutoxy)ethyl acrylate], Poly[2-(1,1,2,2-tetrafluoroethoxy)ethyl acrylate], Poly(1H,1H,3H-hexafluorobutyl acrylate), Poly(2,2,2-trifluoroethyl acrylate), Poly[2,2-difluoro-2-(2-heptafluorotetrahydrofuranyl)ethyl acrylate], Poly(1H,1H-undecafluorohexyl acrylate), Poly(fluoromethyl acrylate), Poly(trifluoromethyl acrylate), Poly(1H,1H-pentadecafluorooctyl acrylate), Poly(5,5,6,6,7,7,7-heptafluoro-3-oxaheptyl acrylate), Poly(1H,1H-undecafluoro-4-oxaheptyl acrylate), Poly(1H,1H-nonafluoro-4-oxaheptyl acrylate), Poly(7,7,8,8-tetrafluoro-3,6-dioxaoctyl acrylate), Poly(1H,1H-tridecafluoro-4-oxaoctyl acrylate), Poly(2,2,3,3,5,5,5-heptafluoro-4-oxapentyl acrylate), Poly(4,4,5,5-tetrafluoro-3-oxapentyl acrylate), Poly(5,5,5-trifluoro-3-oxapentyl acrylate), Poly(1H,1H-nonafluoropentyl acrylate), Poly(nonafluoroisobutyl acrylate), Poly(1H,1H,5H-octafluoropentyl acrylate), Poly(heptafluoro-2-propyl acrylate), Poly[tetrafuoro-3-(heptafluoropropoxy)propyl acrylate], Poly[(tetrafluoro-3-(pentafluoroethoxy)propyl acrylate], Poly[tetrafluoro-3-(trifluoromethoxy)propyl acrylate], Poly(lH, 1H-pentafluoropropyl acrylate), Poly (octafluoropentyl acrylate), Poly(heptyl acrylate), Poly(2-heptyl acrylate), Poly(hexadecyl acrylate), Poly(hexyl acrylate), Poly(2-ethylhexyl acrylate), Poly(isobomyl acrylate), Poly(isobutyl acrylate), Poly(isopropyl acrylate), Poly(1,2:3,4-di-O-isopropylidene-alpha-D-galactopyranos-6-O-yl acrylate), Poly(3-methoxybutyl acrylate), Poly(2-methoxycarbonylphenyl acrylate), Poly(3-methoxycarbonylphenyl acrylate), Poly(4-methoxycarbonylphenyl acrylate), Poly(2-methoxyethyl acrylate), Poly (2-ethoxyethyl acrylate), Poly(4-methoxyphenyl acrylate), Poly(3-methoxypropyl acrylate), Poly(3,5-dimethyladamantyl acrylate), Poly(3-dimethylaminophenyl acrylate), Poly(2-methylbutyl acrylate), Poly(3-methylbutyl acrylate), Poly(1,3-dimethylbutyl acrylate), Poly(2-methyl-7-ethyl-4-undecyl acrylate), Poly(2-methylpentyl acrylate), Poly(menthyl acrylate), Poly(2-naphthyl acrylate), Poly(nonyl acrylate), Poly(octyl acrylate), Poly(2-octyl acrylate), Poly(3-pentyl acrylate), Poly(phenethyl acrylate), Poly(phenyl acrylate), Poly(2,4-dinitrophenyl acrylate), Poly(2,4,5-trichlorophenyl acrylate), Poly(2,4,6-tribromophenyl acrylate), Poly(3,4-epoxyhexahydrobenzyl acrylate), Poly[alpha-(o-ethyl methylphsphonoxy)-methyl acrylate], Poly(propyl acrylate), Poly(2,3-dibromopropyl acrylate), Poly(tetradecyl acrylate), Poly (3-thiabutyl acrylate), Poly(4-thiahexyl acrylate), Poly(5-thiahexyl acrylate, Poly(3-thispentyl acrylate), Poly(4-thiapentyl acrylate), Poly(m-tolyl acrylate), Poly(o-tolyl acrylate), Poly(p-tolyl acrylate), Poly(2-ethoxyethyl acrylate), Poly(3-ethoxypropyl acrylate), Poly(cholesteryl acrylate), Poly(2-ethyl-n-hexyl acrylate), Poly(1-oxy-2,2,6,6-tetramethyl-4-piperidyl acrylate), Poly(1,2,2,6,6-pentamethyl-4-piperidyl acrylate), Poly(4-phenylazoxyphenyl acrylate), Poly(ethyl cyanoacrylate), Poly[4-(10,15,20-triphenyl-21H,23H-5-yl)phenyl acrylate], Poly(1,1,5-trihydroperfluoroamyl acrylate), Poly(tributyltin acrylate), Poly(beta-ethoxyethyl acrylate), Poly(3,4-epoxyhexahydrobenzyl acrylate), Poly(alpha-chloroacrylnitrile), Poly(alpha-fluoroacrylnitrile), Poly(alpha-methoxy acrylnitrile), Poly(alpha-trifluoromethyl acrylnitrile), Poly(alpha-ethylacrylonitrile), Poly(alpha-isopropylacrylonitrile), Poly(alpha-propylacrylonitrile), Poly(amyl methacrylate), Poly[1-(3-cyanopropyl)acrylonitrile], Poly (t-butyl methacrylate), Poly(hexadecyl methacrylate), Poly(methyl methacrylate), Poly(cyanomethyl methacrylate), Poly(adamantyl methacrylate), Poly(3,5-dimethyladamantyl methacrylate), Poly(benzyl methacrylate), Poly(1-alpha-methylbenzyl methacrylate), Poly(2-bromoethyl methacrylate), Poly(2-t-butylaminoethyl methacrylate), Poly(butyl methacrylate), Poly(sec-butyl methacrylate), Poly(tert-butyl methacrylate), Poly(ethylbutyl methacrylate), Poly(4-phenylbutyl-1-methacrylate), Poly (2-phenylethyl-1-methacrylate), Poly(cetyl methacrylate), Poly(p-cetyloxybenzoyl methacrylate), Poly(2-chloroethyl methacrylate), Poly(cyanomethyl methacrylate), Poly(2-cyanoethyl methacrylate), Poly(4-cyanomethylphenyl methacrylate), Poly(4-cyanophenyl methacrylate), Poly(cyclohexyl methacrylate), Poly(p-t-butylcyclohexyl methacrylate), Poly(4-t-butylcyclohexyl methacrylate), Poly(cyclobutyl methacrylate), Poly(cyclobutylmethyl methacrylate), Poly(cyclododecyl methacrylate), Poly(2-cyclohexylethyl methacrylate), Poly(cyclohexylmethyl methacrylate), Poly(cyclopentyl methacrylate), Poly(cyclooctyl methacrylate), Poly(decyl methacrylate), Poly(n-decyl methacrylate), Poly(dodecyl methacrylate), Poly(n-decosyl methacrylate), Poly(diethylaminoethyl methacrylate), Poly(dimethylaminoethyl methacrylate), Poly(2-ethylhexyl methacrylate), Poly (ethyl methacrylate), Poly(acetoxyethyl methacrylate), Poly(2-methoxyethyl methacrylate), Poly(2-ethylsulfinylethyl methacrylate), Poly(ferrocenylethyl methacrylate), Poly(ferrocenylmethyl methacrylate), Poly(N-methyl-N-phenyl-2-aminoethyl methacrylate), Poly(2-N,N-dimethylcarbamoyloxyethyl methacrylate), Poly(2-acetoxy methacrylate), Poly(2-bromomethyl methacrylate), Poly(2-chloroethyl methacrylate), Poly(1H,1H-heptafluorobutyl methacrylate), Poly(1H,1H,7H-dodecafluoroheptyl methacrylate), Poly(1H,1H,9H-hexadecafluorononyl methacrylate), Poly(1H,1H,5H-octafluoropentyl methacrylate), Poly(1,1,1-trifluoro-2-propyl methacrylate), Poly(trifluoroisopropyl methacrylate), Poly(hexadecyl methacrylate), Poly(hexyl methacrylate), Poly(isobomyl methacrylate), Poly(isobutyl methacrylate), Poly(isopropyl methacrylate), Poly(1,2:3,4-di-O-isopropylidene-alpha-D-galactopyranos-6-O-yl methacrylate), Poly(2,3-O-isopropylidene-DL-glyceritol-1-O-yl methacrylate), Poly (nonyl methacrylate), Poly(methacrylic acid anhydride), Poly(4-methoxycarbonylphenyl methacrylate), Poly(3,5-dimethyladamantyl methacrylate), Poly(dimethylaminoethyl methacrylate), Poly(2-methylbutyl methacrylate), Poly(1,3-dimethylbutyl methacrylate), Poly(3,3-dimethylbutyl methacrylate), Poly(3,3-dimethyl-2-butyl methacrylate), Poly(3,5,5-trimethylhexyl methacrylate), Poly (trimethylsilyl methacrylate), Poly[(2-nitratoethyl) methacrylate], Poly(octadecyl methacrylate), Poly(octyl methacrylate), Poly(n-octadecyl methacrylate), Poly(3-oxabutyl methacrylate), Poly(pentyl methacrylate), Poly (neopentyl methacrylate), Poly(phenethyl methacrylate), Poly(phenyl methacrylate), Poly(2,6-diisopropylphenyl methacrylate), Poly(2,6-dimethylphenyl methacrylate), Poly(2,4-dinitrophenyl methacrylate), Poly(diphenylmethyl methacrylate), Poly(4-t-butylphenyl methacrylate), Poly(2-t-butylphenyl methacrylate), Poly(o-ethylphenyl methacrylate), Poly(p-ethylphenyl methacrylate), Poly (m-chlorophenyl methacrylate), Poly (m-nitrophenyl methacrylate), Poly(propyl methacrylate), Poly(tetradecyl methacrylate), Poly(butyl butoxycarbonyl methacrylate), Poly(tetradecyl methacrylate), Poly (ethylidene dimethacrylate), Poly(3,3,5-trimethylcyclohexyl methacrylate), Poly(2-nitro-2-methylpropyl methacrylate), Poly(triethylcarbinyl methacrylate), Poly(triphenylmethyl methacrylate), Poly(1,1-diethylpropyl methacrylate), Poly(ethyl glycolate methacrylate), Poly(3-methylcyclohexyl methacrylate), Poly(4-methylcyclohexyl methacrylate), Poly(2-methylcyclohexyl methacrylate), Poly(1-methylcyclohexyl methacrylate), Poly(bornyl methacrylate), Poly(tetrahydrofurfuryl methacrylate), Poly(vinyl methacrylate), Poly(2-chloroethyl methacrylate), Poly(2-diethylaminoethyl methacrylate), Poly(2-chlorocyclohexyl methacrylate), Poly(2-aminoethyl methacrylate), Poly(furfuryl methacrylate), Poly(methylmercaptyl methacrylate), Poly(2,3-epithiopropyl methacrylate), Poly(ferrocenylethyl methacrylate), Poly[2-(N,N-dimethylcarbamoyloxy)ethyl methacrylate], Poly (butyl butoxycarbonyl methacrylate), Poly(cyclohexyl chloroacrylate), Poly(ethyl chloroacrylate), Poly(ethyl ethoxycarbonyl methacrylate), Poly(ethyl ethacrylate), Poly(ethyl fluoromethacrylate), Poly(hexyl hexyloxycarbonyl methacrylate), Poly(1,1-dihydropentadecafluorooctyl methacrylate), Poly(heptafluoroisopropyl methacrylate), Poly(heptadecafluorooctyl methacrylate), Poly(1-hydrotetrafluoroethyl methacrylate), Poly(1,1-dihydrotetrafluoroisopropyl methacrylate), Poly(1-hydrohexafluorobutyl methacrylate), Poly(1-nonafluorobutyl methacrylate), Poly(1,3-dichloropropyl methacrylate), Poly[2-chloro-1-(chloromethyl)ethyl methacrylate], Poly(butylmercaptyl methacrylate), Poly (1-phenyl-n-amyl methacrylate), Poly[2-heptoxycarbonyl-1-heptoxycarbonylethylene)ethylene], Poly(2-t-butylphenyl methacrylate), Poly(4-cetyloxycarbonylphenyl methacrylate), Poly(1-phenylethyl methacrylate), Poly(p-methoxybenzyl methacrylate), Poly(1-phenylallyl methacrylate), Poly(p-cyclohexylphenyl methacrylate), Poly (2-phenylethyl methacrylate), Poly[1-(chlorophenyl) cyclohexyl methacrylate], Poly(1-phenylcyclohexyl methacrylate), Poly[2-(phenylsulfonyl)ethyl methacrylate], Poly(m-cresyl methacrylate), Poly(o-cresyl methacrylate), Poly(2,3-dibromopropyl methacrylate), Poly(1,2-diphenylethyl methacrylate), Poly(o-chlorobenzyl methacrylate), Poly(m-nitrobenzyl methacrylate), Poly(2-diphenyl methacrylate), Poly(4-diphenyl methacrylate), Poly(alpha-naphthyl methacrylate), Poly(beta-naphthyl methacrylate), Poly(alpha-naphthyl carbinyl methacrylate), Poly(2-ethoxyethyl methacrylate), Poly(lauryl methacrylate), Poly(pentabromophenyl methacrylate), Poly(o-bromobenzyl methacrylate), Poly(o-chlorodiphenylmethyl methacrylate), Poly(pentachlorophenyl methacrylate), Poly(2-diethylamino methacrylate), Poly(2-fluoroethyl mathacrylate), Poly(hexadecyl methacrylate), Poly(2-ethylbutyl methacrylate), Poly[4-(4-hexadecyloxy-benzoyloxy)phenyl methacrylate], Poly(D,L-diisobornyl methacrylate), Poly(decahydro-beta-naphthyl methacrylate), Poly(5-p-menthyl methacrylate), Poly(methyl butacrylate), Poly(methyl ethacrylate), Poly[(2-methylsulfinyl)ethylacrylate], Poly(methylphenylacrylate), Poly[4-(4-nonyloxy-benzoyloxy)-phenyl methacrylate], Poly(tetrahydrofurfuryl methacrylate), Poly[2-(triphenylmethoxy)ethyl methacrylate], Poly(cetyl methacrylate), Poly(2,3-epoxypropyl methacrylate), Poly(pentachlorophenyl methacrylate), Poly(pentafluorophenyl methacrylate), Poly[6-(anisyloxycarbonylphenoxy)hexyl methacrylate], Poly(ethyl-alpha-bromoacrylate), Poly[1-(2-N-cyclohexyl-N-methyl-carbamoyloxy)ethyl methacrylate], Poly[1-(2-N,N-diethylcarbamoyloxy)ethylmethacrylate], Poly[(2-N,N-diethylcarbamoyloxy)-2-methylethyl methacrylate], Poly(n-docosyl methacrylate), Poly(2,5-dimethylpyrozolylmethacrylate), Poly[11-(hexadecyl-dimethylammonio)-undecyl methacrylate], Poly[2-(4-methyl-1-piperazinylcarbonyloxy)ethyl methacrylate], Poly[(2-morpholino-carbonyloxy)ethylmethacrylate], Poly[1-(1-nonyloxy-4-phenoxycarbonyl) phenyl methacrylate], Poly(1,2,2,6,6-pentamethyl-4-piperidyl methacrylate), Poly(propionyloxyethyl methacrylate), Poly[3-(8-oxyl-7,7,9,9-tetramethyl-2,4-dioxo-1,3,8-triazaspiro(4,5)-dec-3-yl)propyl methacrylate], Poly(n-stearyl methacrylate), Poly[4-(1,1,3,3-tetramethylbutyl)phenyl methacrylate], Poly(o-tolyl methacrylate), Poly(p-tolyl methacrylate), Poly(2,4,5-trichlorophenyl methacrylate), Poly(n-tridecyl methacrylate), Poly(triphenylmethyl methacrylate), Poly(trityl methacrylate), Poly (tetrahydro-4H-pyranyl-2-methacrylate), Poly(tridecyl methacrylate), Poly[2-(triphenylmethoxy)ethyl methacrylate], Poly[2-(4-methyl-1-piperazinylcarbonyloxy)-2-methylethyl methacrylate], Poly(p-methoxyphenyl-oxycarbonyl-p-phenoxyhexamethylene methacrylate), Poly(diphenyl-2-pyridylmethyl methacrylate), Poly(diphenyl-4-pyridylmethyl methacrylate), Poly(triphenylmethyl methacrylate), Poly(hexyleneoxyphenylenecarboxyphenyleneoxymethylene methacrylate), Poly[4-(1,1,3,3-tetramethylbutyl)phenylmethacrylate], Poly(glycidyl methacrylate), Poly(2,2,6,6-tetramethyl-4-piperidinylmethacrylate), Poly[(2,2-dimethyl-1,3-dioxolane-4-yl) methyl methacrylate], Poly(alpha-alpha-dimethylbenzyl methacrylate), Poly(1,1-diphenylethyl methacrylate), Poly(2,3-epithiopropyl methacrylate), Poly(dicyclopentadienyltitanate dimethacrylate), Poly(diethylaminoethyl methacrylate), Poly(5-oxo-pyrrolidinylmethyl methacrylate), Poly(ethyl-alpha-bromoacrylate), Poly(isopropyl-alpha-bromoacrylate), Poly(methyl-alpha-bromoacrylate), Poly(n-pentyl-alpha-bromoacrylate), Poly(n-propyl-alpha-bromoacrylate), Poly(methyl alpha-trifluoromethylacrylate), Poly(phenyl alpha-bromoacrylate), Poly(sec-butyl-alpha-bromoacrylate), Poly(cyclohexyl-alpha-bromoacrylate), Poly(methyl-alpha-bromomethacrylate), Poly(butyl chloroacrylate), Poly(sec-butyl chloroacrylate), Poly(methyl chloroacrylate), Poly(isobutyl chloroacrylate), Poly(isopropyl chloroacrylate), Poly(cyclohexyl chloroacrylate), Poly(2-chloroethyl chloroacrylate), Poly[1-methoxycarbonyl-1-methoxycarbonylmethylene)ethylene], Poly(methyl chloroacrylate), Poly(ethyl alpha-chloroacrylate), Poly (methyl beta-chloroacrylate), Poly(cyclohexyl alpha-ethoxyacrylate), Poly(methyl fluoroacrylate), Poly(methyl fluoromethacrylate), Poly(methyl phenylacrylate), Poly(propyl chloroacrylate), Poly(methyl cyanoacrylate), Poly(ethyl cyanoacrylate), Poly(butylcyanoacrylate), Poly(sec-butyl thiolacrylate), Poly(isobutyl thiolacrylate), Poly (ethyl thioacrylate), Poly(methyl thioacrylate), Poly (butyl thioacrylate), Poly(isopropyl thiolacrylate), Poly (propyl thiolacrylate), Poly(phenyl thiomethacrylate), Poly(cyclohexyl thiomethacrylate), Poly(o-methylphenylthio methacrylate), Poly(nonyloxy-1,4-phenyleneoxycarbonylphenyl methacrylate), Poly(4-methyl-2-N,N-dimethylaminopentyl methacrylate), Poly[alpha-(4-chlorobenzyl)ethyl acrylate], Poly[alpha-(4-cyanobenzyl) ethyl acrylate], Poly[alpha-(4-methoxybenzyl)ethyl acrylate], Poly(alpha-acetoxy ethyl acrylate), Poly(ethyl alpha-benzylacrylate), Poly(methyl alpha-benzylacrylate), Poly(methyl alpha-hexylacrylate), Poly(ethyl alpha-fluoroacrylate), Poly(methyl alpha-fluoroacrylate), Poly(methyl alpha-isobutylacrylate), Poly(methyl alpha-isopropylacrylate), Poly(methyl alpha-methoxyacrylate), Poly(butyl alpha-phenylacrylate), Poly(chloroethyl alpha-phenylacrylate), Poly(methyl alpha-phenylacrylate), Poly(propyl alpha-phenylacrylate), Poly(methyl alpha-propylacrylate), Poly(methyl alpha-sec-butylacrylate), Poly(methyl alpha-trifluoromethylacrylate), Poly(ethyl alpha-acetoxyacrylate), Poly(ethyl beta-ethoxyacrylate), Poly(methacryloyl chloride), Poly(methacryloylactone), Poly(methylenebutyrolactone), Poly(acryloylpyrrolidone), Poly[butyl N-(4-carbethoxyphenyl)itaconamate], Poly[ethyl N-(4-carbethoxyphenyl)itaconamate], Poly[methyl N-(4-carbethoxyphenyl)itaconamate], Poly[propyl N-(4-carbethoxyphenyl)itaconamate], Poly[ethyl N-(4-chlorophenyl)itaconamate], Poly[methyl N-(4-chlorophenyl)itaconamate], Poly[propyl N-(4-chlorophenyl)itaconamate], Poly[butyl N-(4-methoxyphenyl)itaconamate], Poly[ethyl N-(4-methoxyphenyl)itaconamate], Poly[methyl N-(4-methoxyphenyl)itaconamate], Poly[propyl N-(4-methoxyphenyl)itaconamate], Poly[butyl N-(4-methylphenyl)itaconamate], Poly[ethyl N-(4-methylphenyl)itaconamate], Poly[methyl N-(4-methylphenyl)itaconamate], Poly[propyl N-(4-methylphenyl)itaconamate], Poly[butyl N-phenyl itaconamate], Poly[ethyl N-phenyl itaconamate], Poly[methyl N-phenyl itaconamate], Poly[propyl N-phenyl itaconamate], Poly(diamyl itaconate), Poly(dibutyl itaconate), Poly(diethyl itaconate), Poly(dioctyl itaconate), Poly(dipropyl itaconate), Polystyrene, Poly[(p-t-butyl)-styrene], Poly[(o-fluoro)-styrene], Poly[(p-fluoro)-styrene], Poly[(alpha-methyl)-styrene], Poly[(alpha-methyl)(p-methyl)-styrene], Poly[(m-methyl)-styrene], Poly[(o-methyl)-styrene], Poly[(o-methyl)(p-fluoro)-styrene], Poly[(p-methyl)-styrene], Poly(trimethylsilylstyrene), Poly(beta-nitrostyrene), Poly(4-acetylstyrene), Poly(4-acetoxystyrene), Poly(4-p-anisoylstyrene), Poly(4-benzoylstyrene), Poly[(2-benzoyloxymethyl)styrene], Poly[(3-(4-biphenylyl)styrene], Poly[(4-(4-biphenylyl)styrene], Poly(5-bromo-2-butoxystyrene), Poly(5-bromo-2-ethoxystyrene), Poly(5-bromo-2-isopentyloxystyrene), Poly(5-bromo-2-isopropoxystyrene), Poly(4-bromostyrene), Poly(2-butoxycarbonylstyrene), Poly(4-butoxycarbonylstyrene), Poly(4-[(2-butoxyethoxy)methyl]styrene), Poly(2-butoxymethylstyrene), Poly(4-butoxymethylstyrene), Poly[4-(sec-butoxymethyl)styrene], Poly(4-butoxystyrene), Poly(5-t-butyl-2-methylstyrene), Poly(4-butylstyrene), Poly(4-sec-butylstyrene), Poly(4-t-butylstyrene), Poly(4-butyrylstyrene), Poly(4-chloro-3-fluorostyrene), Poly(4-chloro-2-methylstyrene), Poly(4-chloro-3-methylstyrene), Poly(2-chlorostyrene), Poly(3-chlorostyrene), Poly(4-chlorostyrene), Poly(2,4-dichlorostyrene), Poly(2,5-dichlorostyrene), Poly(2,6-dichlorostyrene), Poly(3,4-dichlorostyrene), Poly(2-bromo-4-trifluoromethylstyrene), Poly(4-cyanostyrene), Poly(4-decylstyrene), Poly(4-dodecylstyrene), Poly(2-ethoxycarbonylstyrene), Poly(4-ethoxycarbonylstyrene), Poly[4-(2-ethoxymethyl)styrene], Poly(2-ethoxymethylstyrene), Poly(4-ethoxystyrene), Poly[4-(2-diethylaminoethoxycarbonyl)styrene], Poly(4-diethylcarbamoylstyrene), Poly[4-(1-ethylhexyloxymethyl)styrene], Poly(2-ethylstyrene), Poly(3-ethylstyrene), Poly(4-ethylstyrene), Poly[4-(pentadecafluoroheptyl)styrene], Poly(2-fluoro-5-methylstyrene), Poly(4-fluorostyrene), Poly(3-fluorostyrene), Poly(4-fluoro-2-trifluoromethyl styrene), Poly(p-fluoromethyl styrene), Poly(2,5-difluorostyrene), Poly(2,3,4,5,6,-pentafluorostyrene), Poly(perfluorostyrene), Poly(alpha,beta,beta-trifluorostyrene), Poly(4-hexadecylstyrene), Poly(4-hexanoylstyrene), Poly(2-hexyloxycarbonylstyrene), Poly(4-hexyloxycarbonylstyrene), Poly(4-hexyloxymethylstyrene), Poly(4-hexylstyrene), Poly(4-iodostyrene), Poly(2-isobutoxycarbonylstyrene), Poly(4-isobutoxycarbonylstyrene), Poly(2-isopentyloxycarbonylstyrene), Poly(2-isopentyloxymethylstyrene), Poly(4-isopentyloxystyrene), Poly(2-isopropoxycarbonylstyrene), Poly(4-isopropoxycarbonylstyrene), Poly(2-isopropoxymethylstyrene), Poly(4-isopropylstyrene), Poly(4-isopropyl-alpha-methylstyrene), Poly(4-trimethylsilyl-alpha-methylstyrene), Poly(2,4-diisopropylstyrene), Poly(2,5-diisopropylstyrene), Poly(beta-methylstyrene), Poly(2-methoxymethylstyrene), Poly(2-methoxycarbonylstyrene), Poly(4-methoxycarbonylstyrene), Poly(4-methoxymethylstyrene), Poly(4-methoxy-2-methylstyrene), Poly(2-methoxystyrene), Poly(4-methoxystyrene), Poly(4-N,N-dimethylamino styrene), Poly(2-methylaminocarbonylstyrene), Poly(2-dimethylaminocarbonylstyrene), Poly(4-dimethylaminocarbonylstyrene), Poly[2-(2-dimethylaminoethoxycarbonyl)styrene], Poly[4-(2-dimethylaminoethoxycarbonyl)styrene], Poly(2-methylstyrene), Poly (3-methylstyrene), Poly(4-methylstyrene), Poly(4-methoxystyrene), Poly(2,4-dimethylstyrene), Poly(2,5-dimethylstyrene), Poly(3,4-dimethylstyrene), Poly(3,5-dimethylstyrene), Poly(2,4,5-trimethylstyrene), Poly(2,4,6-trimethylstyrene), Poly(3-[bis(trimethylsiloxy)boryl]styrene), Poly(4-[bis(trimethylsiloxy)boryl]styrene), Poly(4-morpholinocarbonylstyrene), Poly[4-(3-morpholinopropionyl)styrene], Poly(4-nonadecylstyrene), Poly(4-nonylstyrene), Poly(4-octadecylstyrene), Poly(4-octanoylstyrene), Poly[4-(octyloxymethyl)styrene], Poly(2-octyloxystyrene), Poly(4-octyloxystyrene), Poly(2-pentyloxycarbonylstyrene), Poly(2-pentyloxymethylstyrene), Poly(2-phenethyloxymethylstyrene), Poly(2-phenoxycarbonylstyrene), Poly(4-phenoxystyrene), Poly(4-phenylacetylstyrene), Poly(2-phenylaminocarbonylstyrene), Poly(4-phenylstyrene), Poly(4-piperidinocarbonylstyrene), Poly[4-(3-piperidinopropionyl)styrene], Poly(4-propionylstyrene), Poly(2-propoxycarbonylstyrene), Poly(4-propoxycarbonylstyrene), Poly(2-propoxymethylstyrene), Poly(4-propoxymethylstyrene), Poly(4-propoxystyrene), Poly(4-propoxysulfonylstyrene), Poly(4-tetradecylstyrene), Poly(4-p-toluoylstyrene), Poly(4-trimethylsilylstyrene), Poly[2-(2-thio-3-methylpentyl)styrene], Poly[9-(2-methylbutyl)-2-vinyl carbazole], Poly[9-(2-methylbutyl)-3-vinyl carbazole], Poly(3-sec-butyl-9-vinyl carbazole), Polylp-(p-tolylsulfinyl)styrene], Poly(4-valerylstyrene), Poly[(4-t-butyl-dimethylsilyl)oxy styrene], Poly(4-isopropyl-2-methyl styrene), Poly[1-(4-formylphenyl)ethylene], Poly(alpha-methoxystyrene), Poly(alpha-methylstyrene), Poly(p-octylamine sulfonate styrene), Poly(m-divinylbenzene), Poly(p-divinylbenzene), Polybutadiene (1,4-addition), Polybutadiene (1,2-addition), (2-t-butyl)-cis-1,4-poly-1,3-butadiene, (2-chloro)-trans-1,4-poly-1,3-butadiene, (2-chloro)-cis-1,4-poly-1,3-butadiene, (1-cyano)-trans-1,4-poly-1,3-butadiene, (1-methoxy)-trans-1,4-poly-1,3-butadiene, (2,3-dichloro)-trans-1,4-poly-1,3-butadiene, (2,3-dimethyl)-trans-1,4-poly-1,3-butadiene, (2,3-dimethyl)-cis-1,4-poly-1,3-butadiene, (2-methyl)-cis-1,4-poly-1,3-butadiene, (2-methyl)-trans-1,4-poly-1,3-butadiene, (2-methyl-3-chloro)-trans-1,4-poly-1,3-butadiene, (2-methylacetoxy)-trans-1,4-poly-1,3-butadiene, (2-propyl)-trans-1,4-poly-1,3-butadiene, Poly(2-decyl-1,3-butadiene), Poly(2-heptyl-1,3-butadiene), Poly(2-isopropyl-1,3-butadiene), Poly(2-t-butyl-1,3-butadiene), [1,4-(4,4'-diphenyleneglutarate)]-1,4-poly-1,3-butadiene, Poly(2-chloromethyl-1,3-butadiene), Poly(ethyl-1-carboxylate-1,3-butadiene), Poly(1-diethylamino-1,3-butadiene), Poly(diethyl 1,4-carboxylate-1,3-butadiene), Poly[1-acetoxy-1,3-butadiene), Poly(1-ethoxy-1,3-butadiene), Poly(2-phthalidomethyl-1,3-butadiene), Poly(2,3-bis(diethylphosphono-1,3-butadiene), Poly(hexafluoro-1,3-butadiene), Poly(2-fluoro-1,3-butadiene), Poly(1-phthalimido-1,3-butadiene), Poly(1,4-poly-1,3-cyclohexalene), 1,12-poly-1,11-dodecadiyne, 1,2-poly-1,3-pentadiene, (4-methyl)-1,2-poly-1,4-pentadiene, Poly(perfluoro-1,4-pentadiene), Poly(1-ferrocenyl-1,3-butadiene), Poly(perfluorobutadiene), Poly(1-phenyl butadiene), Poly(spiro-2,4-hepta-4,6-diene), Poly(1,1,2-trichlorobutadiene), Poly(1,3-pentadiene), 1,4-poly-1,3-heptadiene, (6-methyl)-trans-1,4-poly-1,3-heptadiene, (5-methyl)-trans-1,4-poly-1,3-heptadiene, (3,5-dimethyl)-1,4-poly-1,3-heptadiene, (6-phenyl)-1,4-poly-1,3-heptadiene, 1,4-poly-trans-1,3-hexadiene, (5-methyl)-trans-1,4-poly-1,3-hexadiene, (5-phenyl)-trans-1,4-poly-1,3-hexadiene, trans-2,5-poly-2,4-hexadiene, (2,5-dimethyl)-trans-2,5-poly-2,4-hexadiene, Poly(1,5-hexadiene), 1,4-poly-1,3-octadiene, 1,4-poly-chloroprene, 1,4-poly-isoprene, Poly(hexatriene), Poly(trichlorohexatriene), 2,5-poly-2,4-hexadienoic acid, diisopropyl ester, 2,5-poly-2,4-hexadienoic acid, butyl ester, 2,5-poly-2,4-hexadienoic acid, ethyl ester, 2,5-poly-2,4-hexadienoic acid, isoamyl ester, 2,5-poly-2,4-hexadienoic acid, isobutyl ester, 2,5-poly-2,4-hexadienoic acid, isopropyl ester, 2,5-poly-2,4-hexadienoic acid, methyl ester, 2,5-poly-2,4-hexadiyne, [1,6-di(N-carbazoyl))-2,5-poly-2,4-hexadiyne, 1,9-poly-1,8-nonadiyne, 1,4-poly-1,3-octadene, 1,2-poly-1,3-pentadiene, (4-methyl)-1,2-poly-1,3-pentadiene, 1,4-poly-1,3-pentadiene, (2-methyl)-1,4-poly-1,3-pentadiene 2,5-poly-5-phenyl-2,4-pentadienoic acid, butyl ester, 2,5-poly-5-phenyl-2,4-pentadienoic acid, methyl ester, Poly(4-trans-4-ethoxy-2,4-pentadienoate), Poly(trans-4-ethoxy-2,4-pentadienonitrile), 1,24-poly-1,11,13,23-tetracisatetrayne, Poly(3-hydroxybutyricacid), Poly(10-hydroxycapricacid), Poly(3-hydroxy-3-trichloromethyl-propionic acid), Poly(2-hydroxyacetic acid), Poly(dimethyl-2-hydroxyacetic acid), Poly(diethyl-2-hydroxyacetic acid), Poly(isopropyl-2-hydroxyacetic acid), Poly(3-hydroxy-3-butenoic acid), Poly(6-hydroxycarproic acid), Poly(5-hydroxy-2-(1,3-dioxane)-carprylic acid], Poly(7-hydroxynanthic acid), Poly[(4-methyl)-7-hydroxynanthic acid], Poly[4-hydroxymethylene-2-(1,3-dioxane)-carprylic acid], Poly(5-hydroxy-3-oxavaleric acid), Poly(2,3,4-trimethoxy-5-hydroxyvaleric acid), Poly(2-hydroxypropionic acid), Poly(3-hydroxypropionic acid), Poly(2,2-bischloromethyl-3-hydroxypropionic acid), Poly(3-chloromethyl-3-hydroxypropionic acid), Poly(2,2-butyl-3-hydroxypropionic acid), Poly(3-dichloromethyl-3-hydroxypropionic acid), Poly(2,2-diethyl-3-hydroxypropionic acid), Poly(2,2-dimethyl-3-hydroxypropionic acid), Poly(3-ethyl-3-hydroxypropionic acid), Poly(2-ethyl-2-methyl-3-hydroxypropionic acid), Poly(2-ethyl-2-methyl-1,1-dichloro-3-hydroxypropionic acid), Poly(3-isopropyl-3-hydroxypropionic acid), Poly(2-methyl-3-hydroxypropionic acid), Poly(3-methyl-3-hydroxypropionic acid), Poly(2-methyl-2-propyl-3-hydroxypropionic acid), Poly(3-trichloromethyl-3-hydroxypropionic acid), Poly(carbonoxide-alt-ethylene), Poly(oxycarbonyl-1,5-dimethylpentamethylene), Poly(oxycarbonylethylidene), Poly(oxycarbonylisobutylidene), Poly(oxycarbonylisopentylidene), Poly(oxycarbonylpentamethylene), Poly(oxycrabonyl-3-methylhexamethylene), Poly(oxycarbonyl-2-methylpentamethylene), Poly(oxycarbonyl-3-methylpentamethylene), Poly(oxycarbonyl-4-methylpentamethylene), Poly(oxycarbonyl-1,2,3-trimethyloxytetramethylene), Poly(2-mercaptocarproic acid), Poly(4-methyl-2-mercaptocarproic acid), Poly(2-mercaptoacetic acid), Poly(2-methyl-2-mercaptoacetic acid), Poly(3-mercaptopropionoic acid), Poly(2-phthalimido-3-mercaptopropionoic acid), Poly[2-(p-toluenesulfonamido)-3-mercaptopropionic acid], Poly(thiodipropionic anhydride), Poly(ethyl alpha-cyanocinnamate), Poly(cinnamonitrile), Poly(alpha-cyanocinnamonitrile), Poly(N-methyl citraconimide), Poly(methyl alpha-acetyl crotonate), Poly(ethyl alpha-carbethoxy crotonate), Poly(ethyl alpha-chlorocrotonate), Poly(ethyl alpha-cyanocrotonate), Poly(methyl alpha-methoxycrotonate), Poly(methyl alpha-methylcrotonate), Poly(ethylcrotonate), Poly(diethyl fumarate), Poly(vinyl acetalacetate), Poly(vinyl chloroacetate), Poly(vinyl dichloroacetate), Poly(vinyl trichloroacetate), Poly(trifluorovinyl acetate), Poly(propenyl acetate), Poly(2-chloropropenyl acetate), Poly(2-methylpropenyl acetate), Poly(vinyl chloroacetate), Poly(vinyl benzoate), Poly(p-t-butylvinyl benzoate), Poly(vinyl 4-chlorobenzoate), Poly(vinyl 3-trimethylsilylbenzoate), Poly(vinyl4-trimethylsilylbenzoate), Poly(p-acryloyloxyphenyl benzoate), Poly(vinyl butyrate), Poly(vinyl 1,2-phenylbutyrate), Poly(vinyl caproate), Poly(vinyl cinnamate), Poly(vinyl decanoate), Poly(vinyl dodecanoate), Poly(vinylformate), Poly(methyl allyl fumarate), Poly(vinyl hexanoate), Poly(vinyl 2-ethylhexanoate), Poly(vinyl hexadeconoate), Poly(vinyl isobutyrate), Poly(vinyl isocaproate), Poly(vinyl laurate), Poly(vinyl myristate), Poly(vinyl octanoate), Poly(methyl allyl oxalate), Poly(octyl allyl oxalate), Poly(1-vinyl-palmitate), Poly(t-butyl-4-vinyl perbenzoate), Poly(vinyl propionoate), Poly(vinyl pivalate), Poly(vinyl stearate), Poly(2-chloropropenyl acetate), Poly(vinyl hendecanoate), Poly(vinyl thioacetate), Poly(vinylhydroquinone dibenzoate), Poly(vinyl isocyanate), Poly(N-vinyl-ethyl carbamate), Poly(N-vinyl-t-butyl carbamate), Poly(N,N-diethyl vinyl carbamate), Poly(2-chloro-propenyl acetate), Poly(vinylhydroquinone dibenzoate), Poly(ethyl trans-4-ethoxy-2,4-pentadienoate), Poly(triallyl citrate), Poly(vinyl 12-ketostearate), Poly(vinyl 2-ethylhexanoate), Poly(vinylene carbonate), Poly(divinyl adipate), Poly(vinyl hexadecanoate), Poly(vinyl pelargonate), Poly(vinyl thioisocyanate), Poly(vinyl valerate), Poly(diallyl-beta-cyanoethylisocyanurate), Poly(diallylcyanamide), Poly(triallyl citrate), Poly(triallyl cyanurate), Poly(triallyl isocyanurate), Poly[3-(1-cyclohexenyl)isopropenyl acetate), Poly(isopropenyl acetate), Poly(isopropenylisocyanate), Poly(vinyl diethyl phosphate), Poly(allyl acetate), Poly(vinyl phenylisocyanate), Poly(benzylvinylether), Poly(butylvinylether), Poly(2-methylbutylvinylether), Poly(sec-butylvinylether), Poly(1-methyl-sec-butylvinylether), Poly(t-butylvinylether), Poly(butylthioethylene), Poly(1-butoxy-2-chloroethylene),cis, Poly(1-butoxy-2-chloroethylene),trans, Poly(1-chloro-2-isobutoxyethylene),trans, Poly(1-isobutoxy-2-methylethylene),trans, Poly(ethylvinyl ether), Poly(2-chloroethylvinyl ether), Poly(2-bromoethylvinyl ether), Poly(vinylbutyl sulfonate), Poly(2-methoxyethylvinyl ether), Poly(2,2,2-trifluoroethylvinyl ether), Poly(isobutylvinylether), Poly(isopropylvinylether), Poly(methylvinylether), Poly(octylvinyl ether), Poly(alpha-methylvinylether), Poly(n-pentylvinylether), Poly(propylvinylether), Poly(l-methylpropylvinylether), Poly(decylvinyl ether), Poly(dodecylvinylether), Poly(isobutylpropenyl ether), Poly(cyclohexyloxyethylene), Poly(hexadecyloxyethylene), Poly(octadecyloxyethylene), Poly(1-bomyloxyethylene), Poly(1-cholesteryloxyethylene), Poly(1,2–5,6-diisopropylidene-alpha-D-glucofuranosyl-3-oxyethylene), Poly(1-menthyloxyethylene), Poly(1-alpha-methylbenzyloxyethylene), Poly[3-beta-(styryloxy)methane], Poly(2-phenylvinyl 2-methylbutyl ether), Poly(2-phenylvinyl 3-methylpentyl ether), Poly[(2-ethylhexyloxy)ethylene], Poly(ethylthioethylene), Poly(dodecafluorobutoxy ethylene), Poly(2,2,2-trifluoroethoxytrifluoroethylene), Poly[1,1-bis(trifluoromethoxy)difluoroethylene], Poly(1,1-difluoro-2-trifluoromethoxymethylene), Poly(1,2-difluoro-1-trifluoromethoxymethylene), Poly(hexafluoromethoxyethylene), Poly[(heptafluoro-2-propoxy)ethylene], Poly(hexyloxyethylene), Poly(isobutoxyethylene), Poly(isopropenyl methyl ether), Poly(isopropoxyethylene), Poly(methoxy ethylene), Poly(2-methoxypropylene), Poly(2,2-dimethylbutoxyethylene), Poly(methylthioethylene), Poly(neopentyloxyethylene), Poly(octyloxyethylene), Poly(pentyloxyethylene), Poly(propoxyethylene), Poly(1-acetyl-1-fluoroethylene), Poly(4-bromo-3-methoxybenzoylethylene), Poly(4-t-butylbenzoylethylene), Poly(4-chlorobenzoylethylene), Poly(4-ethylbenzoylethylene), Poly(4-isopropylbenzoylethylene), Poly(4-methoxybenzoylethylene), Poly(3,4-dimethylbenzoylethylene), Poly(4-propylbenzoylethylene), Poly(p-toluoylethylene), Poly(vinyl isobutyl sulfide), Poly(vinyl methyl sulfide), Poly(vinyl phenyl sulfide), Poly(vinyl ethyl sulfoxide), Poly(vinyl ethyl sulfide), Poly(t-butyl vinyl ketone), Poly(isopropenyl methyl ketone), Poly(methyl vinyl ketone), Poly(phenyl vinyl ketone), Poly(2-methylbutyl vinyl ketone), Poly(3-methylpentyl vinyl ketone), Poly(isopropenylisocyanate), Poly(vinyl chloromethyl ketone), Poly(vinyl 2-chlorocyclohexyl ketone), Poly(vinyl 4-chlorocyclohexyl ketone), Poly(2-chloroacetaldehyde), Poly(2,2-dichloroacetaldehyde), Poly(2,2,2-trichloroacetaldehyde), Poly(2-butene oxide), Poly(2-methyl-2-butene oxide), Poly(butadiene oxide), Poly(butyraldehyde), Poly(crotonaldehyde), Poly(valeraldehyde), Poly(1,3-cyclobutyleneoxymethylene oxide), Poly[(2,2,4,4-tetramethyl)-1,3-cyclobutyleneoxymethylene oxide], Poly(decamethylene oxide), Poly(dodecamethylene oxide), Poly(ethylenetrimethyleneoxide), Poly(1,1-bischloromethyl-ethyleneoxide), Poly(bromomethyl-ethylene oxide), Poly(t-butyl-ethylene oxide), Poly(chloromethyl-ethylene oxide), Poly(1,2-dichloromethyl-ethylene oxide), Poly(1-fluoroethylene oxide), Poly(isopropyl-ethylene oxide), Poly(neopentyl-ethylene oxide), Poly(tetrafluoro-ethylene oxide), Poly(tetramethyl-ethylene oxide), Poly(ethyleneoxymethylene oxide), Poly(heptaldehyde), Poly(hexamethylene oxide), Poly(hexamethyleneoxymethylene oxide), Poly(isobutylene oxide), Poly(isobutyraldehyde), Poly(isophthalaldehyde), Poly(isopropylidene oxide), Poly(isovaleraldehyde), Poly(methyleneoxypentamethylene oxide), Poly(methyleneoxytetramethylene oxide), Poly(methyleneoxynonamethylene oxide), Poly(methyleneoxyoctamethylene oxide), Poly(methyleneoxytetradecamethylene oxide), Poly(nonaldehyde), Poly(decamethylene oxide), Poly(nonamethylene oxide), Poly(octamethylene oxide), Poly(trimethylene oxide), Poly(3,3-bisazidomethyl-trimethylene oxide), Poly(3,3-bischloromethyl-trimethylene oxide), Poly(3,3-bisbromomethyl-trimethylene oxide), Poly(3,3-bisethoxymethyl-trimethylene oxide), Poly(3,3-bisiodomethyl-trimethylene oxide), Poly(2,2-bistrifluoromethyl-trimethylene oxide), Poly(3,3-dimethyl-trimethylene oxide), Poly(3,3-diethyl-trimethylene oxide), Poly(3-ethyl-3-methyl-trimethylene oxide), Poly(caprylaldehyde), Poly(propionaldehyde), Poly(3-methoxycarbonyl-propionaldehyde), Poly(3-cyano-propionaldehyde), Poly(propylene oxide), Poly(2-chloromethyl-propylene oxide), Poly[3-(1-naphthoxy)-propylene oxide], Poly[3-(2-naphthoxy)-propylene oxide], Poly(3-phenoxy-propylene oxide), Poly[3-(o-chloro-phenoxy)propylene oxide], Poly[3-(p-chloro-phenoxy)propylene oxide], Poly[3-(dimethyl-phenoxy)propylene oxide], Poly[3-(o-isopropyl-phenoxy)propylene oxide], Poly[3-(p-methoxy-phenoxy)propylene oxide], Poly[3-(m-methyl-phenoxy)propylene oxide], Poly[3-(o-methyl-phenoxy)propylene oxide], Poly[3-(o-phenyl-phenoxy)propylene oxide], Poly[3-(2,4,6-trichloro-phenoxy)propylene oxide], Poly(3,3,3-trifluoro-propylene oxide), Poly(tetramethylene oxide), Poly(cyclopropylidenedimethylene oxide), Poly(styrene oxide), Poly(allyloxymethylethylene oxide), Poly(butoxymethylethylene oxide), Poly(butylethylene oxide), Poly(4-chlorobutylethylene oxide), Poly(2-chloroethylethylene oxide), Poly(2-cyanoethyloxymethylene oxide), Poly(t-butylethylene oxide), Poly(2,2-bischloromethyltrimethylene oxide), Poly(decylethylene oxide), Poly(ethoxymethylethylene oxide), Poly(2-ethyl-2-chloromethyltrimethylene oxide), Poly(ethylethylene oxide), Poly [1-(2,2,3,3,-tetrafluorocyclobutyl)ethylene oxide], Poly(octafluorotetramethylene oxide), Poly[1-(heptafluoro-2-propoxymethyl)ethylene], Poly(hexylethylene oxide), Poly[(hexyloxymethyl)ethylene oxide], Poly(methyleneoxy-2,2,3,3,4,4-hexafluoro-pentamethylene oxide), oly(methyleneoxy-2,2,3,3,4,4,5,5-octafluoro-hexamethylene oxide), Poly(1,1-dimethylethylene oxide), Poly(1,2-dimethylethylene oxide), Poly(1-methyltrimethylene oxide), Poly(2-methyltrimethylene oxide), Poly(m-ethyleneoxytetramethylene oxide), Poly(octadecylethylene oxide), Poly(trifluoropropylene oxide), Poly(1,1-difluoroethyliminotetrafluoroethylene oxide), Poly(trifluoromethyliminotetrafluoro oxide), Poly(1,2-hexylene oxide), Poly(ethylenethioethylene oxide), Poly(difluoromethylene sulfide), Poly(methylenethiotetramethylene sulfide), Poly(1-ethylethylene sulfide), Poly(ethylmethylethylene sulfide), Poly(2-ethyl-2-methyltrimethylene sulfide), Poly(ethylenetrimethylene sulfide), Poly(t-butylethylene sulfide), Poly(isopropylethylene sulfide), Poly(hexamethylene sulfide), Poly(1,2-cyclohexylene sulfide), Poly(1,3-cyclohexylene sulfide), Poly(1,2-cyclohexylene sulfone), Poly(1,3-cyclohexylene sulfone), Poly(hexamethylene sulfone), Poly(pentamethylene sulfide), Poly(pentamethylene sulfone), Poly(propylene sulfide), Poly(isobutylene sulfide), Poly(isopropylidene sulfide), Poly(2-butene sulfide), Poly(hexamethylenethiopentamethylene sulfide), Poly(hexamethylenethiotetramethylene sulfide), Poly(trimethylene sulfide), Poly(1-methyltrimethylene sulfide), Poly(3-methyl-6-oxo-hexamethylene sulfide), Poly(1-methyl-3-oxo-trimethylene sulfide), Poly(6-oxohexamethylene sulfide), Poly(2,2-dimethyl-trimethylene sulfide), Poly(trimethylene sulfone), Poly(2,2-dimethyltrimethylene sulfone), Poly(2,2-diethyltrimethylene sulfone), Poly(2,2-dipentyltrimethylene sulfone), Poly(tetramethylene sulfide), Poly(tetramethylene sulfone), Poly(ethylenethiohexamethylene sulfide), Poly(ethylenethiotetramethylene sulfide), Poly(pentamethylenethiotetramethylene sulfide), Poly(tetramethylene sulfide), Poly(decamethylene sulfide), Poly(p-tolyl vinyl sulfoxide), Poly(decamethylene disulfide), Poly(heptamethylene disulfide), Poly(hexamethylene disulfide), Poly(nonamethylene disulfide), Poly(octamethylene disulfide), Poly(pentamethylene disulfide), Poly(octamethylenedithiotetramethylene disulfide), Poly(oxyethylenedithioethylene), Poly(oxyethylenetetrathioethylene), Poly(dimethylketene), Poly(thiocarbonyl-3-methylpentamethylene), Poly(thiocarbonyl-2-methylpentamethylene), Poly(thiocarbonyl-1-methylethylene), Poly(thiocarbonyl-1-p-methoxybenzenesulfonylethylene), Poly(thiocarbonyl-1-tosylaminoethylene), Poly(thiocarbonyl-1-p-chlorobenzenesulfoamidoethylene), Poly(butylethylene amine), Poly(ethylethylene amine), Poly(isobutylethylene amine), Poly(1,2-diethylethylene amine), Poly(1-butyl-2-ethylethyleneamine), Poly(2-ethyl-1-pentylethylene), Poly(N-formyl-isopropylethylene), Poly(isopropylethyleneamine), Poly(N-formylpropylene amine), Poly(ethylenetrimethyleneamine), Poly(N-acetyl-ethylene amine), Poly(N-benzoyl-ethylene amine), Poly[N-(p-chloro-benzoyl)-ethylene amine], Poly(N-butyryl-ethylene amine), Poly[N-[4-(4-methylthiophenoxy)-butyryl]-ethylene amine], Poly(N-cyclohexanecarbonyl-ethylene amine), Poly(N-dodecanoyl-ethylene amine), Poly(N-heptanoyl-ethylene amine), Poly(N-hexanoyl-ethylene amine), Poly(N-isobutyryl-ethylene amine), Poly(N-isovaleryl-ethylene amine), Poly(N-octanoyl-ethylene amine), Poly(N-2-naphthoyl-ethylene amine), Poly(N-p-toluoyl-ethylene amine), Poly(N-perfluorooctaoyl-ethylene amine), Poly(N-perfluoropropionyl-ethylene amine), Poly(N-pivaloyl-ethylene amine), Poly(N-valeryl-ethylene amine), Poly(trimethylene amine), Polysilane, Poly(di-N-hexyl-silane), Poly(di-N-pentyl-silane), Poly(vinyltriethoxysilane), Poly(vinyltrimethoxysilane), Poly(vinyltrimethylsilane), Poly(vinyl methyldiacetoxysilane), Poly(vinyl methyldiethoxysilane), Poly(vinylphenyldimethylsilane), Polysiloxane, Poly(diethylsiloxane), Poly(dimethylsiloxane), Poly(diphenylsiloxane), Poly(dipropylsiloxane), Poly(pentaphenyl-p-toluyltrsiloxane), Poly(phenyl-p-toluylsiloxane), Polytphthalocyaninato-siloxane), Poly(propylmethylsiloxane), Poly(ethylmethylsiloxane), Poly(methyloctylsiloxane), Poly(3,3,3-trifluoropropylmethylsiloxane), Poly(vinylmethylsiloxane), Polysilylene, Poly(dimethylsilylene), Poly(diphenylsilylene), Poly(dimethyldiallylsilane), Poly[oxydi(pentafluorophenyl)silylenedi(oxydimethylylene)], Poly[oxymethylchlorotetrafluorophenylsilylenedi(oxydimethylsilylene)], Poly(oxymethylpentafluorophenylsilylene), Poly(oxymethylpentafluorophenylsilyleneoxydimethylsilylene, Poly[oxymethylpentafluorophenylsilylenedi(oxydimethylsilylene)], Poly(oxymethyl-3,3,3-trifluoropropylsilylene), Poly(oxymethylphenylsilylene), Poly[tri(oxydimethylsilylene)oxy(methyl)trimethylsiloxysilylene], Poly[tri(oxydimethylsilylene)oxy(methyl)-2-phenyl-ethylsilylene], Poly[(4-dimethylaminophenyl)methylsilylenetrimethylene], Poly[(4-dimethylaminophenyl)phenylsilylenetrimethylene], Poly[(methyl)phenylsilylenetrimethylene], Poly(1,1-dimethylsilazane), Poly(dimethylsilylenetrimethylene), Poly(di-p-tolylsilylenetrimethylene), Poly(phosphazene), Poly(bis-beta-naphthoxy-phosphazene), Poly(bis-phenoxy-phosphazene), Poly(di-p-methyl-bis-phenoxy-phosphazene), Poly (di-p-chloro-bis-phenoxy-phosphazene), Poly(di-2,4-dichloro-bis-phenoxy-phosphazene), Poly(di-p-phenyl-bis-phenoxy-phosphazene), Poly(di-m-trifluoromethyl-phosphazene), Poly(di-methyl-phosphazene), Poly(dichoro-phosphazene), Poly(diethoxy-phosphazene), Poly[bis(ethylamino)phosphazene], Poly[bis(2,2,2-trifluoroethoxy)phosphazene], Poly[bis(3-trifluoromethylphenoxy)phosphazene], Poly[bis(1H,1H-pentadecafluorooctyloxy)phosphazene], Poly[bis(1H,1H-pentafluoropropoxy)phosphazene], Poly(dimethoxyphosphazene), Poly[bis(phenylamino)phosphazene], Poly[bis(piperidino)phosphazene], Poly(diethylpropenyl phosphate), Poly(diethylisopropenylphosphate), Poly[vinyl bis(chloroethyl) phosphate], Poly(vinyldisethyl phosphate), Poly(vinyldiethyl phosphate), Poly(vinyldiphenylphosphate), Poly(alpha-bromovinyldiethyl phosphonate), Poly(alpha-carboethoxyvinyl diethyl phosphonate), Poly(alpha-carbomethoxyvinyl diethyl phosphonate), Poly(isopropenyl dimethyl phosphonate), Poly [vinyl bis(2-chloroethyl) phosphonate], Poly(vinyl dibutyl phosphonate), Poly(vinyl diethyl phosphonate), Poly(vinyldiisobutyl phosphonate), Poly(vinyl diisopropyl phosphonate), Poly(vinyl dimethyl phosphonate), Poly(vinyl diphenyl phosphonate), Poly(vinyl dipropyl phosphonate), Poly[2-(4-vinylphenyl)ethyl diethyl phosphonate), Poly(4-vinylphenyl diethyl phosphonate), and Poly(diphenylvinyl phosphine oxide).

Method of Manufacture

A method of responsive microgel synthesis and production is further an object of the present invention. The method of the present invention involves a single synthetic step, which is advantageous for scale-up of responsive microgel fabrication. The synthesis of the microgels described herein involves a free-radical copolymerization of a vinyl monomer with a divinyl cross-linker with simultaneous hydrogen abstraction from a polymer present in the reaction system. The hydrogen abstraction leads to generation of macro-radicals that lead to the grafting of the amphiphilic copolymer 'dangling chains' onto the growing microgel network. The series of reactions that occur simultaneously and yield a responsive microgel of the present invention are shown in FIG. 4 (scheme of the one-step synthesis of responsive microgels). See, e.g., Examples I and II.

A preferred chain-transfer reaction to covalently bond the nonionic copolymer to the ionizable network is a free-radical polymerization (using a redox free-radical initiator) of an ionizable monomer and a divinyl cross-linker.

A method of making the responsive microgel covalently cross-linked polymer network (graft-comb copolymer) of the present invention, for example, comprises the steps of: a) providing, an ionizable monomer, a divinyl cross-linker, a free radical, and a nonionic copolymer; and, b) copolymerizing the ionizable monomer with the divinyl cross-linker to produce an ionizable network, while c) abstracting hydrogen from the nonionic copolymer with the free radical to progress a chain transfer reaction wherein the nonionic copolymer is covalently bonded onto the ionizable network to produce a responsive microgel as defined herein.

Divinyl cross-linker as used herein refers to a reactive chemical having at least two ethylenic double bonds capable of participating in at least two growing polymer chains. Examples of cross-linkers of this type, which are normally used as crosslinkers in polymerization reactions, are N,N'-methylenebisacrylamide, polyethylene glycol diacrylates and polyethylene glycol dimethacrylates which are derived in each case from polyethylene glycols with a molecular weight of from 106 to 8500, preferably 400 to 2000, trimethylolpropane triacrylate, trimethylolpropane trimethacrylate, ethylene glycol diacrylate, propylene glycol diacrylate, butanediol diacrylate, hexanediol diacrylate, hexanediol dimethacrylate, diacrylates and dimethacrylates of block copolymers of ethylene oxide and propylene oxide, polyhydric alcohols such as glycerol or pentaerythritol which are esterified two or three times with acrylic acid or methacrylic acid, triallylamine, tetraallylethylenediamine, divinylbenzene, diallyl phthalate, polyethylene glycol divinyl ethers of polyethylene glycols with a molecular weight of from 126 to 4000, trimethylolpropane diallyl ether, butanediol divinyl ether, pentaerythritol triallyl ether and/or divinylethyleneurea. Water-soluble crosslinkers are preferably used, e.g. N,N'-methylenebisacrylamide, oligoethylene glycol diacrylates and oligoethylene glycol dimethacrylates derived from adducts of 2 to 400 mol of ethylene oxide and 1 mol of a diol or polyol, vinyl ethers of adducts of 2 to 400 mol of ethylene oxide and 1 mol of a diol or polyol, ethylene glycol diacrylate, ethylene glycol dimethacrylate or triacrylates and trimethacrylates of adducts of 6 to 20 mol of ethylene oxide and one mol of glycerol, pentaerythritol triallyl ether and/or divinylurea.

Also suitable as crosslinkers are compounds, which contain at least one polymerizable ethylenically unsaturated group and at least one other functional group. The functional group in these crosslinkers must be able to react with the functional groups, essentially the carboxyl groups in the monomers of the backbone. Examples of suitable functional groups are hydroxyl, amino, epoxy and aziridino groups.

Also suitable as crosslinkers are those compounds which have at least two functional groups able to react with carboxyl and other functional groups in the monomers used. The suitable functional groups have already been mentioned above, i.e. hydroxyl, amino, epoxy, isocyanate, ester, amide and aziridino groups. Examples of such crosslinkers are ethylene glycol, diethylene glycol, triethylene glycol, tetraethylene glycol, polyethylene glycol, glycerol, polyglycerol, propylene glycol, polypropylene glycol, block copolymers of ethylene oxide and propylene oxide, sorbitan fatty acid esters, ethoxylated sorbitan fatty acid esters, trimethylolpropane, pentaerythritol, polyvinyl alcohol, sorbitol, polyglycidyl ethers such as ethylene glycol diglycidyl ether, polyethylene glycol diglycidyl ether, glycerol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether, polyaziridine compounds such as 2,2-bishydroxymethylbutanol tris[3-(1-aziridinyl)propionate], 1,6-hexamethylenediethyleneurea, 4,4'-methylenebis(phenyl)-N,N'-diethyleneurea, halo epoxy compounds such as epichlorohydrin and a-methylfluorohydrin, polyisocyanates such as 2,4-tolylene diisocyanate and hexamethylene diisocyanate, alkylene carbonates such as 1,3-di-oxolan-2-one and 4-methyl-1,3-dioxolan-2-one, polyquaternary amines such as condensates of dimethylamine with epichlorohydrin, homo- and copolymers of diallyldimethylammonium chloride, and homo- and copolymers of dimethylaminoethyl (meth)acrylate, which are, where appropriate, quaternized with, for example, methyl chloride.

Other suitable crosslinkers are polyvalent metal ions able to form ionic crosslinks. Examples of such crosslinkers are magnesium, calcium, barium and aluminum ions. A preferred crosslinker of this type is sodium aluminate. These crosslinkers are added, for example, as hydroxides, carbonates or bicarbonates to the aqueous polymerizable solution.

Other suitable crosslinkers are multifunctional bases which are likewise able to form ionic crosslinks, for example polyamines or their quaternized salts. Examples of polyamines are ethylenediamine, diethylenetriamine, triethylenetetramine, tetraethylenepentamine, pentaethylenehexamine and polyethyleneimines, and polyvinylamines with molecular weights of up to 4,000,000 in each case.

In a preferred embodiment of the invention, divinyl crosslinkers are used. These can be hydrophobic or most preferably amphiphilic or hydrophilic. Apart from polyvalent metal ions, all the water-insoluble crosslinkers which are described above and can be assigned to the various groups are suitable for producing gels. Some preferred hydrophobic crosslinkers are diacrylates or dimethacrylates or divinyl ethers of alkanediols with 2 to 25 carbon atoms (branched, linear, with any suitable arrangement of OH groups) such as 1,3-propanediol, 1,4-butanediol, 1,6-hexanediol, neopentyl glycol, 1,9-nonanediol or 1,2-dodecanediol, di-, tri- or polypropylene glycol diacrylates or dimethacrylates, allyl acrylate, allyl methacrylate, divinylbenzene, glycidyl acrylate or glycidyl methacrylate, allyl glycidyl ether and bisglycidyl ethers of the alkanediols listed above.

Examples of suitable hydrophilic crosslinkers are N,N'-methylenebisacrylamide, polyethylene glycol diacrylates or dimethacrylates with a molecular weight from 200 to 4000, divinylurea, triallylamine, diacrylates or dimethacrylates of adducts of from 2 to 400 mol of ethylene oxide and 1 mol of a diol or polyol or the triacrylate of an adduct of 20 mol of ethylene oxide and 1 mol of glycerol and vinyl ethers of adducts of from 2 to 400 mol of ethylene oxide and 1 mol of a diol or polyol.

The polymerization initiators which can be used are all initiators which form free radicals under the polymerization conditions and which are normally used in the preparation of responsive gels. It is also possible to initiate the polymerization by the action of electron beams on the polymerizable aqueous mixture. However, the polymerization can also be started in the absence of initiators of the abovementioned type by the action of high-energy radiation in the presence of photoinitiators.

Polymerization initiators which can be used are all compounds which decompose to free radicals under the polymerization conditions, e.g. peroxides, hydroperoxides, hydrogen peroxide, persulfates, azo compounds and the redox catalysts. Initiators soluble in the mixture of the monomer and amphiphilic copolymer are preferably used. It is advantageous in some cases to use mixtures of various polymerization initiators, e.g. most preferably mixtures of lauroyl peroxide or benzoyl peroxide hydrogen peroxide with 2,2'-azobis(2,4-dimethylpentanenitrile) or 4,4'-azobis(4-cyanovaleric acid). Examples of suitable organic peroxides are acetylacetone peroxide, methyl ethyl ketone peroxide, tertbutyl hydroperoxide, cumene hydroperoxide, tertamyl perpivalate, tert-butyl perpivalate, tert-butyl pemeohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-trimethylhexanoate, acetyl cyclohexylsulfonyl peroxide, dilauroyl peroxide, dibenzoyl peroxide and tert-amyl pemeodecanoate. Also suitable polymerization initiators are water-soluble azo initiators, e.g. 2,2'-azobis(2-amidinopropane) dihydrochloride, 2,2'-azobis(N,N'-dimethyleneisobutyramidine) dihydrochloride, 2-(carbamoylazo)isobutyronitrile, 2,2'-azobis[2-(2-imidazolin-2-yl)propane] dihydrochloride and 4,4,-azobis(4-cyanovaleric acid). Polymerization initiators are used in conventional amounts, e.g. in amounts of from 0.01 to 5, preferably 0.1 to 2.0, % of the weight of the monomers to be polymerized.

Also suitable as initiators are redox catalysts. The redox catalysts contain as oxidizing component at least one of the abovementioned peroxy compounds and as reducing component, for example, ascorbic acid, glucose, sorbose, ammonium or alkali metal bisulfite, sulfite, thiosulfate, hyposulfite, pyrosulfite or sulfide, metal salts such as iron (II) ions or silver ions, or sodium hydroxymethylsulfoxylate. The reducing component preferably used in the redox catalyst is ascorbic acid or sodium sulfite. Based on the amount of monomers used in the polymerization, for example, from $3\times10^{-6}$ to 1 mol % of the reducing component of the redox catalyst system and from 0.001 to 5.0 mol % of the oxidizing component of the redox catalyst are used.

If the polymerization is initiated by the action of high-energy radiation, photoinitiators are normally used as initiator. These may be, for example, alpha-splitters, H-abstracting systems or else azides. Examples of initiators of these types are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds like the free-radical formers mentioned above, substituted hexaarylbisimidazoles or acylphosphine oxides. Examples of azides are: 2-(N,N-dimethylamino) ethyl 4-azidocinnamate, 2-(N,N-dimethylamino)ethyl-4-azidonaphthyl ketone, 2-(N,N-dimethylamino)ethyl 4-azidobenzoate, 5-azido-1-naphthyl 2-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone. The photoinitiators are, if employed, normally used in amounts of from 0.01 to 5% of the weight of the monomers to be polymerized.

In one embodiment, it is preferred to use free-radical initiators capable of abstracting tertiary and secondary hydrogens from the backbone of the amphiphilic polymer of the present invention.

Method of Use

One of the major concerns in the delivery of drugs is the bioavailability of the drug. Depending upon the nature of the drug and the route of delivery, the bioavailability may be very low due to, for example, the degradation of oral-delivered drugs by hepato-gastrointestinal first-pass elimination or rapid clearance of the drug from the site of application. The net result is that frequent dosing may be required with higher than needed amounts of drug, which can lead to undesired side effects. Thus, it is desired by the pharmaceutical industry to have ways of administering drugs such that their availability can be controlled in an even dosing manner, the amounts of drugs can be kept as low as possible to minimize side effects, and dosing regime can be kept to a minimum to provide greater convenience to the subject, thus promoting greater compliance with appropriate dosing.

The responsive microgels of the present invention are useful in a wide variety of chemo-mechanical applications in that they display diverse phase transition characteristics. A method, for example, of delivering at least one therapeutic or cosmetic agent to a mammalian subject is a preferred embodiment of the invention which comprises administering a responsive microgel of the present invention to the subject which comprises at least one such agent.

A method of delivering an effective amount at least one therapeutic agent to a patient is a preferred method of the invention which comprises administering an effective amount of a responsive microgel of the present invention which comprises at least one therapeutic agent. Therapeutic regimens for the prevention and/or treatment of cancer frequently requires, for example, the administration of an effective amount of a cationic, hydrophobic, and/or amphiphilic compound, individually or in combinations. The responsive microgel of the present invention is particularly suited for therapeutic administration of these types of agents or entities. The responsive microgels are provided as a long-term delivery device for therapeutic agents and to enhance the therapeutic profile. The responsive microgels provide improved and substantially linear sustained release of therapeutic agents to improve and prolong the bioavailability of the agent. The reversibly gelling responsive microgel of this invention has the physico-chemical characteristics that make it a suitable delivery vehicle for conventional small chemical drugs as well as new macromolecular (e.g., peptides) drugs or therapeutic products.

The responsive microgel of the present invention is particularly suited for oral administration. The responsive microgel of the present invention may also be employed to deliver therapeutic entities (including cosmetic agents), for example, by intranasal, ocular, pulmonary, colonic, vaginal, as well as topical administration. The temperature-responsive mode of solute solubilization, for example, by microgels of the present invention is useful for medicinal as well as cosmetic formulations. Preferred therapeutic entities for use in the present invention include but are not limited to doxorubicin, mitoxantrone, mitomycin C, as well as the Taxanes including but not limited to (paclitaxel (TAXOL®), and docetaxel (TAXOTERE®)).

Examples of therapeutic entities that might be utilized in a delivery application of the invention include literally any hydrophilic or hydrophobic biologically active compound. Preferably, though not necessarily, the drug is one that has already been deemed safe and effective for use by the appropriate governmental agency or body. For example, drugs for human use listed by the FDA under 21 C.F.R. 330.5, 331 through 361; 440–460; drugs for veterinary use listed by the FDA under 21 C.F.R. 500–582, incorporated herein by reference, are all considered acceptable for use in the present responsive microgel.

Drugs that are not themselves liquid at body temperature can be incorporated into the responsive microgel of the present invention. Moreover, peptides and proteins which may normally be rapidly degraded by tissue-activated enzymes such as peptidases, can be passively protected in the microgels described herein.

A responsive microgel which comprises at least one therapeutic entity is particularly preferred. A responsive microgel which comprises at least one anticancer agent is a preferred embodiment of the present invention wherein, for example, at least one anticancer agent is selected from the group consisting of (a steroidal antiandrogen, a non steroidal antiandrogen, an estrogen, diethylstilbestrol, a conjugated estrogen, a selective estrogen receptor modulator (SERM), a taxane, and a LHRH analog). Non steroidal antiandrogen as referred to herein includes but is not limited to the group consisting essentially of (finasteride (PROSCAR®), flutamide (4'-nitro-3'-trifluoromethyl isobutyranilide), bicalutamide (CASODEX®), and nilutamide). SERM as referred to herein includes but is not limited to the group consisting essentially of (tamoxifen, raloxifene, droloxifene, and idoxifene). LHRH analog as referred to herein includes but is not limited to the group consisting essentially of (goserelin acetate (ZOLADEX®), and leuprolide acetate (LUPRON®)).

A method of prevention or treatment of a tumor is provided comprising administering a therapeutically effective amount of a responsive microgel which comprises at least one therapeutic entity to a patient wherein the patient is either at risk of developing a tumor or already exhibits a tumor. A method of prevention or treatment of a tumor is provided wherein at least one agent described herein—or a stereoisomeric mixture thereof, diastereomerically enriched, diastereomerically pure, enantiomerically enriched or enantiomerically pure isomer thereof, or a prodrug of such compound, mixture or isomer thereof, or a pharmaceutically acceptable salt of the compound, mixture, isomer or prodrug—is administered in a therapeutically effective amount comprised within a responsive microgel of the present invention to a patient wherein the patient is either at risk of developing a tumor or already exhibits a tumor. Methods of employing the responsive microgel of the present invention for the prevention or treatment of a tumor is provided wherein at least one agent is comprised within the microgel selected from the group consisting of (a steroidal antiandrogen, a non steroidal antiandrogen, an estrogen, diethylstilbestrol, a conjugated estrogen, a selective estrogen receptor modulator (SERM), a taxane, and a LHRH analog) and an effective amount of the microgel is administered to a patient in need of treatment.

The term therapeutic entity includes pharmacologically active substances that produce a local or systemic effect in a mammal. The term thus means any substance intended for use in the diagnosis, cure, mitigation, treatment or prevention of disease or in the enhancement of desirable physical or mental development and conditions in a mammal.

Therapeutic entities for employment with the responsive microgels described herein therefore include small molecule compounds, polypeptides, proteins, nucleic acids, and PLURONIC®, for example, as described herein (e.g., and for the formation of mixed micelles).

Examples of proteins include antibodies, enzymes, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, angiotensin I and II, bradykinin, kallidin, adrenocorticotropic hormone, thyroid stimulating hormone, insulin, glucagon and the numerous analogues and congeners of the foregoing molecules.

Classes of pharmaceutically active compounds which can be loaded onto responsive microgel compositions of the invention include, but are not limited to, anti-AIDS substances, anti-cancer substances, antibiotics, immunosuppressants (e.g. cyclosporine) anti-viral substances, enzyme inhibitors, neurotoxins, opioids, hypnotics, antihistamines, tranquilizers, anti-convulsants, muscle relaxants and anti-Parkinson substances, anti-spasmodics and muscle contractants, miotics and anti-cholinergics, antiglaucoma compounds, anti-parasite and/or anti-protozoal compounds, antihypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, and vaccines.

A more complete listing of classes of compounds suitable for loading into polymers using the present methods may be found in the Pharmazeutische Wirkstoffe (Von Kleemann et al. (eds) Stuttgart/New York, 1987, incorporated herein by reference). Examples of particular pharmaceutically active substances are presented below:

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir( ), phosphonoformic acid, 1-adamantanamine, peptide T, and 2',3' dideoxycytidine.

Anti-cancer substances are substances used to treat or prevent cancer. Examples of such substances include methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazolecarboxamide), methotrexate, fluorouracil, 5-fluorouracil, cytarabine, cytosine arabinoxide, mercaptopurine, 6-mercaptopurine, thioguanine.

Antibiotics are art recognized and are substances which inhibit the growth of or kill microorganisms. Antibiotics can be produced synthetically or by microorganisms. Examples of antibiotics include penicillin, tetracycline, chloramphenicol, minocycline, doxycycline, vanomycin, bacitracin, kanamycin, neomycin, gentamycin, erythromycin and cephalosporins.

Anti-viral agents are substances capable of destroying or suppressing the replication of viruses. Examples of anti-viral agents include a-methyl-P-adamantane methylamine, 1,-D-ribofuranosyl-1,2,4-triazole-3 carboxamide, 9->2-hydroxyethoxy!methylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine, 1-hydroxy maleate, iodotubercidin, p-bromotetramisole, 10-(alpha-diethylaminopropionyl)-phenothiazine hydrochloride, calmidazolium chloride, hemicholinium-3,3,5-initrocatechol, diacylglycerol kinase inhibitor I, diacylglycerol kinase inhibitor II, 3-phenylpropargylamine, N.sup.6-monomethyl-L-arginine acetate, carbidopa, 3-hydroxybenzylhydrazine HCl, hydralazine HCl, clorgyline HCl, deprenyl HCl, L(−)-,deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2- diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine PCMB), 8,9-dichloro-2,3,4,5-tetrahydro-1H-2-benzazepine hydrochloride, p-aminoglutethimide, p-aminoglutethimide tartrate,R(+)-, p-aminoglutethimide tartrate,S(−)-, 3-iodotyrosine, alpha-methyltyrosine,L-, alpha -methyltyrosine,D L-, acetazolamide, dichlorphenamide, 6-hydroxy-2-benzothiazolesulfonamide, and allopurinol.

Neurotoxins are substances which have a toxic effect on the nervous system, e.g. nerve cells. Neurotoxins include adrenergic neurotoxins, cholinergic neurotoxins, dopaminergic neurotoxins, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine HBr, 1-methyl-4-(2-methylphenyl)-1,2,3,6-tetrahydro-pyridine hydrochloride, 1-methyl-4-phenyl-2,3-dihydropyridinium perchlorate, N-methyl-4phenyl-1,2,5,6-tetrahydropyridine HCl, 1-methyl-4phenylpyridinium iodide.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include nor-binaltorphimine HCl, buprenorphine, chlomaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarimides, diethyl isovaleramide, a-bromoisovaleryl urea, urethanes and disulfanes.

Antihistamines are substances which competitively inhibit the effects of histamines. Examples include pyrilamine, chlorpheniramine, tetrahydrazoline, and the like.

Lubricants are substances that increase the lubricity of the environment into which they are delivered. Examples of biologically active lubricants include water and saline.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, Chk and ethosuximide.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergics are compounds which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma compounds include betaxalol, pilocarpine, timolol, timolol salts, and combinations of timolol, and/or its salts, with pilocarpine.

Anti-parasitic, -protozoal and -fungals include ivermectin, pyrimethamine, trisulfapyrimidine, clindamycin, amphotericin B, nystatin, flucytosine, natamycin, and miconazole.

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain. Examples of analgesics include morphine sulfate, codeine sulfate, meperidine, and nalorphine.

Anti-pyretics are substances capable of relieving or reducing fever and anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which have an anesthetic effect in a localized region. Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

In topical skin care applications, a variety of active substances may be advantageously employed. By way of example only suitable active agents which may be incorporated into the cosmetic composition include anti-aging active substances, anti-wrinkle active substances, hydrating or moisturizing or slimming active substances, depigmenting active substances, substances active against free radicals, anti-irritation active substances, sun protective active substances, anti-acne active substances, firming-up active substances, exfoliating active substances, emollient active substances, and active substances for the treating of skin disorders such as dermatitis and the like.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include dopamine, serotonin, q-aminobutyric acid, norepinephrine, histamine, acetylcholine, and epinephrine.

Cell response modifiers are chemotactic factors such as platelet-derived growth factor (PDGF). Other chemotactic factors include neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, nerve growth factor, and bone growth/cartilage-inducing factor (alpha and beta), or other bone morphogenetic protein.

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins.

As those skilled in the art will appreciate, the foregoing list is exemplary only. Because the responsive microgel of the present invention is suited for application under a variety of physiological conditions, a wide variety of pharmaceutical agents may be loaded onto the responsive microgels described herein and administered.

Formulations

Tablet Excipients. It has been demonstrated that standard pharmaceutical processes, such as lyophilization and air-drying can process the responsive microgel of the invention. The reversible thermal viscosifying responsive microgel may be reconstituted with water, phosphate buffer or calcium chloride solution, without loss or degradation of rheological properties. Thus, it is contemplated that the responsive microgel of the invention may also be incorporated as excipients into tablets or granules for oral delivery, for example. The responsive microgel may be coated on an outer surface of the tablet or may be introduced in powder form into the tablet along with the active agent and other ingredients. The poloxamer:poly(acrylic acid) composition may be used to promote bioadhesion of the tablet and its contents with the mucosal lining of the gastro-intestinal tract to extend transit time.

Also, when incorporated as a powder, the slow dissolution rate of the end-modified responsive microgel makes it a suitable excipient to sustained release tableting formulation. The addition of such responsive microgel would yield to a slow release of the incorporated drug.

Injectables. The end-modified responsive microgel composition of the invention is well-suited for use in injectable applications. A depot formulation may be prepared and administered at low viscosity to a subdermal or intramuscular site, for example. The responsive microgel will viscosify and form a depot site, which will slowly release the active agent. The reversible thermally viscosifying responsive microgel, upon contact with body fluids including blood or the like, undergoes gradual release of the dispersed drug for a sustained or extended period (as compared to the release from an isotonic saline solution). This can result in prolonged delivery (over, say 1 to 2,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Preparation of pharmaceutic compositions may be accomplished with reference to any of the pharmaceutic formulation guidebooks and industry journals which are available in the pharmaceutic industry. These references supply standard formulations which may be modified by the addition or substitution of the reversible viscosifying composition of the present invention into the formulation. Suitable guidebooks include Pharmaceutics and Toiletries Magazine, Vol. 111 (March, 1996); Formulary: Ideas for Personal Care; Croda, Inc, Parsippany, N.J. (1993); and Pharmaceuticon: Pharmaceutic Formulary, BASF, which are hereby incorporated in their entirety by reference.

The pharmaceutic composition may be in any form. Suitable forms will be dependant, in part, of the intended mode and location of application. Ophthalmic and otic formulations are preferably administered in droplet or liquid form; nasal formulations are preferable administered in droplet or spray form, or may be administered as a powder (as a snuff); vaginal and rectal formulations are preferably administered in the form of a cream, jelly or thick liquid; veterinary formulations may be administered as a cream, lotion, spray or mousse (for application to fur or exterior surface); esophageal and buccal/oral cavity applications are preferably administered from solution or as a powder; film forming applications or dermal applications may be administered as a lotions, creams, sticks, roll-ons formulations or pad-applied formulations.

Exemplary drugs or therapeutics delivery systems which may be administered using the aqueous responsive composition compositions of the invention include, but are in no way limited to, mucosal therapies, such as esophageal, otic, rectal, buccal, oral, vaginal, and urological applications; topical therapies, such as wound care, skin care and teat dips; and intravenous/subcutaneous therapies, such as intramuscular, intrabone (e.g., joints), spinal and subcutaneous therapies, tissue supplementation, adhesion prevention and parenteral drug delivery. In addition, further applications include transdermal delivery and the formation of depots of drug following injection. It will be appreciated that the ionic nature of the biocompatible component of the responsive composition provides an adhesive interaction with mucosal tissue.

The responsive microgels of the present invention may be understood with reference to the following examples, which are provided for the purposes of illustration of example embodiments, and are not intended to limit the scope of the claims appended hereto.

EXAMPLES

Example I

Drug Release from Responsive Microgels of Polyether-Modified Poly(Acrylic Acid).

PLURONIC® F127 NF, L92 and L61 were obtained from BASF Corp. (Mount Olive, N.J.) and used as received. The properties of these PLURONIC® surfactants are presented in Table 1:

| Copolymer | Nominal MW | Number of PO units | Number of EO units | Hydrophilic-lipophilic balance | Cloud point in water at 1 wt %, °C. | Critical micelle concentration at 25° C., M |
|---|---|---|---|---|---|---|
| L61 | 2000 | 30 | 6 | 3 | 32 | $1.1 \times 10^{-4}$ |
| L92 | 3650 | 60 | 16 | 6 | 69 | $8.8 \times 10^{-5}$ |
| F127 | 12600 | 65 | 200 | 22 | >100 | $2.8 \times 10^{-6}$ |

Table 1. Properties of the PLURONIC® surfactants used in this study. M. Yu. Kozlov, *Macromolecules*, 2000, 33, 3305–3313; M. J. Kositza, et al., *Langmuir*, 1999, 15, 322–325; BASF Catalog.

Materials

A fluorescent dye, 5-(4,6-dichlorotriazinyl)aminofluorescein (DCTAF, 99%) was obtained from Molecular Probes, Inc. (Eugene, Oreg.). Acrylic acid (99%, vinyl monomer), ethylene glycol dimethacrylate (98%, divinyl cross-linker, EGDMA), dodecane (99+%, solvent), 4,4'-azobis(4-cyanovaleric acid) (75+%, azo initiator), and lauroyl peroxide (97%, redox initiator) were purchased from Aldrich Chemical Co. and used as received. Poly(vinylpyrrolidinone-co-1-hexadecene) (Ganex V-216) (dispersion stabilizer) was obtained from International Specialty Products (Wayne, N.J.). Doxorubicin hydrochloride of 99% purity was obtained from Hande Tech USA (Houston, Tex.), a subsidiary of Yunnan Hande Technological Development Co. (Kunming, P.R.China). All other chemicals, gases and organic solvents of the highest purity available were obtained from commercial sources.

Microgel Synthesis

Synthesis was carried out on a laboratory scale in an adiabatic mode. Acrylic acid (vinyl monomer) (40 mL) was partially neutralized by addition of 5 M NaOH aqueous solution (0.5 mL). PLURONIC® F127 or L92 (24 g) was dissolved in the resulting solution under nitrogen and a desired amount of ethylene glycol dimethacrylate (EGDMA) (divinyl cross-linker) was added. Amounts of EGDMA were set such that resulted in 1 mol % relative degree of cross-linking of the microgels [cross-linking mol %=100×(number of mols of EGDMA/the number of mols of acrylic acid)]. Lauroyl peroxide (redox initiator) (100 mg) and 4,4'-azobis(4-cyanovaleric acid) (azo initiator) (100 mg) were dissolved in 2 mL of acrylic acid (vinyl monomer) and added to the solution of PLURONIC® in acrylic acid. The resulting solution was deaerated by nitrogen bubbling for 0.5 h and added to a 3-necked 0.5-mL flask containing 1 wt % solution of Ganex V-216 (dispersion stabilizer) in dodecane (solvent) (200 mL). The flask was vigorously stirred by a mechanical stirrer and deaerated by constant nitrogen purge from the bottom. Then the flask was heated to 70° C. using an oil bath and kept at that temperature under stirring and nitrogen purge. After about 1 h, formation of white particles was observed on the flask walls. The reaction was continued at 70° C. for another 3 h. Then the reactor was disassembled, and the contents of the reactor were filtered using Whatman filter paper (retention size 10 µm). The microgel particles were extensively washed by hexane and dried under vacuum. Spherical particles were observed under microscope. Particle sizing was performed in hexane using a ZetaPlus Zeta Potential Analyzer (Brookhaven Instruments Co.). Typical batches of particles made with PLURONIC® F127 and L92 were measured to have effective median diameter of 13 µm (polydispersity 1.4) and 6 µm (polydispersity 1.3), respectively.

In order to ascertain the grafting of PLURONIC® segments onto cross-linked poly(acrylic acid) [poly(vinyl monomer)] networks, a particulate sample was suspended in 1 M NaOH for 3 days and lyophilized. The sample was then placed into a Soxhlet extractor charged with dichloromethane and kept under reflux for 2 days. The wash-outs were collected, evaporated under vacuum, and weighed. Preliminary experiments demonstrated negligible solubility of poly(sodium acrylate), and total solubility of the PLURONIC®, respectively, in dichloromethane. The fraction of the PLURONIC® washed from the particles was negligible, within experimental error (±5% of the initial PLURONIC® content). Hence, for all practical purposes, the overall composition of the microgels in the present study corresponded to that set in the reactor. That is, the weight ratio of PLURONIC® to poly(acrylic acid) [poly(vinyl monomer)] in the particles was 43:57.

Synthesis of Labeled PLURONIC® L61

The DCTAF-labeled PLURONIC® L61 was synthesized and purified essentially as described by Ahmed, F., et al., S. *Langmuir*, 2001, 17, 537–546. Stock solutions of 6 w/v % PLURONIC® L61 were prepared by dissolving the polymer in 0.1 M sodium bicarbonate solution at pH=9.30. A stock solution of 20 g/L 5-DTAF was prepared by dissolving the fluorescein probe in dimethyl sulfoxide (DMSO). The 5-DTAF solution was diluted in 0.1 M sodium bicarbonate solution and added to the PLURONIC® block copolymer solution such that the molar ratio of 5-DTAF to PLURONIC® was 1:1. The reaction was allowed to proceed in the dark at room temperature overnight. To separate the labeled PLURONIC® from the excess unreacted 5-DTAF, the size exclusion chromatography was applied. Sephadex G-25 beads (Aldrich Chemical Co.) swollen in boiling 0.05 M NaCl solution were first packed into a Chromaflex column (ID, 2.5 cm, length, 60 cm) (Kimble/Kontes, Vineland, N.J.). The column was then primed by washing with 0.05 M NaCl solution, followed by passage of 1 bed volume of 6 w/v % unlabeled PLURONIC® in sodium bicarbonate solution and 2–3 bed volumes of 0.05 M NaCl solution. A 250 µL sample of the reaction mixture was then added to the column, and the labeled product was eluted with NaCl solution. The yellow bands moving down the length of the column were separated and the PLURONIC®-containing fraction was concentrated using a Centricon centrifugal filter device (Millipore Corp., Bedford, Mass.) with a molecular weight cutoff of 1500. The samples were centrifuged at ca. 5000×g for 1 h. The retentate containing labeled PLURONIC® was lyophilized and kept at −20° C. in the dark. Given the dye molar extinction coefficient of 83000 $M^{-1}$ $cm^{-1}$ and molecular weight of 495.3, the efficiency of the DCTAF dye conjugation with PLURONIC® molecule was estimated to be 2.4–3.0%.

Solute Loading onto Microgels

The loading level of doxorubicin or PLURONIC® L61 labeled with DCTAF into microgels was measured using a Millipore Ultrafree-MC Centrifugal Filter Device (Millipore Corp.). A microgel was suspended in Tris buffer (10 mM, pH 7.0) and 1 mL of the suspension (40 mg gel/mL buffer) were equilibrated with 6.0 mM stock solution of a drug (9 mL) for 72 h while shaking. Shaking was performed using a KS10 orbital shaker (BEA-Enprotech Corp., Hyde Park, Mass.) in an environmental chamber at 37° C. After equilibration, the microgel particles were filtered off by centrifugation (10000×g, 0.5 h) and supernatant was assayed for drug concentration. A Shimadzu Model 1600 PC spectrophotometer with a temperature-controlled quartz cuvette (path length 1 cm) was used for electronic absorption measurements. The extinction coefficients of doxorubicin ($\lambda$=482 nm) was determined to be 12300 $M^{-1}$ $cm^{-1}$. Assuming the average molecular weight of 2000, the extinction coefficients of the DCTAF-labeled PLURONIC® ($\lambda$=492 nm) was measured at pH 7.0 to be 2600 $M^{-1}$ $cm^{-1}$. The drug uptake was calculated from the absorbance readings in the appropriately diluted stock solution and in the system equilibrated with microgel. The U values were measured in triplicate for each drug and gel, respectively. In a control series of experiments, equilibration of 24 µmol/mL doxorubicin with microgels for 1 week yielded U values close (within experimental error) to the ones obtained with 6 µmol/mL solutions under otherwise identical conditions (see above). This ensured equilibrium U values. The gels equilibrated with corresponding drugs were snap-frozen in liquid nitrogen, lyophilized, and stored at –70° C. in the dark. In the subsequent release studies, the dry gel powders of known U were reconstituted with Tris buffer (10 mM, pH 7.0) to result in the known concentration of the gel and drug.

Release Studies

Drug release from microgels loaded with either DCTAF-labeled PLURONIC® or doxorubicin was studied using the dynamic dialysis technique of Gupta, P. K., et al., J. Pharm. Sci., 1987, 76, 141–145. A Teflon-made, thermostatted dynamic dialyzer consisted of two chambers, separated by a dialysis membrane (cellulose ester, working area A=0.35 $cm^2$, molecular weight cut-off 100 kDa, Spectrum Laboratories). A cylindrical feed chamber (volume $V_f$=5.0 mL) containing drugs or drug-loaded gels was vigorously stirred by a magnetic bar, while a receiver chamber had an inlet and outlet for a constant flow of the receiver solution. The receiver solution (Tris buffer, 10 mM, pH 7.0) was circulated along the dialysis membrane using a P625/275 peristaltic pump (Instech Laboratories). Concentration of the drug in the receiver solution was monitored online by passing through a thermostatted quartz cuvette (path length 1.0 cm). Concentration of solutes was measured periodically using a Shimadzu Model RF-5301 PC spectrofluorophotometer (slit widths 3.0 nm). The dialyzer was maintained at 37° C. by submersion in a water bath. The flow rate through the receiver chamber was maintained at 1.5 mL/min. In a series of preliminary experiments, it was established that at this flow rate the doxorubicin transport becomes flow rate-independent, and yet the flow of the PLURONIC® solution affords avoiding any foaming. The total volume of the receiver solution ($V_r$), including the chamber, cuvette, and 0.093" tubing, was 98 mL in all experiments.

Permeability of the dialysis membrane was determined by loading a certain amount ($q_f^0$) of either doxorubicin or PLURONIC® solution into the feed chamber and measuring the kinetics of release. The dialysis membrane had been soaked in the corresponding solute solution for 48 h prior to the kinetic measurement. To remove excess solute, the membrane was gently wiped up by a paper tissue on both sides immediately prior to the loading into the dialyzer. The membrane thickness ($\delta$) was measured microscopically in the receiver solution upon completion of the dialysis experiment and was typically in the order of 100 µm. Solving the $1^{st}$ Fick's law expression for the diffusion across the dialysis membrane $$\text{Flux} = \frac{dq_r}{dt} = D\frac{A(C_f - C_r)}{\delta} \quad (1)$$

yields an expression that allows for an estimation of the apparent diffusion coefficient (D):

$$\ln[q_f^0 - C_r(V_f + V_r)] = \ln q_f^0 - Kt \quad (2)$$

$$\text{where } K = DA(V_f + V_r)/V_f V_r \delta \quad (3)$$

Herein, q(t) and C(t) are the drug quantity and concentration, respectively, and subscripts f and r designate the feed and receiver solution, respectively.

Having defined the ranges of concentrations where the diffusion coefficient of either doxorubicin or PLURONIC® was independent of the drug initial concentration $C_f^0$, we used the microgel loading that did not exceed these ranges. A known mass of microgel particles with a known loading (U, see above) suspended in 10 mM Tris buffer (pH 7.0) was placed in the feed chamber resulting in an initial drug quantity in the system, $Q_0$. Assuming that the drug decay in the microgel particles can be approximated by a single-exponential (i.e., first-order) kinetics $Q(t) = Q_0 e^{-K_1 t}$, the Fick's law expression (1) can be rewritten as $$\text{Flux} = \frac{dC_r}{dt} = \frac{DA}{\delta V_r}\left[\frac{Q_0}{V_f}(1 - e^{-K_1 t}) - C_r\left(\frac{V_r}{V_f} + 1\right)\right] \quad (4)$$

and solved with respect to $C_r$ as follows:

$$C_r = \frac{Q_0}{V_f + V_r}\left[1 - e^{-Kt} - \frac{DA(V_f + V_r)}{\delta V_f V_r(K - K_1)}e^{-Kt} - \frac{DA(V_f + V_r)}{\delta V_f V_r(K - K_1)}e^{-K_1 t}\right] \quad (5)$$

At long dialysis times and $Kt \gg K_1 t$, eq(5) can be simplified:

$$\ln\left[\frac{Q_o}{V_f + V_r} - C_r\right] = \ln\left[\frac{DAQ_o}{\delta V_f V_r(K - K_1)}\right] - K_1 t \quad (6)$$

Equation (6) indicates that a plot of $\ln[Q_0/(V_f + V_r) - C_r]$ vs time should be a straight line that yields $K_1$. We used equations (2) and (3) to calculate the permeability of the dialysis membrane in experiments without microgels, and equation (6) to estimate $K_1$ in experiments with drug-loaded microgels.

Results

Figure 5:
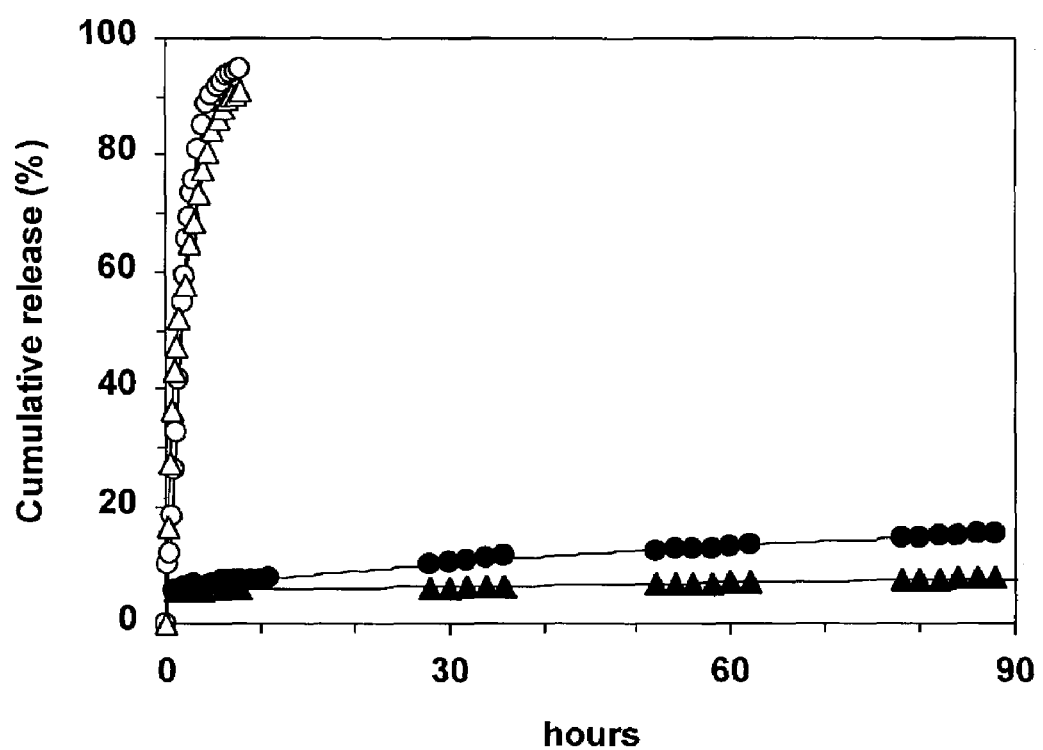
FIG. 5 shows the kinetics of the release of doxorubicin and PLURONIC® L61 through dialysis membrane with and without a responsive microgel described in Example I.

Kinetics of the release of doxorubicin and PLURONIC® L61 through dialysis membrane with and without microgels are compared in FIG. 5 (Kinetics of cumulative release of doxorubicin (circles) and PLURONIC® L61 (triangles) through the dialysis membrane with (filled points) and without (open points) microgels in the feed chamber at 37° C. Receiver chamber comprised 10 mM Tris buffer (pH 7.0) in all cases. Initial doxorubicin concentration in the feed 110 µg/mL (open circles) and 20 mg/mL (filled circles), initial PLURONIC® L61 concentration in the feed 20 mg/mL (open triangles) and 22 mg/mL (filled triangles). Microgels used in the feed were composed of PLURONIC® F127 and poly(acrylic acid)).

As shown in FIG. 5, loading of the corresponding drugs into microgels affected the kinetics of release greatly. Without microgels, almost 100% of the drug was released within less than a day, while the drugs loaded into microgels exhibited slow, sustained release kinetics.

Figure 6:
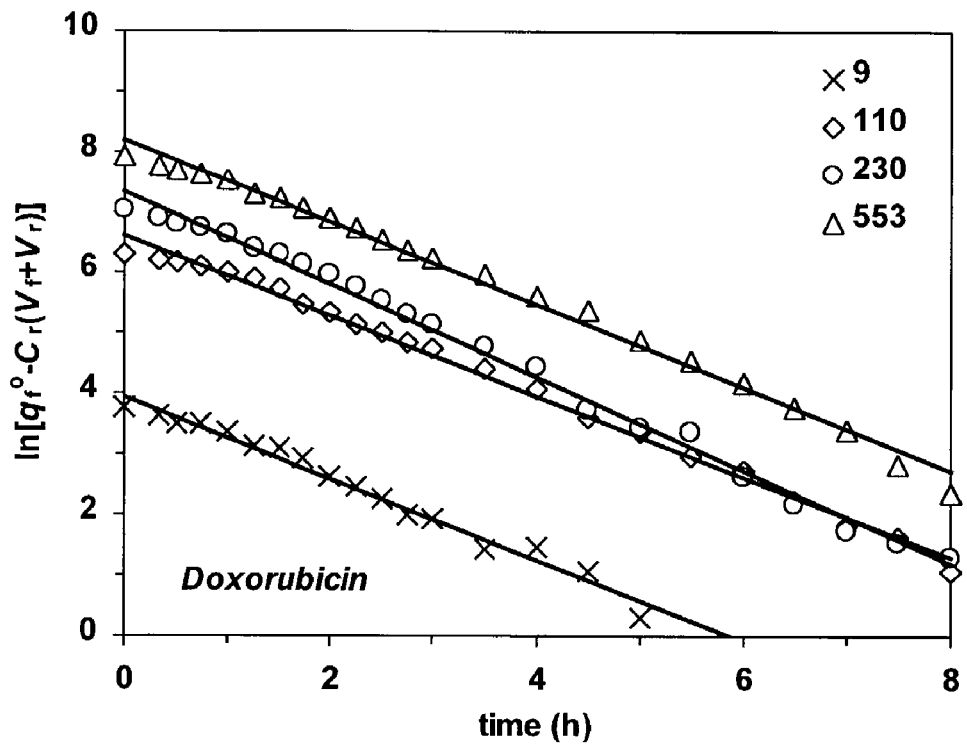
FIG. 6 shows the kinetics of the drug diffusion in the control experiment described in Example I.
Figure 6:
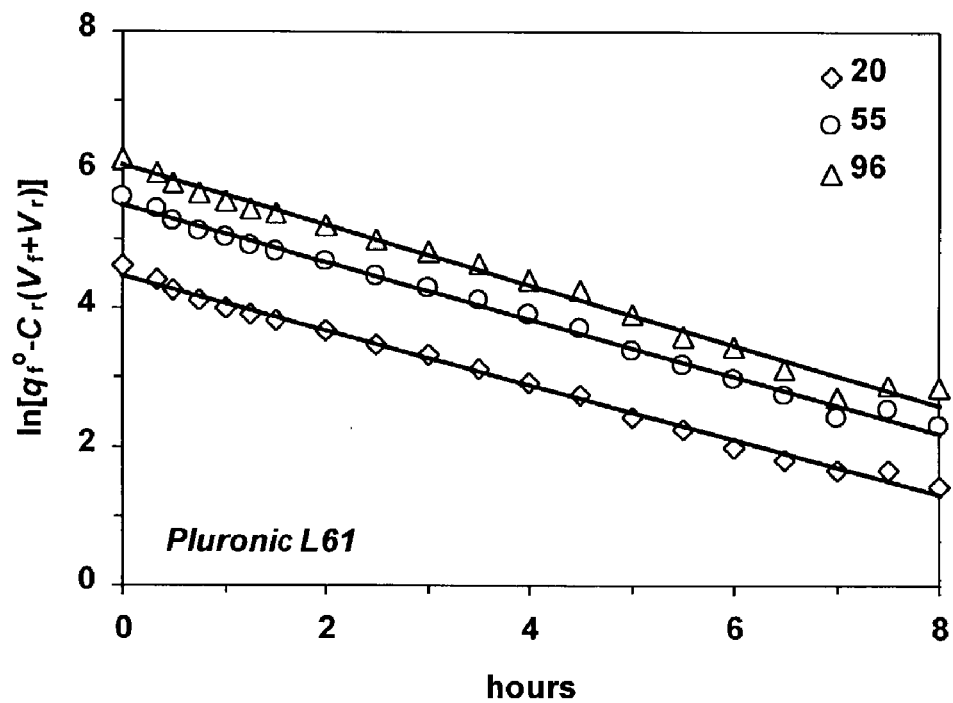

In the control experiments, we measured permeability of the dialysis membrane for doxorubicin and PLURONIC® L61 without loading into microgels. A range of initial drug concentrations in the feed solutions was explored, in order to verify the independence of the effective membrane permeability of the $q_f^0$, as is required if the change of the solute size (i.e. aggregation and/or micellization) is absent. FIG. 6 illustrates kinetics of the drug diffusion through the dialysis membrane as functions of the initial drug concentrations in the feed. The effective membrane permeability constant, K, was found from the slopes of the corresponding linear fits using equation (2). Thus obtained K values were equal to 0.70±0.048(4) and 0.41±0.019(3) $h^{-1}$ $\mu g^{-1}$ for doxorubicin and PLURONIC® L61, respectively. Given very close K values (standard error below 7% and 5% for doxorubicin and PLURONIC® L61, respectively) obtained within the studied ranges of $C_f^0$, we concluded that aggregation was absent within those ranges. Using mean K and measured membrane thickness (δ) values, we obtained the effective diffusion coefficients (D) of 2.4×10⁻⁵ and 1.4×10⁻⁵ cm²/s for doxorubicin and PLURONIC® L61, respectively (eqn (3)). These values are reasonably close to D of the corresponding solutes in water, indicating that the chosen dialysis membrane does not constitute any significant diffusional barrier to these solutes in their non-aggregated state. FIG. 6 shows the kinetics of doxorubicin and PLURONIC® L61 release through the dialysis membrane from an aqueous feed solution at 37° C., expressed in terms of equation (2). Numbers stand for $C_f^0$, μg/mL. Corresponding linear fits ($R^2$>0.99 in all cases) were used to calculate (eqn(2)) the effective membrane permeability constant, K.

Having defined the membrane permeability, we proceeded to the drug release study from the microgels. Kinetics of doxorubicin release from the microgels are shown in FIG. 7. The effective release constants ($K_1$) for doxorubicin were measured to be (14.2±0.36)×10⁻³ and (22.8±0.49)×10⁻³ $h^{-1}$ $\mu g^{-1}$ for microgels based on PLURONIC® F127-PAA-EGDMA and PLURONIC® L92-PAA-EGDMA, respectively. FIG. 7 shows the kinetics of doxorubicin release through the dialysis membrane from microgels at 37° C., expressed in terms of equation (6). Numbers stand for $C_f^0$ in μg/mL. The data points were fitted to linear fits ($R^2$>0.98 in all cases) with the slopes used to calculate (eqn(6)) the effective release constant, $K_1$. In A, the gels used in feed consisted of PLURONIC® F127 and PAA, whereas in B, the gels consisted of PLURONIC® L92 and PAA. The effective degree of the gel cross-linking was 1 mol % throughout.

Figure 8:
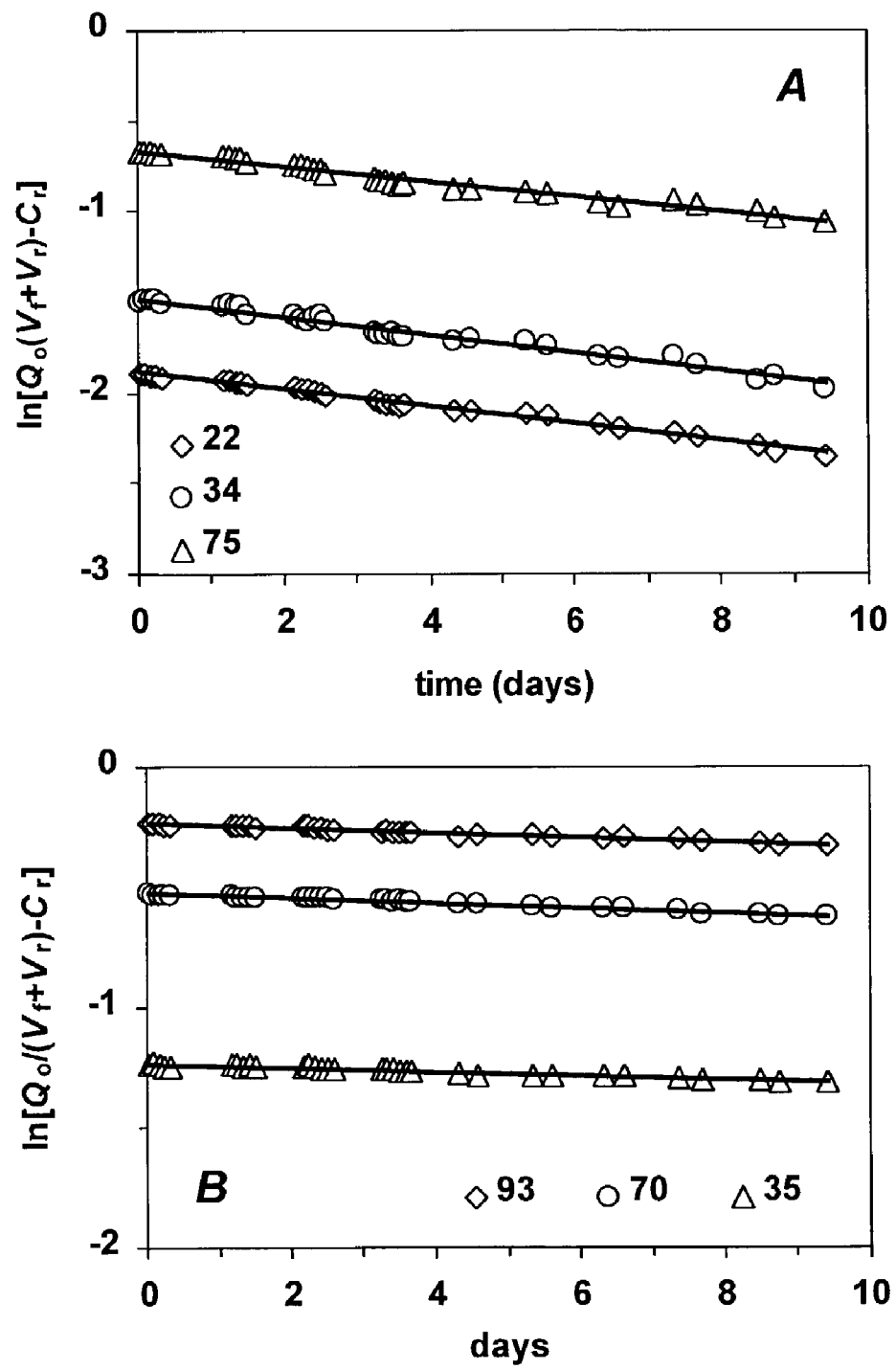
FIG. 8 shows a very slow, sustained release of PLURONIC® L61 from an example responsive microgel of the present invention.

Kinetics of PLURONIC® L61 release are presented in FIG. 8 which shows the release through the dialysis membrane from microgels at 37° C., expressed in terms of equation (6). Numbers stand for $C_f^0$ in μg/mL. The data points were fitted to linear fits ($R^2$>0.97 in all cases) with the slopes used to calculate (eqn(6)) the effective release constant, $K_1$. In A, the gels used in feed consisted of PLURONIC® F127 and PAA, whereas in B, the gels consisted of PLURONIC® L92 and PAA. The effective degree of the gel cross-linking was 1 mol % throughout.

The effective release constants ($K_1$) for the PLURONIC® were measured to be (2.1±0.18)×10⁻³ and (0.44±0.046)×10⁻³ $h^{-1}$ $\mu g^{-1}$ for microgels based on PLURONIC® F127-PAA-EGDMA and PLURONIC® L92-PAA-EGDMA, respectively. FIG. 8 shows that a very slow, sustained release of the PLURONIC L61® was achieved within at least 10 days, with cumulative concentrations reached in the receiver solution ($C_r$) that did not exceed 10–14% of the initial loading, $C_f^0$. The exceptionally low release rate of the PLURONIC® L61 can be explained by the formation of mixed micelles between added PLURONIC® L61 and PLURONIC® covalently grafted to the PAA network in the process of synthesis. Such mixed, immobile micelles can provide thermodynamically stable environment for the PLURONIC® solute, making its effective partition coefficient between micelles and water to be very low. This notion is supported by the observation that the release rate from the gels from L92-PAA-EGDMA was about 5-fold higher than from the gels containing PLURONIC® F127 bonded to PAA. Formation of stable mixed micelles between relatively hydrophobic PLURONIC®s L61 and L92 can be favored than between PLURONIC® L61 and relatively hydrophilic F127 (for PLURONIC® properties, see Table 1, supra).

Example II

Microgel Synthesis

Nonionic copolymer PLURONIC® F127 NF was obtained from BASF Corp. and used without further treatment. It has a formula $EO_{100}PO_{65}EO_{100}$, nominal molecular weight 12600, molecular weight of PPO segment 3780, 70 wt % of EO, and cloud point above 100° C. Acrylic acid (99%) (vinyl monomer), ethylene glycol dimethacrylate (EGDMA) (98%) (divinyl cross-linker), dodecane (99+%) (solvent), and 4,4'-azobis(4-cyanovaleric acid) (75+%) (azo initiator) were purchased from Aldrich Chemical Co. and used as received. Lauroyl peroxide (97%) (redox initiator) was obtained from Fluka Chemie AG, Switzerland. Poly (vinylpyrrolidinone-co-1-hexadecene) (Ganex V-216) (dispersion stabilizer) was obtained from International Specialty Products and used as received. All other chemicals, gases and organic solvents of the highest purity available were obtained from commercial sources.

Synthesis was carried out on a laboratory scale in an adiabatic mode. Acrylic acid (vinyl monomer) (40 mL) was partially neutralized by addition of 5M NaOH aqueous solution (0.5 mL). PLURONIC® F127 NF (23.4 g) was dissolved in the resulting solution under nitrogen and a desired amount of ethylene glycol dimethacrylate (EGDMA) (divinyl cross-linker) was added. Amounts of EGDMA ranged from 1.1 μL to 1.1 mL and the molar ratio of the EGDMA to acrylic acid set in the reaction mixture designates the degree of cross-linking of the microgels in what follows. Lauroyl peroxide (100 mg) and 4,4'-azobis(4-cyanovaleric acid) (100 mg) were dissolved in 2 mL of acrylic acid and added to the solution of PLURONIC® F127 NF in acrylic acid. The resulting solution was deaerated by nitrogen bubbling for 0.5 h and added to a 3-necked 0.5-mL flask containing 1 wt % solution of Ganex V-216 in dodecane (200 mL). The flask was vigorously stirred by a mechanical stirrer and deaerated by constant nitrogen purge from the bottom. Then the flask was heated to 70° C. using an oil bath and kept at that temperature under stirring and nitrogen purge. After about 1 h, formation of white particles was observed on the flask walls. The reaction was continued at 70° C. for another 3 h. Then the reactor was disassembled, and the contents of the reactor were filtered using Whatman filter paper (retention size 10 micron). The microgel particles were extensively washed by hexane and dried under vacuum.

Spherical particles were observed under microscope. Particle sizing was performed in hexane using a ZetaPlus Zeta Potential Analyzer (Brookhaven Instruments Co.). A typical batch containing 1 mol % cross-linking was measured to have effective Example III Microgel Superabsorbent Properties The ability of microgels to absorb water was estimated using a volumetric method. Single microgel particles were placed into glass capillary tubes (internal diameter 1–1.2 mm) using suction pressures applied by an Ultramicro Accropet filler/dispenser via rubber connector. The tubes were placed into a homemade glass thermostatted cuvet and observed under an inverted microscope equipped with a microscaler and a video monitor. Similar experimental setup was described in Eichenbaum, G. M., et al., *Macromolecules*, 1998, 31, 5084–5093. The boundaries of the spherical particles were fitted with the microscaler and a particle diameter was measured with an accuracy of ±0.5 µm or better. Initially, a diameter of a dry particle ($d_0$) was measured, then the capillary tube was gently filled with deionized water (pH adjusted by 5 M NaOH) immersed into a reservoir of the same solution. The diameter of the swollen particle ($d_s$) was measured at a given temperature. The particles were allowed to swell for 24 h, after which no changes in the particle size were observed at any temperature. The equilibrium volume ratio $S=V/V_0$ was defined as $S=(d_s/d_0)^3$. Measurements at given pH and temperature were conducted with 5 different particles in different capillary tubes. Average S values are reported throughout.

Figure 9:
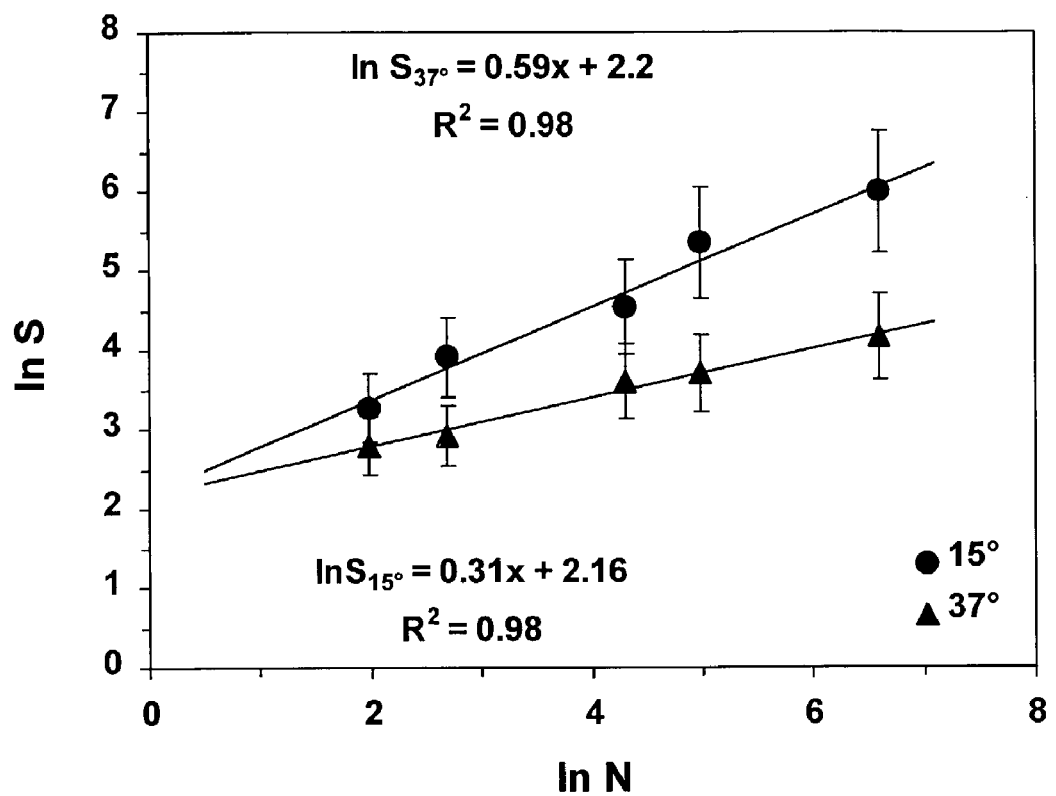
FIG. 9 shows the results of equilibrium swelling experiments, e.g., high absorbency as a function of the subchain length.

The results of equilibrium swelling experiments with microgels cross-linked by EGDMA are shown in FIG. 9. The length of subchain (i.e. length of the chain between cross-links) N defined as in Bromberg, L., et al., *J. Chem. Phys.*, 1997, 106, 2906–2910.

$$N=[a^6 c_{x1}(c_{x1}+c_m)]^{-1}$$

where $a=10 v_{x1} v_m$, $v_{x1}=0.2$ M$^{-1}$ is the molar volume of the cross-linker (EGDMA), and $v_m=0.063$ M$^{-1}$ is the molar volume of the monomer (acrylic acid).

FIG. 9. Equilibrium swelling of microgel particles in deionized water as a function of the length of subchain. pH 7.0. The results shown in FIG. 9 indicate that at 15° C., swelling of the microgels corresponds to the swelling of other superabsorbents and is governed by elasticity of the permanent cross-links and osmotic term corresponding to the electrostatic repulsion of the chains. At 15° C., the swelling ratio S scales as $S \propto N^{0.6}$, which according to the Flory-Huggins theory is indicative of the Gaussian chain statistics, typical for covalently cross-linked gels. However, at 37° C., elasticity of the microgel becomes higher due to the appearance of additional cross-links (PLURONIC® chains with hydrophobic poly(ethylene oxide) segments). The swelling ratio scales as $S \propto N^x$, with x<0.6 meaning non-Gaussian chain statistics. Overall, the results in FIG. 9 show i) high absorbency (swelling ratio in DI water up to 300 and higher), and ii) useful temperature sensitivity of water uptake.

Example IV pH-Sensitivity of Microgel Swelling

Figure 10:
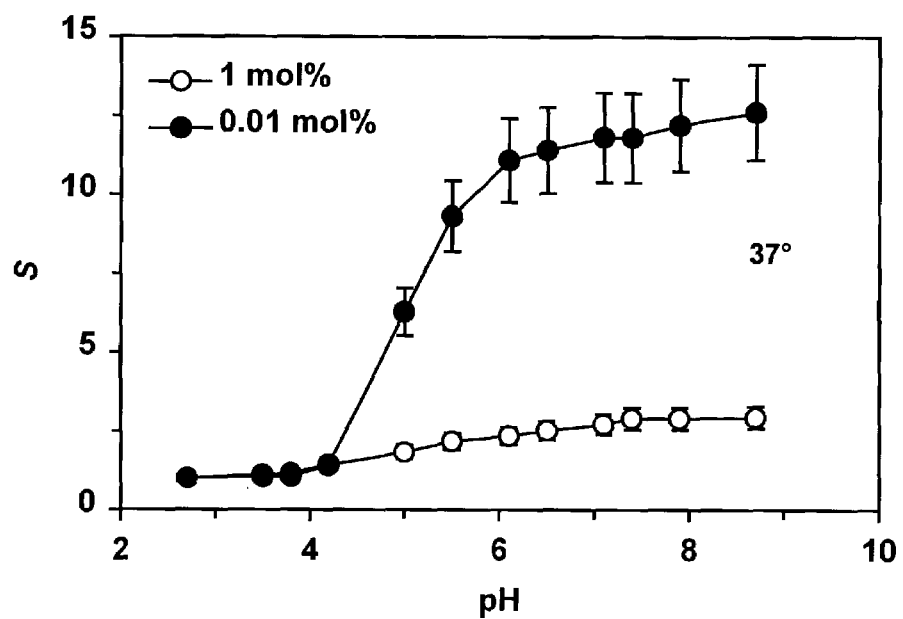
FIG. 10 shows equilibrium swelling of microgel particles in deionized water at 15° and 37° C. as a function of pH. Degree of cross-linking in molar percent is indicated.
Figure 10:
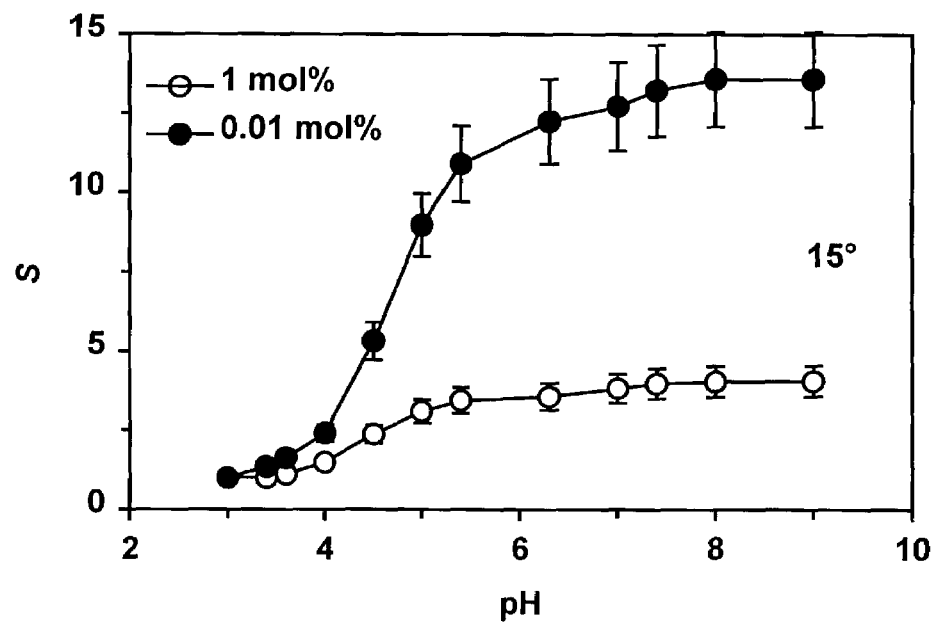

Experiments were conducted as described in Example III, except the microgel particles were allowed to equilibrium swell at a certain pH$_0$, and temperature to yield a d$_0$. Then the aqueous solution was gently removed from the glass tube by filter paper and the tube with the microgel particle was immersed into a solution of different pH$_x$ and equilibrated there overnight. Finally, the tube with the microgel particle filled with the solution of pH$_x$ was inserted into the cuvet and thermostatted at desired temperature to yield an equilibrium microgel diameter d$_x$. The equilibrium volume ratio $S=V_x/V_0$ was defined as $S=(d_x/d_0)^3$. FIG. 10 shows equilibrium swelling of microgel particles in deionized water at 15° and 37° C. as a function of pH. Degree of cross-linking in molar percent is indicated. Results in FIG. 10 show dramatic increase in swelling above pH 3.8–4.1, corresponding to pKa of poly(acrylic acid). Hence, our microgels would be collapsed at pH 1–2 and fully swollen at pH 7.4. This is a useful property applicable in oral or colonic drug delivery.

Example V

Temperature-sensitivity of Microgel Swelling

Figure 11:
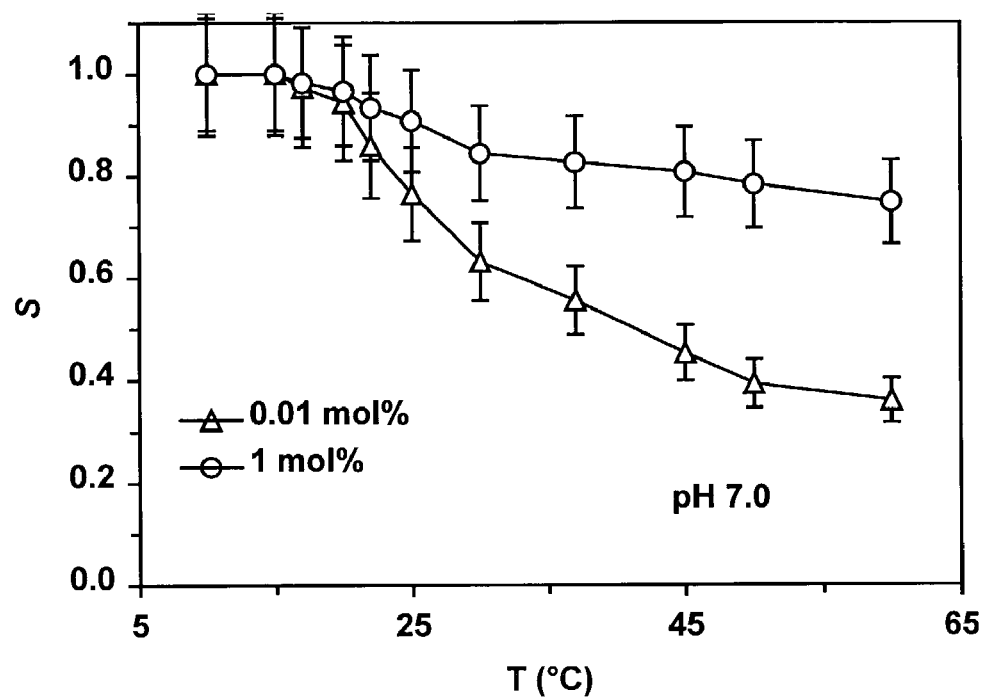
FIG. 11 shows equilibrium swelling of microgel particles in deionized water at pH 7.0 as a function of temperature. Degree of cross-linking in molar percent is indicated.

Experiments were conducted as described in Example IV and the results are shown in FIG. 11 illustrating equilibrium swelling of microgel particles in deionized water at pH 7.0 as a function of temperature. Degree of cross-linking in molar percent is indicated. These results demonstrate useful temperature-sensitivity of the microgel swelling.

Example VI

Temperature-sensitivity of Solubilization of Hydrophobic Compounds

Figure 12:
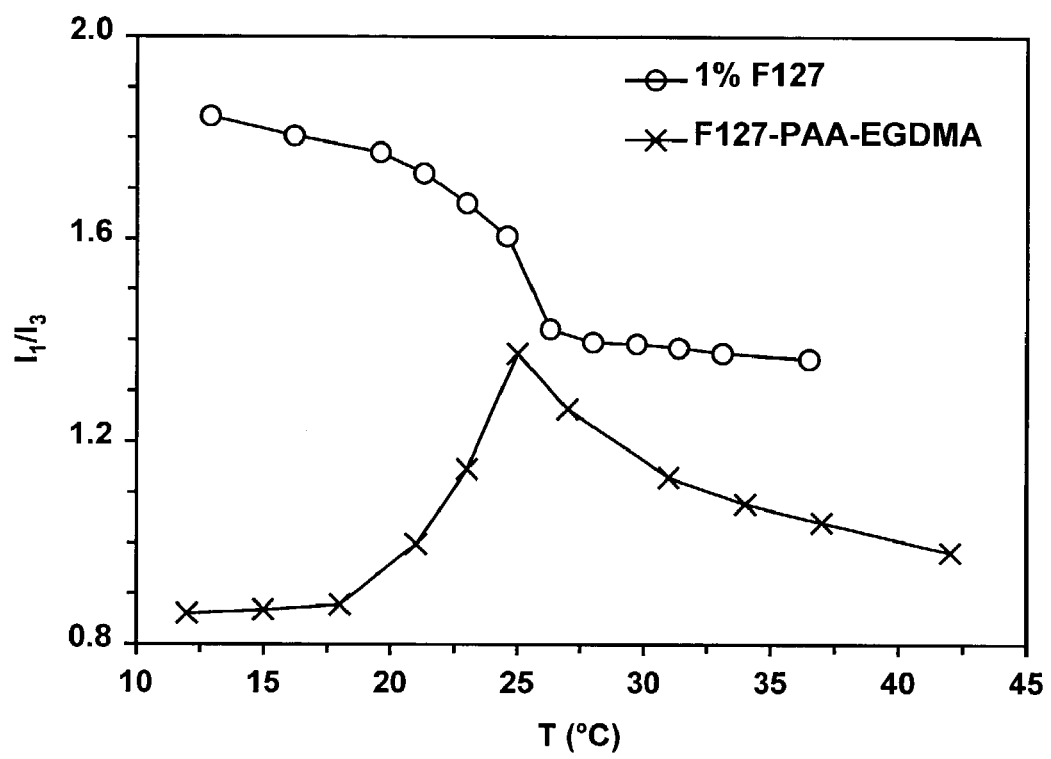
FIG. 12 shows the effect of temperature on hydrophobic compounds in responsive microgel suspension.

Solubilization of pyrene, a well-known hydrophobic fluorescent probe, was used to reveal formation of aggregates within microgel particles capable of solubilizing hydrophobic compounds. The microgel particles were suspended in DI water and pH of the suspension was adjusted to 7.0 using 10 M NaOH. A stock solution of 1 mM pyrene in absolute methanol was prepared, from which 1–3 µL were added to an aerated 1 wt % suspension resulting in 0.6 µM pyrene concentration. The sample was then allowed to equilibrate for 20 min at a given temperature and emission ($\lambda_{ex}=335$ nm) spectra were recorded using a stirred, thermostatted quartz cell with a 1-cm path length. The spectra were measured under controlled temperature conditions using a Shimadzu Model RF-5301 PC spectrofluorophotometer (slit widths of 1.5 nm). The ratio of the intensities of the first (373 nm) to the third (384 nm) vibronic peak ($I_1/I_3$) in the emission spectra of the monomer pyrene were used to estimate the polarity of the pyrene microenvironment. For comparison, 1 wt % solutions of PLURONIC® F127 NF were prepared and studied in the same fashion. The effect of temperature on $I_1/I_3$ of pyrene in microgel suspension (1 mol % cross-linking) or in polymer solutions is presented in FIG. 12. FIG. 12 shows the effect of temperature on the ratio of the first-to-the-third vibronic band intensities ($I_1/I_3$) of pyrene in 1 wt % microgel suspension or in 1 wt % PLURONIC® F127 solution. Microgel with 1 mol % cross-linking is designated F127-PAA-EGDMA. pH 7.0 throughout. As is seen, in 1.0% PLURONIC® F127 solutions, for example, the $I_1/I_3$ sharply declines above 20° C., which is the critical micellization temperature (CMT). Alexandridis, P., et al., *J. Am. Oil Chem. Soc.* 1995, 72, 823. At temperatures below CMT, the $I_1/I_3$ is only slightly below the I1/I3 in water, indicating high polarity of the pyrene environment and lack of solubilization. The microgel suspension has I1/I3 values that are significantly less than in the corresponding Pluronic solution, indicating lesser polarity and higher capability of solubilization throughout the temperature range. The I1/I3 in microgel suspension is low at T<20° C. (which corresponds to the critical micellization temperature of PLURONIC® and increases in the temperature range 20–26° C. Above 26° C., the $I_1/I_3$ decreases. At low temperatures, hydrophobic domains exist in the microgels that are getting solubilized into hydrophobic micelle-like aggregates of Pluronic within microgels. Once micelles are formed above 26° C., they provide a hydrophobic environment for the pyrene. The temperature-responsive mode of solute solubilization by microgels is useful for medicinal and cosmetic formulations.

Example VII

Loading of Ionic and Hydrophobic Drugs
Water-Soluble Solutes

The maximum loading level of doxorubicin, mitoxantrone, and mitomycin C, for example, into microgels was measured using a Millipore Ultrafree-MC Centrifugal Filter Device (Millipore, Co.). A microgel was suspended in Tris buffer (5 mM, pH 7.0) and 50 μL of the suspension (2 mg gel/mL buffer) was equilibrated with 3.0 mM stock solution of a drug (450 μL) for 16 h while shaking 44,45. Shaking was performed using a KS10 orbital shaker (BEA-Enprotech Corp., Hyde Park, Mass.) in an environmental chamber at 37° C. In the case of doxorubicin, pH of the microgel suspensions equilibrated with the stock drug solution was varied by addition of small amounts of 5 M NaOH or HCl solutions, and temperature was varied from 15 to 45° C. After equilibration, the microgel particles were filtered off by centrifugation (10000×g, 0.5 h) and supernatant was assayed for drug concentration. A Shimadzu Model 1600 PC spectrophotometer with a temperature-controlled quartz cuvette (path length 1 cm) was used for electronic absorption measurements. The extinction coefficients of doxorubicin ($\lambda=482$ nm) and mitoxantrone ($\lambda=614$ nm) were determined at pH 7.0 to be 12200 and 22100 M-1 cm-1, respectively. The concentration of mitomycin C was assayed by HPLC using a Capcell Pak MF Ph-1 (100×4.6 mm I.D., particle size 5 μm) column (Phenomenex, Torrance, Calif.). The HPLC was a Hewlett-Packard 1090 system with an autosampler and a variable wavelength UV detector controlled by the HPLC Chemstation software (Hewlett-Packard). Deionized water was used as a mobile phase (flow rate, 1 mL/min, injection volume, 25 μL), and detection was carried out at 365 nm 47. Typical retention time of the mitomycin C was 4.88 min.

The drug uptake was expressed as:

U (mmol drug/g gel)=[(Ac—Ar)/Ac]VCs/Mgel, where Ac and Ar are the absorbance or HPLC readings in the appropriately diluted stock solution and in the system equilibrated with microgel, respectively, V=0.5 ml is the total volume of the system, Cs=3 μmol/mL is the concentration of the stock solution, and Mgel=0.1 mg is the microgel mass. The U values were measured in triplicate for each drug and for each temperature, pH, and gel, respectively. In a control series of experiments, equilibration of 6 μmol/mL doxorubicin with microgels for 1 week yielded U values close (within experimental error) to the ones obtained with 3 μmol/mL solutions under otherwise identical conditions. This ensured equilibrium U values.

Hydrophobic Solutes

The loading of taxol into microgels was measured by equilibrating taxol adsorbed onto steel beads with the 1 wt % suspension of microgels (pH 7.0). Stainless steel beads (1–3 mm diameter) were soaked in 10 mM solution of taxol in acetonitrile, following by stripping off the solvent in a rotary evaporator. The beads were used in order to enhance the area of contact between microgel suspension and taxol. The beads were separated into several fractions. One fraction was added to a polypropylene vial containing the microgel suspension (0.5 mL) and the vial was gently shaken in a horizontal position in an environmental chamber at 20 or 37° C. Then the beads were recovered from the suspension by using a magnet. The beads were then dried under vacuum and placed into acetonitrile (0.5 mL), where taxol was extracted after shaking overnight. The solvent fraction was assayed for taxol concentration using HPLC. The control fraction of loaded beads was subjected to the extraction without equilibration with the microgel suspension. The solubility of taxol in water was measured at 37° C. by sonicating 5 mg of the drug suspension in 0.5 ml water placed in a polypropylene vial for 15 s followed by centrifugation at 10000 g for 3 min. The supernatant was then removed, evaporated under vacuum, the taxol traces were dissolved in acetonitrile and assayed by HPLC. Taxol concentrations were measured in triplicate using HPLC system described above. The chromatography assay comprised the use of a Capcell Pak C18 UG 120 (150×4.6 mm I.D., particle size 3 μm) column (Phenomenex), acetonitrile-0.1% phosphoric acid in DI water (55:45 v/v, 1.3 mL/min) as a mobile phase, and UV detection at 227 nm.

Typical retention time of the taxol peak was 3.46 min.

Results

Figure 13:
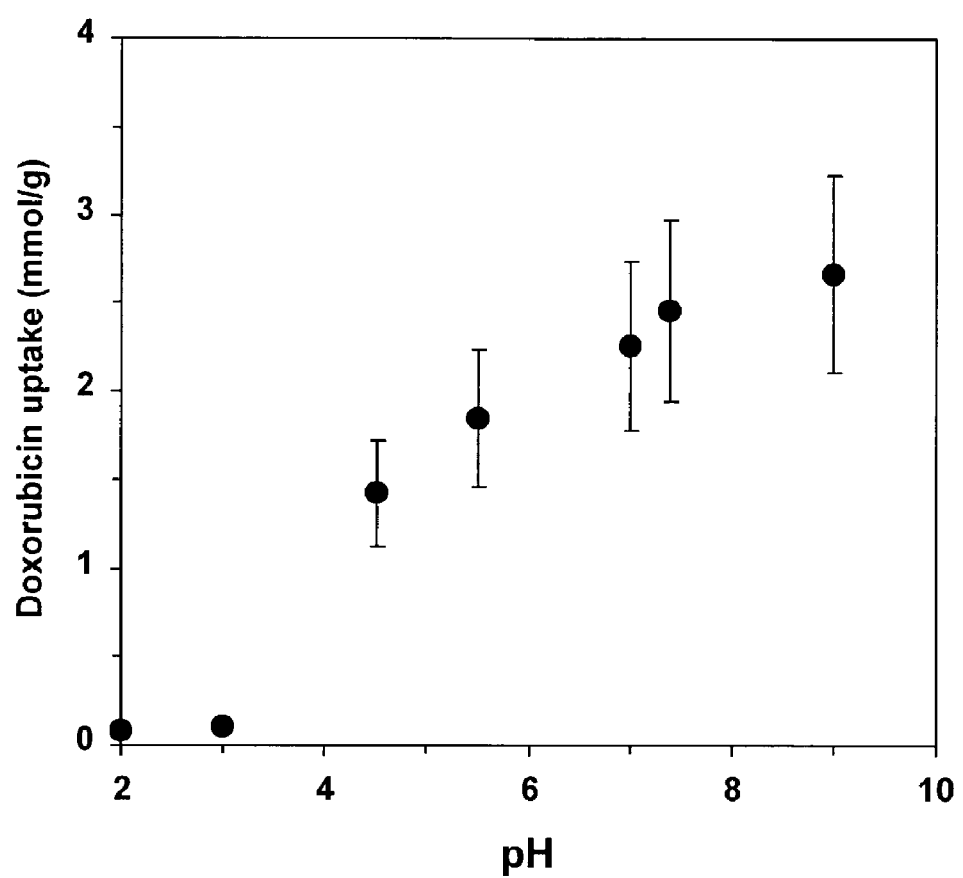
FIG. 13 shows the equilibrium uptake of doxorubicin by microgels of the present invention as a function of pH at 37° C.

Three cationic and one uncharged drugs were loaded onto the microgels. All of these compounds are currently in clinical use as anticancer drugs. Doxorubicin, mitoxantrone, and mitomycin C are mono-, di-, and trivalent cationic weak bases, respectively. FIG. 13 shows the equilibrium uptake of doxorubicin by microgels (crosslinking (XL)=1 mol %) as a function of pH at 37° C.

Table 2 lists molecular weights, n-octanol-to-water partition coefficients (P), and equilibrium uptake of the drugs into the microgels characterized by XL=1 mol % and maximum ion-exchange capacity of 6.12 mmol/g (measured by bulk titration as described herein). All of the uptake values in Table 2 were less than or equal to maximum microgel capacity for protons. A pronounced dependence was observed with the weak bases: the smaller, more hydrophilic, and more charged solutes had the higher loading into the microgels.

TABLE 2

Properties of anticancer drugs and their equilibrium uptake by the PLURONIC ®-PAA microgels (cross-linking ratio, XL = 1 mol%, ion-exchange capacity, 6.12 mmol/g) at pH 7.0.

| Drug | MW[a] | Log P | Charge | Uptake ±SD, mmol/g |
|---|---|---|---|---|
| Mitomycin C | 334.1 | −0.4 | 3 | 5.31 ± 1.86(37° C.) |
| Mitoxantrone | 44.2 | 0.24[b] | 2 | 3.70 ± 0.56(37° C.) |
| Doxorubicin | 543.5 | 1.85 | 1 | 2.97 ± 0.33(20° C.) |
|  |  |  |  | 2.26 ± 0.37(37° C.) |
| Taxol | 853.3 | 4 | 0 | (2.27 ± 0.90) × $10^{-3}$ (20° C.) |
|  |  |  |  | (6.97 ± 0.87) × $10^{-3}$(37° C.) |

[a]Molecular weights are given for free bases, and not hydrochloride salts.
[b]Calculated using ClogP Program.

The characteristic increase in taxol loading capacity at temperatures above CMT provides additional evidence to the mechanism of taxol solubilization into micelle-like aggregates within microgels. The micelles in PLURONIC®-PAA solutions typically have solubilizing capacity higher than the small hydrophobic domains existing below CMT.

The solubilizing capacity of the microgels for taxol is at least equal to that of PLURONIC®-PAA micelles for other hydrophobic solutes such as steroid hormones. The ability of microgels to effectively load and hold taxol, combined with mucoadhesive properties is a feature important for localized delivery.

General trends important for drug loading via ion-exchange mechanism were studied using the potent chemotherapeutic drug doxorubicin. As the degree of carboxyl group ionization increases with pH, the ion-exchange capacity of the microgels increase, reaching about half of the maximum capacity found by titration, indicating that the loading of doxorubicin can be limited by the available free volume of the network. Notably, the pH-dependencies of the equilibrium swelling and doxorubicin loading coincide. Similar result was observed with poly(methacrylic acid) microgels. The effects of steric "crowding" of the drug within the microgel network and the availability of the carboxyls for the ion-exchange are highlighted by the effects of temperature and cross-linking density. The collapse of the microgels at elevated temperature due to the appearance of physical cross-links leads to lesser volume of the microgel network available for hosting the drug, and thus lower equilibrium loading at higher temperatures. Analogously, the longer subchain allowing for the looser network and higher swelling leads to the higher equilibrium loading of doxorubicin. The very high overall capacity of the microgels for doxorubicin (2 M and higher), will allow proper chemotherapeutic drug delivery. Microgels loaded with both taxol and doxorubicin, for example, is a feature embodiment of the microgels described herein.

Example VIII

Doxorubicin Transport Study Across Gastrointestinal Caco-2 Layers Materials and Cell Culture Caco-2 cells (American Type Culture Collection, Rockville, Md.) were maintained at 37° in Dulbecco's Modified Eagle Medium (DMEM) containing N-(2-hydroxyethyl)piperazine-N'-(2-ethanesulfonic acid) (HEPES, 25 mM), glucose (4.5 g/L), and supplemented with 10% (v/v) fetal bovine serum, 1% nonessential amino acids, L-glutamine (2 mM), penicillin (100000 U/L), and streptomycin (100 mg/L), in an atmosphere of 10% $CO_2$ and 90% relative humidity. The cell line (passage numbers from 70 to 85) was subcultured by trypsinization every week and the medium was replaced every other week. Cells were passaged at 90% confluency using a 0.25% trypsin/0.20% ethylene diamine tetraacetic acid (EDTA) solution. All cell culture products were received from GIBCO™ (Invitrogen Corporation, Carlsbad, Calif.). Hank's balanced salt solution (HBSS, composition: $KH_2PO_4$, 0.44 mM; KCl, 5.37 mM; $Na_2HPO_4$, 0.34 mM; NaCl, 136.9 mM; D-glucose 5.55 mM) buffered with 30 mM HEPES at pH 7.2, 3-(4,5-Dimethylthiazol-2-yl)-2,5-diphenyltetrazolium bromide, and Verapamil were obtained from Sigma Chemical Co. (St. Louis, Mo.). D-[1-$^{14}$C]-mannitol (250 mCi/mmol, 99+% radiochemical purity, MW 182.2) was obtained from PerkinElmer Life Sciences (Boston, Mass.). Carbopol® 934 NF polymer was received from Noveon, Inc. (Cleveland, Ohio). Microgels comprising copolymers of poly(acrylic acid) and Pluronic F127 NF or Pluronic L92 cross-linked by ethylene glycol dimethacrylate at effective cross-linking density of 0.1 mol % were synthesized by a free-radical suspension polymerization as described previously [9]. The microgels were purified from admixtures of acrylic acid and unattached Pluronic by Soxhlet extraction and dialysis [9]. The purified microgels were analyzed for residual unattached Pluronic as follows. A microgel suspension (10 wt %, 50 g) in deionized water was dialyzed for a week at 4° C. against deionized water (0.5 L) using a Spectra/Por® cellulose ester membrane (molecular weight cut-off 100,000, Spectrum®, Laguna Hills, Calif.). Then the dialysis bag was withdrawn and the dialyzate was lyophilized to dryness in 40-mL polypropylene tubes. Then the tubes were rinsed, with brief sonication, with total of 5 mL dimethylformamide, thereby concentrating the wash-outs, if any, 100-fold. The wash-outs were analyzed for the presence of Pluronic using HPLC. Liquid chromatography was performed using a Hewlett-Packard model 1050 chromatograph, a Dynamax model RI-1 analytical refractive index detector, and two PLgel 5 µm mixed 'D' columns in series. The analyses of the residual solids were run in DMF at 1.0 mL/min flow rate using poly(ethylene glycol) standards kit (Polysciences, Inc., Warrington, Pa.) for molecular weight calibration. The eluent was DMF (HPLC grade) at a flow rate of 1 mL min$^{-1}$. In the control assays, a 20 µg/mL concentration or lower of either Pluronic F127 or L92 could be detected. However, no Pluronic could be detected in the wash-outs, which means that the concentration of the unattached Pluronic was less than 0.01 wt % of the total Pluronic bonded onto microgels. The weight ratio of Pluronic to poly(acrylic acid) in purified microgels used in this study was determined as described elsewhere [7] to be 45:55. The microgels equilibrium swollen in deionized water (pH adjusted to 7.0) were subjected to particle sizing using an AccuSizer 780/SPOS (Christison Scientific Equipment Ltd., Gateshead, UK). The mean populations of the F127-PAA-EGDMA and L92-PAA-EGDMA microgels were of 54±22 and 23±9 µm size, respectively.

Transepithelial Transport of Doxorubicin

The drug-containing samples for the transport experiments were prepared as follows. A freeze-dried microgel was autoclaved at 121° C. for 15 min and suspended in serum-free DMEM, where it was allowed to equilibrate at 37° C. under gentle stirring overnight in sterile conditions. The suspension was centrifuged at 8000×g for 0.5 h and the supernatant was removed. The pellet was weighed and resuspended in fresh portion of serum-free DMEM of a known weight. Known amount of doxorubicin and Pluronic were dissolved in the suspension, which was allowed to equilibrate at 37° C. overnight, then snap-frozen and lyophilized. The powders were kept at −70° C. Before the transport experiments, a known amount of powder was reconstituted in DMEM and was allowed to equilibrate at 37° C. overnight. The composition of the drug-containing samples tested in the transport experiments is given in Table 3.

TABLE 3

Composition of the drug-containing donor media used in transepithelial transport experiments in the apical or basolateral compartments.[a]

| No. | Microgel composition[b] | Microgel concentration) µg/mL | Concentration of additive (beyond doxorubicin), µg/mL[c] |
|---|---|---|---|
| 1 | None (Control) | 0 | None |
| 2 | None | 0 | 100 (Pluronic L61) 0 (Verapamil) |
| 3 | None | 0 | 100 (Pluronic L92) 0 (Verapamil) |
| 4 | L92-PAA-EGDMA | 100 | None |

TABLE 3-continued

Composition of the drug-containing donor media used in transepithelial transport experiments in the apical or basolateral compartments.[a]

| No. | Microgel composition[b] | Microgel concentration) μg/mL | Concentration of additive (beyond doxorubicin), μg/mL[c] |
|---|---|---|---|
| 5 | L92-PAA-EGDMA | 100 | 100 (Pluronic L61) 0 (Verapamil) |
| 6 | L92-PAA-EGDMA | 100 | 100 (Pluronic L92) 0 (Verapamil) |
| 7 | F127-PAA-EGDMA | 100 | 0 |
| 8 | F127-PAA-EGDMA | 100 | 100 (Pluronic L61) 0 (Verapamil) |
| 9 | F127-PAA-EGDMA | 100 | 100 (Pluronic L92) 0 (Verapamil) |
| 10 | None | 0 | 0 (Pluronic) 9 (Verapamil) |
| 11 | L92-PAA-EGDMA | 100 | 0 (Pluronic) 9 (Verapamil) |
| 12 | F127-PAA-EGDMA | 100 | 0 (Pluronic) 9 (Verapamil) |

[a]Initial concentration of doxorubicin in the donor compartment was 100 μg/mL in all experiments
[b]Degree of cross-linking, XL = 0.1 mol% throughout
[c]Concentrations of added Pluronic L61 and L92 were arbitrarily chosen to result in effective Pluronic concentrations just below CMC [40, 41]. Concentration of added Verapamil was 20 μM [27].

Cells were seeded at a density of $(2-4) \times 10^4$ cells/cm² on top of Transwell™ polycarbonate filters (pore size, 0.4 μm; diameter, 24.5 mm; growth area, 4.71 cm²) from Costar (Cambridge, Mass.). The cells were grown for 3 weeks prior to the transport experiments and trans-epithelial electrical resistance (TEER) was measured using a Millicell-ERS device (Millipore, Bedford, Mass.) equipped with rod-shaped electrodes. The TEER data were corrected for background readings contributed by the blank filter and culture medium. Typical values of TEER were 800–850 Ωcm². Then the monolayers were rinsed twice by serum-free DMEM and the transport experiment commenced by replacing the medium at either the basolateral or the apical side of the monolayer with 2.5 mL of the serum-free DMEM containing doxorubicin (with or without microgels, see Table 3). Simultaneously, the medium on the other side was refreshed. The monolayers were incubated at 37° C. in 10% $CO_2$ atmosphere. Samples of 200 μL were taken from each side intermittently, and the drug concentration was measured in the samples withdrawn from the side opposite to the side of the drug application. The volumes withdrawn were immediately replaced with equal volumes of serum-free DMEM pre-equilibrated at 37° C. Each experiment was repeated four times. The TEER values were measured after the completion of each transport experiment and were shown to be equal to the initial TEER values obtained prior to the commencement of the experiment. The doxorubicin concentration was assayed using a Shimadzu Model RF-5301 PC spectrofluorophotometer ($\lambda_{excitation}$ 480 nm, $\lambda_{emission}$ 580 nm). Additionally, the concentration of doxorubicin in the medium was measured by HPLC using a Capcell Pak UG C18 (100×4.6 mm I.D., particle size 5 μm) column and a Universal Guard Cartridge System (Phenomenex, Torrance, Calif.). The HPLC was a Hewlett-Packard 1090 system with an autosampler and a ZETALIF laser induced fluorescence detector (ESA, Inc., Chelmsford, Mass.). Water/acetonitrile (70/30, pH 4) was used as the mobile phase (flow rate, 1 mL/min, injection volume, 5 μL), and detection was carried out using an Argon Ion laser (488 nm, 10 mW). Surface tension in microgel suspensions was measured using the Wilhelmy plate method (Sigma 701 automatic tensiometer, KSV Instruments, Ltd.). Temperature was controlled to ±0.05 C using a circulating water bath. The platinum Wilhelmy plate was washed with acetone, rinsed in Milli-Q water, and flamed until red-hot before each measurement.

The apparent permeability of the Caco-2 monolayer ($P_a$, cm/s) was calculated from the linearized time course of the doxorubicin fractional transport ($dI_t/dt$ in the fluorescence assay and $dC_t/dt$ in the HPLC assay) normalized to the effective surface area of the filter (A=4.71 cm²) and the initial fluorescence emission intensity reading ($I_o$) or initial doxorubicin concentration ($C_0$) in the donor (basolateral or apical) compartment of volume V=2.5 cm³:

$$P_a = \frac{dI_t/dt}{AI_o}V = \frac{dC_i/dt}{AC_o}V$$

Figure 14:
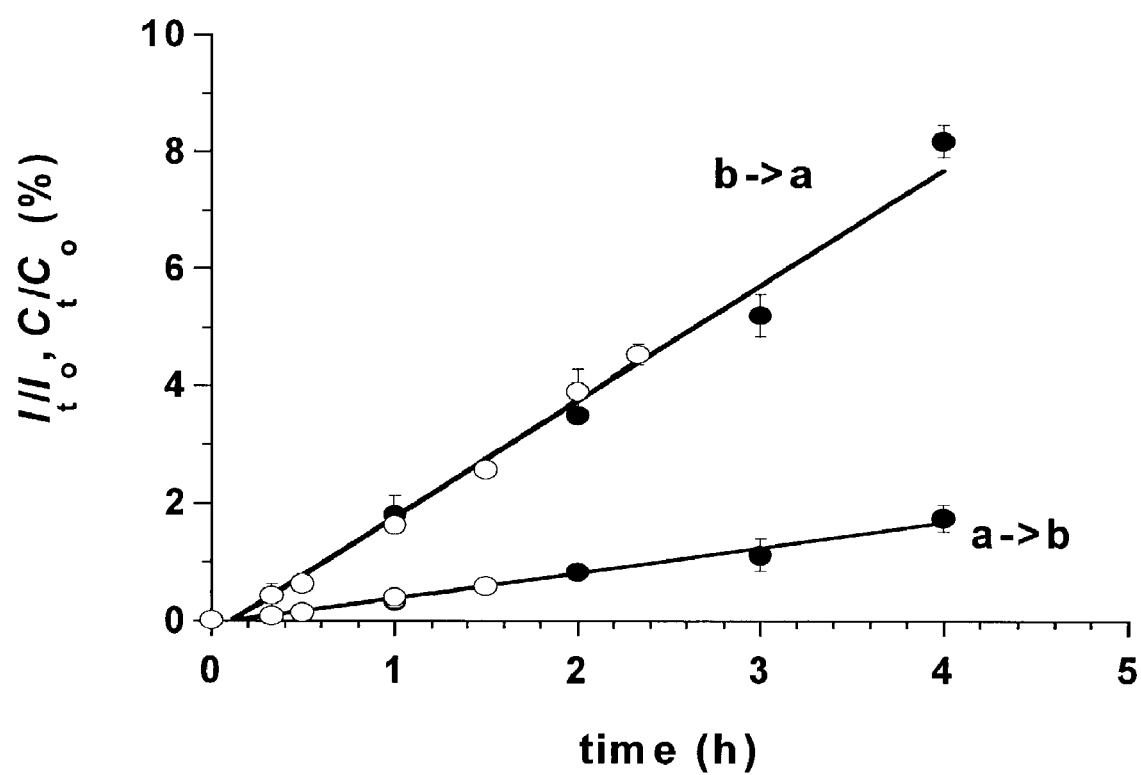
FIG. 14 shows transepithelial transport of doxorubicin from the basolateral to the apical (b→a) and from the apical to the basolateral (a→b) side of the Caco-2 monolayers. Initial concentration of doxorubicin in the donor compartment was 3 μM, and the doxorubicin concentration in the receiver compartment was assayed by fluorescence (Fl, filled points) or HPLC (open points). Besides doxorubicin in the donor compartment, no further additive was applied in DMEM. The transport was characterized by linear fits ($R^2 > 0.98$ in all cases). The apparent permeability obtained by the fluorescence and HPLC assay in the b→a tests was $(2.81 \pm 0.03) \times 10^{-6}$ and $(2.75 \pm 0.03) \times 10^{-6}$ cm/s, respectively, while the $P_a$ values obtained in the a→b tests were $(6.07 \pm 0.04) \times 10^{-7}$ and $(5.79 \pm 0.04) \times 10^{-7}$ cm/s using fluorescence and HPLC assays, respectively. Typically, the transport experiments did not exceed 2.5 h in duration.

Excellent correlation was obtained between permeability values determined via fluorescence and HPLC assay (FIG. 14).

Transport Via Paracellular Route

The effect of microgel addition on paracellular permeability of the Caco-2 cell layers was estimated via permeability of mannitol, a neutral molecule, which is absorbed exclusively by passive diffusion through the paracellular route [42].

To attenuate the effect of PAA on the transepithelial transport, the experiments were conducted in calcium- and magnesium-free HBSS. Prior to the commencement of the transport experiments, the culture DMEM was replaced with an equal volume of HBSS and the cells were allowed to equilibrate for 1 h. Donor suspensions (2.5 mL total) containing 0.1 or 0.5 mg/mL microgels or Carbopol 934NF pre-equilibrated with $^{14}C$-mannitol in HBSS (initial specific activity of 0.2 μCi/mL) were used to replace the HBSS on the apical side, and the experiment commenced after 10 min of initial equilibration. Permeability experiments were conducted at pH 7.2, 37° C., 5% $CO_2$, and 90% relative humidity The TEER was measured following equilibration as described above for doxorubicin transport. TEER measurements were also performed during the experiment with 0.5 mg/mL polymer loading in order to check the effect of polymers on the opening, if any, of the tight intercellular junctions at time intervals of 0 (i.e. 10 min after adding the polymers), 30, 60, 90, 120, 150, 180, 210, and 240 min. The samples withdrawn prior to the 30-min time interval were not included in the $P_m$ calculation to ensure steady-state kinetics. The withdrawn samples of $^{14}C$-mannitol were mixed with 3 ml of MicroScint™ scintillation cocktail and the amount of radioactive marker transported at each time interval was determined using a TopCount NXT scintillation counter (PerkinElmer Life Sciences, Boston, Mass.). For negative control, no polymer was applied to the monolayers. Samples of 200 μL were withdrawn from the basolateral chamber at predetermined time intervals of 0, 5, 15, 30, 60, 90, 120, 180, 210, and 240 min and replaced with equal volumes of fresh HBSS. After completion of the transport studies, the polymers were removed carefully and monolayers were rinsed with HBSS and the culture medium (DMEM) was applied on the monolayers. The monolayers were allowed to regenerate for 2 days at 37° C. in an atmosphere of 95% air and 5% $CO_2$ at 90% relative humidity. TEER was monitored at 5, 6, 24, and 48 h during the recovery period. Control transport experiments were also conducted across Transwell™ filters without Caco-2 cells to determine the filter permeability ($P_{filter}$). The permeability of Caco-2 cell monolayers ($P_m$) was estimated by correcting the effective permeability ($P_{eff}$) for filter permeability ($P_{filter}$) according to the expression $P_{eff}^{-1} = P_m^{-1} + P_{filter}^{-1}$.

Flow Cytometry

Intracellular accumulation of doxorubicin in Caco-2 cells via P-gp-mediated efflux was studied by flow cytometry. Caco-2 cells ($3 \times 10^5/cm^2$) were seeded into 24-well plates and incubated for 3 weeks as described above. Cells were rinsed twice with phosphate-buffered saline (PBS) and pre-incubated for 30 min at 37° C. in 100 µg/mL PBS suspension of microgels, Carbopol 934NF, or Pluronic L61 or L92 (pH 7.4). At the end of the 30-min incubation period, doxorubicin was added to the culture medium to result in its concentration of 1 µg/mL. Following 3-h incubation at 37° C., the cells were washed twice with ice-cold PBS. Then the cells were rinsed with 1 mM EDTA and 0.25% trypsin solution, collected into centrifuge tubes and centrifuged at 1000×g for 15 min, and finally resuspended in cold PBS. An aliquot of cells was kept on ice for analysis of dye or drug uptake.

Samples were analyzed on a FACScan flow cytometer (Becton Dickinson Immunocytometry Systems, San Jose, Calif.) equipped with a Spectra Physics 15-mW argon laser ($\lambda_{ex}$=488 nm) and a red 585/42 band pass filter/FL2 fluorescence detector. All flow cytometric data were acquired and analyzed with the CellQuest software (Becton Dickinson). Scattering signals were measured, collected, and corrected for, in the linear scale mode. The logarithmically amplified fluorescence emission intensity was converted to a linear scale and expressed in arbitrary units relative to the control sample fluorescence intensity. The negative control was performed in drug-free medium to measure the cell auto-fluorescence. The control experiment was performed as described above, but with microgel-free PBS in the pre-incubation stage. At least $10^4$ cells were analyzed in each sample. Each experiment was repeated six times.

Colorimetric Cytotoxicity Assay 3-(4,5-Dimethylthiazol-2-yl)-2,5-diphenyltetrazolium bromide (MTT) assay comprises cleavage of the tetrazolium salt to a dark blue product (formazan) by mitochondrial dehydrogenases in living but not in dead cells [43]. Caco-2 cells used for MTT assay were seeded onto 96 well culture plates at seeding density of $5 \times 10^4$ cells per well in DMEM culture medium. The cells were cultured in an atmosphere of 95% air and 5% $CO_2$ at 37° C. and 90% humidity for 48 h. The culture medium was subsequently replaced with HBSS and microgel suspension was added to the wells to result in a 0.5 mg/mL effective polymer concentration in each well. As negative control no polymer was added to the wells, and as an internal reference, 0.5 mg/mL Carbopol in HBSS was applied to the cells. After adding the polymers, Caco-2 cells were further incubated at 37° C. for 4 h. The polymers were then removed, a 5 mg/ml MTT solution in PBS was added to each well and the cells were incubated for another 4 h at 37° C. The reaction product was then solubilized in dimethylsulfoxide before quantifying the color of the reaction product using an Emax precision microplate reader (Molecular Devices Co., Sunnyvale, Calif.) at 590 nm. In each MTT assay every microgel was tested in five replicates in microplate wells.

Statistical Analysis

All experiments were conducted at least in triplicate. The data were analyzed by Student's t-test at $\alpha$=0.05. A one-tailed t-test (Microsoft Excel®) ($P<0.01$) was used to identify significant differences between permeability results with additives and in the control experiments.

Example Results

The apparent permeabilities of the Caco-2 cell layers to doxorubicin obtained in the transport experiments are collected in Table 4 infra. As is seen, doxorubicin exhibited highly polarized transport, with the active efflux exceeding the passive influx 4.6-fold in the case when no additives were used. However, microgels and Pluronics (especially Pluronic L92), as well as their combinations lowered the active efflux of doxorubicin from Caco-2 cells as much as 2.4–3.2-fold. Pluronic L61 is known to be a potent doxorubicin efflux suppressor at concentrations up to CMC [37, 40]. At concentrations above CMC, the effects of Pluronics generally plateau and then decay [34,37,40]. Surface tension of 100 µg/mL suspensions of L92-PAA-EGDMA and F127-PAA-EGDMA microgels (XL=0.1 mol %) at 37° C. (deionized water, pH adjusted to 7.4) was measured to be 38.5 and 40.4 nm/m, respectively. That is, due to the numerous Pluronic chains exposed to the aqueous environment, the microgels exhibit surface activity comparable to the one of the hydrophobic Pluronic L61 or L92. Therefore, it can be hypothesized, with some certainty, that Pluronic-PAA copolymers, which are surface-active and solubilize lipids [14,17, 44], can affect the membrane proteins in a fashion analogous to Pluronics. Verapamil, a known non-selective inhibitor of the P-gp, showed most dramatic effect on $P_a^{b \rightarrow a}$ values (Table 4). Notably, this effect was not significantly neutralized by the presence of anionic microgels, indicating that the apparent ion exchange kinetics of the organic base (Verapamil) between microgels and the donor solutions were sufficiently rapid.

The passive influx of doxorubicin into Caco-2 cells was enhanced by all studied additives, with the microgels exhibiting the most pronounced effects (up to 2.5-fold increase in $P_a^{a \rightarrow b}$, Table 4). It has been shown that absorption enhancers such as surfactants can act by improving drug absorption via paracellular (primarily hydrophilic drugs) as well as transcellular (mostly lipophilic drugs) routes [45]. Combination of enhanced transcellular passive influx and suppressed P-gp-mediated active influx leads to a significant accumulation of doxorubicin in Caco-2 cells and in MDR cancer cells when Pluronics are applied at concentrations below their CMC [38,39]. No significant enhancement of the paracellular drug absorption by the "unimeric" Pluronics (i.e. in the absence of their micelles) have been reported [40, 46]. On the other hand, surfactants are generally known to enhance paracellular transport by opening the tight junctions through an increase in the membrane pore radius, widening of the intercellular space, contraction of calmodulin-dependent actin microfilaments, or contraction of the perijunctional actomyosin ring [47–49]. In addition, the high capacity of poly(acrylic acid) to bind $Ca^{2+}$ can deplete this ion from the extracellular cell medium and thus increase the paracellular permeability of the epithelial cell layers [50,51]. Indications exist that Pluronic-PAA can also bind $Ca^{2+}$ in biological milieu [52]. Therefore, it was important to address the question to what extent the dramatic increase in the net absorption by the Pluronic-PAA microgels (alone and in combination with Verapamil, Table 4) is due to the enhancement of the paracellular permeability and whether the microgels are toxic to the cells. The flow cytometry study that was carried out to estimate the effects of the microgels on the intracellular accumulation of doxorubicin after 3-h incubation, showed significant enhancement of the doxorubicin uptake. That is, the enhancement factor was measured to be 2.03±0.09 and 1.78±0.08 for the L92-PAA-EGDMA and F127-PAA-EGDMA microgels, respectively. In comparison, the enhancement factors for Carbopol, Pluronic L61, and L92 were measured to be 1.15±0.04, 1.52±0.08, and 1.92±0.09, respectively. Herein, we define the enhancement factor as the ratio of the integrated fluorescence intensity in the experiment with microgel to the intensity in the control experiment, both corrected for natural cell fluorescence. Thus the flow cytometry results demonstrated significant enhancement of the intracellular uptake by both microgels and Pluronics alone and hinted at the prevalence of the paracellular route.

TABLE 4

Effect of microgels, Pluronic L61, Pluronic L92, and Verapamil on doxorubicin transport[a] and absorption by Caco-2 cells.

| Treatment (Expt. No. in Table 1) | $P_a^{b \to a} \times 10^6$, cm/s | $P_a^{a \to b} \times 10^6$, cm/s | Net absorption (secretion)[b], % |
|---|---|---|---|
| Control (1) | 2.81 ± 0.03 | 0.61 ± 0.04 | (360) |
| Pluronic L61 (2) | 0.89 ± 0.04 | 1.12 ± 0.03 | −21 |
| Pluronic L92 (3) | 0.68 ± 0.04 | 1.17 ± 0.03 | −42 |
| L92-PAA-EGDMA (4) | 1.12 ± 0.03 | 1.55 ± 0.03 | −28 |
| L92-PAA-EGDMA + Pluronic L61 (5) | 0.95 ± 0.04 | 1.46 ± 0.03 | −35 |
| L92-PAA-EGDMA + Pluronic L92 (6) | 0.59 ± 0.04 | 1.26 ± 0.04 | −53 |
| F127-PAA-EGDMA (7) | 1.12 ± 0.04 | 1.32 ± 0.04 | −15 |
| F127-PAA-EGDMA + Pluronic L61 (8) | 1.16 ± 0.03 | 1.44 ± 0.04 | −19 |
| F127-PAA-EGDMA + Pluronic L92 (9) | 0.57 ± 0.03 | 1.23 ± 0.04 | −54 |
| Verapamil (10) | 0.45 ± 0.05 | 0.88 ± 0.04 | −49 |
| L92-PAA-EGDMA + verapamil (11) | 0.49 ± 0.05 | 1.39 ± 0.05 | −65 |
| F127-PAA-EGDMA + verapamil (12) | 0.54 ± 0.05 | 1.29 ± 0.05 | −58 |

[a]Apparent permeabilities with $P \leq 0.05$

Figure 15:
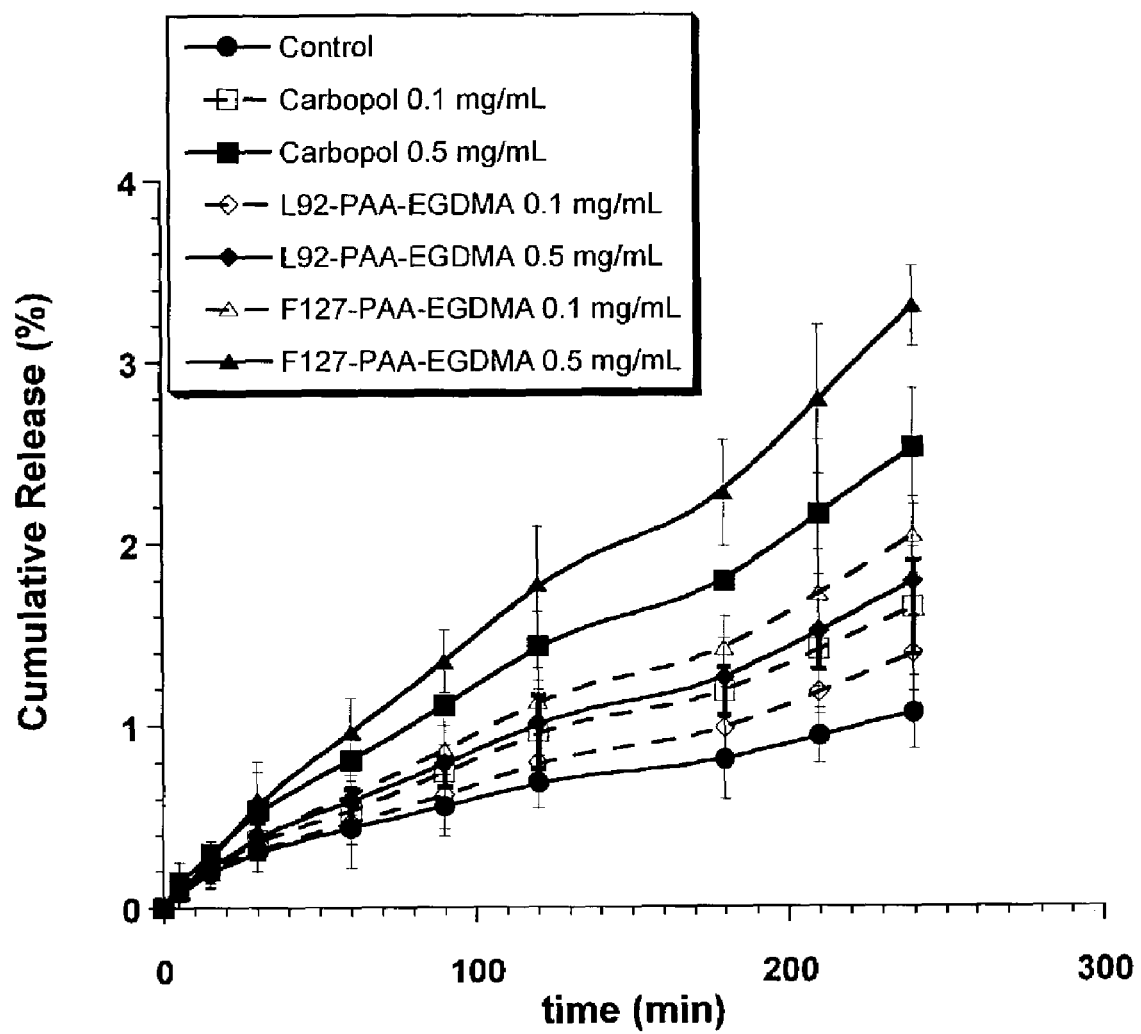
FIG. 15 shows cumulative transport of $^{14}C$-mannitol (MW 182.2 Da) across Caco-2 cell monolayers. Data are expressed as mean±S.D. of three to five experiments.

[b]Calculated using the formula: Net effect $= 100 \times \dfrac{P_a^{b \to a} - P_a^{a \to b}}{P_a^{a \to b}}$ Integrity of Caco-2 cell monolayers and opening of tight junctions can be assessed by measuring the flux of small hydrophilic radiolabeled molecules such as $^{14}C$-mannitol across the monolayers, as well as by TEER [53]. Transport of $^{14}C$-mannitol across Caco-2 monolayers was assessed in the presence of microgels as well as benign polymer widely used in oral applications (Carbopol 934NF), using HBSS as a negative control. As measured by radioactivity count, total cumulative transport of $^{14}C$-mannitol was relatively minor in all instances and did not exceed 3.5% of initial concentration in the donor compartment (FIG. 15).

Using the relative release kinetics, the effective permeability ($P_{eff}$) of monolayers was calculated as described in Experimental section (Table 5). As is seen, at concentrations of 0.1 mg/mL (as in Table 4) either Carbopol or microgels did not significantly enhance the $P_{eff}$. At concentrations of 0.5 mg/mL, the microgels and Carbopol significantly increased the $P_{eff}$ as compared to the negative control, but the differences between the microgels and Carbopol were insignificant. This is an important result indicating that although our microgels do result in the enhancement of the intracellular doxorubicin transport (Table 4), they do not provoke any dramatic changes in the paracellular permeability. The microgels compared favorably with Carbopol (lightly cross-linked poly(acrylic acid)), which is an industry standard in formulations that require adhesion to gastrointestinal tissues [54,55].

TABLE 5

Effective permeability ($P_{eff}$) of Caco-2 cell monolayers (mean ± S.D. of 3–4 experiments) for $^{14}C$-mannitol.

| Sample/Additive | Polymer concentration, mg/mL | $P_{eff} \Omega\ 10^7$, cm/s | Permeability ratio[a] |
|---|---|---|---|
| Control | 0 | 2.74 ± 0.44 | 1.0 |
| Carbopol | 0.1 | 3.36 ± 0.75 | 1.2 |
|  | 0.5 | 5.05 ± 1.45 | 1.8 |
| L92-PAA-EGDMA | 0.1 | 3.39 ± 0.92 | 1.2 |
|  | 0.5 | 3.89 ± 0.83 | 1.4 |
| F127-PAA-EGDMA | 0.1 | 4.43 ± 1.39 | 1.6 |
|  | 0.5 | 7.58 ± 1.26 | 2.8 |

[a]Relative to the Control experiment ($P \leq 0.05$).

Figure 16:
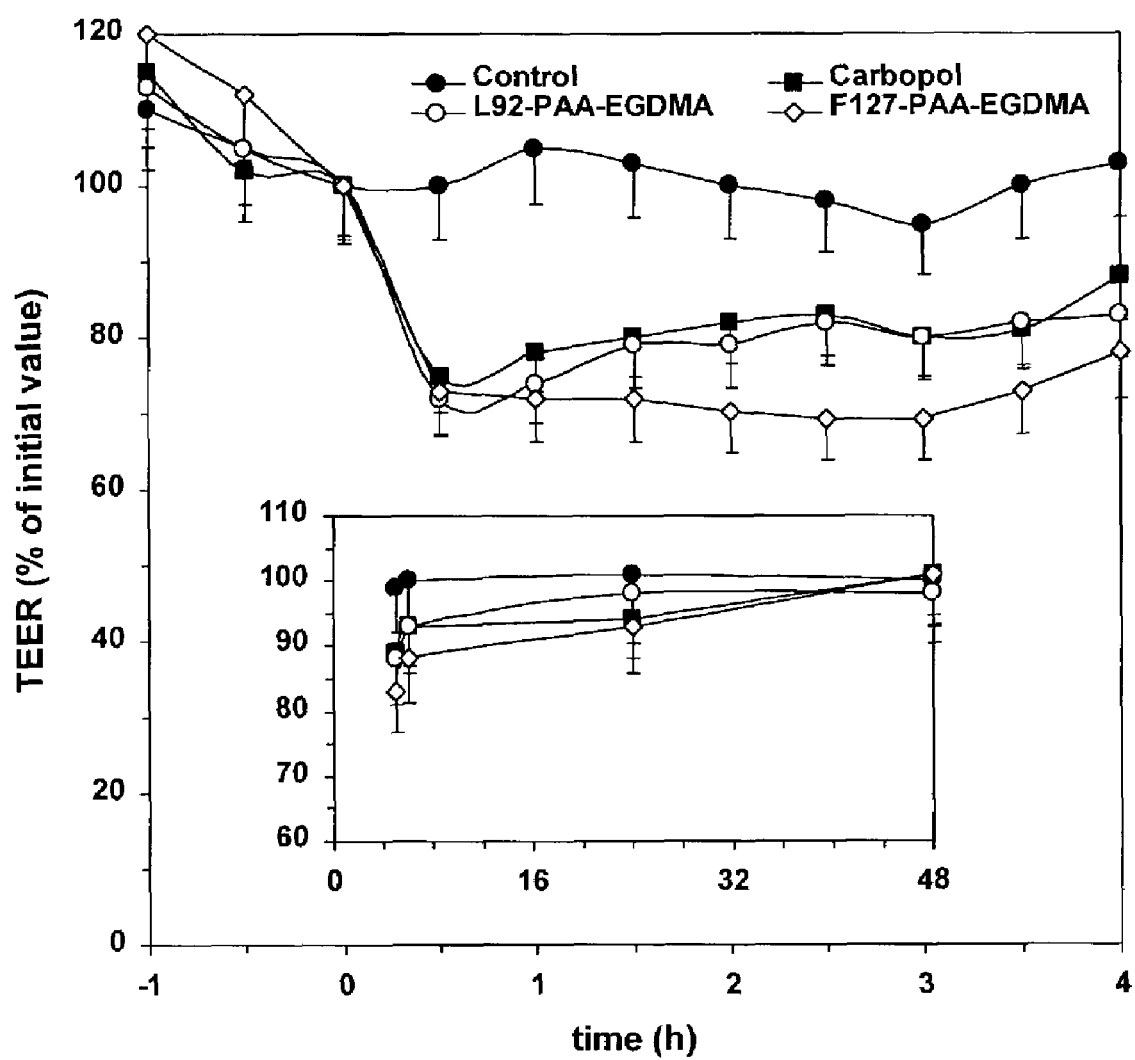
FIG. 16 shows the effect of polymers (0.5 mg/mL each) on TEER of Caco-2 cell monolayers. Inset shows TEER recovery of Caco-2 cell monolayers after removal of the polymers. Data are expressed as mean±S.D. of three to five experiments.

The observed tendency of added polymers (at 0.5 mg/mL level) to increase permeability of Caco-2 layers might be an indication that the polymers affect the integrity of cell membrane. Therefore, the reversibility of this effect is an important issue when screening these polymers as penetration enhancers. Herein, it was observed that after removing the polymers from the monolayers, TEER values completely recovered to initial values within 2 days, indicating that the effects, if any, of microgels on tight junctions are fully reversible (FIG. 16). It should be noted that at 0.1 mg/mL level, where microgels exhibited significant effects on the net absorption of doxorubicin (Table 4), the TEER was not significantly affected, which is an evidence that the transport across the Caco-2 monolayers in the presence of microgels is dominated by the transcellular, and not paracellular, pathway.

The MTT assay showed no toxic effects caused by mucosal application of the microgels in comparison with the negative control: 99±12, 97±11 and 97±15% of the cells were viable after application of microgels L92-PAA-EGDMA, F127-PAA-EGDMA, and Carbopol, respectively. Using the MTT assay, the polymer-treated cells were able to metabolize the mitochondrial substrate MTT by conversion into formazan crystals. This metabolic activity of cells is an appropriate technique for assessing the number of viable cells, since damaged or dead cells are devoid of any mitochondrial dehydrogenase activity [56]. Thus the Caco-2 cell monolayers appeared to be viable after 4 h application of microgels and no damage was observed at the intracellular level. Overall, the effect of microgels on mitochondrial dehydrogenase activity revealed their benign nature.

By inhibiting the P-gp-mediated doxorubicin efflux from the cells and enhancing the passive influx, the lightly cross-linked Pluronic-PAA microgels enhance the overall absorption of the drug by the cells. Notably, this effect is more pronounced that with a known penetration enhancer, Pluronic L61, and is comparable to the other relatively hydrophobic copolymer, Pluronic L92. Microgels exhibit synergism with Verapamil, a non-selective inhibitor of the P-gp. Judging by $^{14}$C-mannitol permeability, the microgels do not damage cells, so that no meaningful enhancement of the paracellular transport is observed. Any effect of microgels on trans-epithelial electrical resistance appears to be fully reversible. Notably, materials comprising slightly cross-linked poly(acrylic acid) have demonstrated no systemic absorption in gastrointestinal transit experiments both in vitro and in vivo [57,58].

Given the benign, non-irritating nature and mucoadhesive properties of the Pluronic-PAA microgels, for example, their application in the formulations for oral delivery of anticancer drugs is valuable indeed.

1. M. M. Malingre, J. H. Beijnen, J. H. Schellens, Oral delivery of taxanes. Invest New Drugs, 19(2) (2001) 155–162
2. M. Torres-Lugo, M. Garcia, R. Record, N. A. Peppas, pH-Sensitive hydrogels as gastrointestinal tract absorption enhancers: transport mechanisms of salmon calcitonin and other model molecules using the Caco-2 cell model, Biotechnol. Prog, 18(3) (2002) 612–616
3. C. Pontier, M. Viana, E. Champion, D. Bemache-Assollant, D. Chulia, HT29-MTX and Caco-2/TC7 monolayers as predictive models for human intestinal absorption: role of the mucus layer. J Pharm Sci,. 90(10) (2001)1608–1619
4. I. J. Hidalgo, Assessing the absorption of new pharmaceuticals. Curr. Top. Med. Chem., 1(5) (2001) 385–401
5. L. Bromberg, Novel family of thermogelling materials via C—C bonding between poly(acrylic acid) and poly(ethylene oxide)-b-poly(propylene oxide)-b-poly (ethylene oxide). J. Phys. Chem. B,. 102(11) (1998) 1956–1963
6. L. Bromberg, Properties of aqueous solutions and gels of ppoly(ethylene oxide)-b-poly(propylene oxide)-b-poly(ethylene oxide)-g-poly(acrylic acid). J. Phys. Chem. B.,. 102(52) (1998) 10736–10744
7. L. Bromberg, Polyether-modified poly(acrylic acid): synthesis and applications. Ind. Eng. Chem. Res., 37(11) (1998) 4267–4274
8. L. Bromberg, Synthesis and self-assembly of poly (ethylene oxide)-b-poly(propylene oxide)-b-poly(ethylene oxide)-g-poly(acrylic acid) gels. Ind. Eng. Chem. Res., 40(11) (2001) 2437–2444
9. L. Bromberg, M. Temchenko, T. A. Hatton, Dually responsive microgels from polyether-modified poly (acrylic acid): swelling and drug loading. Langmuir,. 18(22)(2002) 4944–4952
10. L. E. Bromberg, M. J. Orkisz, E. S. Ron, Bioadhesive properties of polyoxyethylene-b-polyoxypropylene-b-polyoxyethylene-g-poly(acrylic acid) polymers (Smart Hydrogel™), Polym. Prepr., 38(2)(1997), 626–627
11. L. E. Bromberg, E. S. Ron, Protein and peptide release from temperature-responsive gels and thermogelling polymer matrices, Adv. Drug Delivery Revs., 31(3) (1998) 197–221
12. L. E. Bromberg, Interactions between hydrophobically modified polyelectrolytes and mucin, Polym. Prepr., 40(2) (1999) 616–617
13. L. Bromberg, Enhanced nasal retention of hydrophobically modified polyelectrolytes, J. Pharm. Pharmacol., 53(1) (2001) 109–114
14. L. Bromberg, M. Temchenko, Loading of hydrophobic compounds into micellar solutions of hydrophobically modified polyelectrolytes, Langmuir, 15(25) (1999) 8627–8632
15. L. E. Bromberg, D. P. Barr, Aggregation phenomena in aqueous solutions of hydrophobically modified polyelectrolytes. A probe solubilization study, Macromolecules, 32(11) (1999) 3649–3657
16. L. Bromberg, Self-assembly in aqueous solutions of polyether-modified poly(acrylic acid), Langmuir, 14(20) (1998) 5806–5812
17. L. E. Bromberg, M. Temchenko, and R. H. Colby, Interactions among hydrophobically modified polyelectrolytes and surfactants of the same charge, Langmuir, 16 (6) (2000) 2609–2614
18. C. F. Higgins, R. Callaghan, K. J. Linton, M. F. Kosenberg, R. C. Ford, Structure of the multidrug resistance P-glycoprotein, Semin. Cancer Biol., 8 (1997)135–142
19. W. T. Bellamy, P-glycoproteins and multidrug resistance, Annu. Rev. Pharmacol. Toxicol., 36 (1996) 161–183
20. C. D. H. Tran, P. Timmins, B. R. Conway, W. J. Irwin, Investigation of the coordinated functional activities of cytochrome P450 3A4 and P-glycoprotein in limiting the absorption of xenobiotics in Caco-2 cells, J. Pharm. Sci., , 91 (2002)117–128
21. Y.-L. Lo, J. -D. Huang, Effects of sodium deoxycholate and sodium caprate on the transport of epirubicin in human intestinal epithelial Caco-2 cell layers and evented gut sacs of rats, Biochem. Pharmacol., 59 (2000) 665–672
22. N. F. Ho, P. S. Burton, R. A. Contradi, C. L. Barsuhn, A biophysical model of passive and polarized active transport processes in Caco-2 cells: approaches to uncoupling apical and basolateral membrane events in the intact cell, J. Pharm. Sci., 84 (1995) 21–27
23. J. Hunter, M. A. Jepson, T. Tsuruo, N. L. Simmons, B. H. Hirst, Functional expression of P-glycoprotein in apical membranes of human intestinal Caco-2 cells. Kinetics of vinblastine secretion and interaction with modulators, J. Biol. Chem., 268 (1993) 14991–14997
24. J. M. Ford, W. N. Hait, Pharmacology of drugs that alter multidrug resistance in cancer, Pharmacol. Rev., 42 (1990) 155–199

25. A. Sparreboom, J. van Asperen, U. Mayer, A. H. Schinkel, J. W. Smit, D. K. Meijer, P. Borst, W. J. Nooijen, J. H. Beijnen, O. van Tellingen, Limited oral bioavailability and active epithelial excretion of paclitaxel (Taxol) caused by P-glycoprotein in the intestine, Proc Natl Acad Sci U S A. 94(5) (1997) 2031–2035.

26. Y.-L. Lo, Phospholipids as multidrug resistance modulators of the transport of epirubicin in human intestinal epithelial Caco-2 cell layers and everted gut sacs of rats, Biochem. Pharmacol., 60 (2000) 1381–1390

27. I. C. J. van der Sandt, M. C. M. Blom-Roosemalen, A. G. de Boer, D. D. Breimer, Specificity of doxorubicin versus rhodamine-123 in assessing P-glycoprotein functionality in the LLC-PK1, LLC-PK1 :MDR1 and Caco-2 cell lines, European J. Pharm. Sci., 11 (2000) 207–214

28. T. Lindmark, Y. Kimura, P. Artursson, Absorption enhancement through intracellular regulation of tight junction permeability by medium chain fatty acids in Caco-2 cells, J. Pharmacol. Exp. Ther., 284 (1998) 362–369

29. P. K. Dudeja, K. M. Anderson, J. S. Harris, L. Buckingham, J. S. Coon, Reversal of multidrug resistance phenotype by surfactants: relationship to membrane lipid fluidity, Arch. Biochem. Biophys., 319 (1995) 309–315

30. R. Regev, Y. G. Assaraf, G. D. Eytan, Membrane fluidization by ether, other anesthetics, and certain agents abolishes P-glycoprotein ATPase activity and modulates efflux from multidrug-resistant cells, Eur. J. Biochem. 259 (1999) 18–24

31. S. V. Ambudkar, S. Dey, C. A. Hrycyna, M. Ramachandra, I. Pastan, M. M. Gottesman, Biochemical, cellular, and pharmacological aspects of the multidrug transporter, Annu. Rev. Pharmacol. Toxicol. 39 (1999) 361–398

32. M. M. Nerurkar, P. S. Burton, R. T. Borchardt, The use of surfactants to enhance the permeability of peptides through Caco-2 cells by inhibition of an apically polarized efflux system, Pharm. Res. 13 (1996) 528–534

33. M. M. Nerurkar, N. F. Ho, P. S. Burton, T. J. Vidmar, R. T. Borchardt, Mechanistic roles of neutral surfactants on concurrent polarized and passive membrane transport of a model peptide in Caco-2 cells, J. Pharm. Sci. 86 (1997) 813–821

34. E. V. Batrakova, S. Li, D. W. Miller, A. V. Kabanov, Pluronic P85 increases permeability of a broad Spectrum of drugs in polarized BBMEC and Caco-2 cell monolayers, Pharm. Res., 16(9)(1999) 1366–1372

35. E. V. Batrakova, S. Li, W. F. Elmquist, D. W. Miller, V. Yu. Alakhov, A. V. Kabanov, Mechanism of sensitization of MDR cancer cells by Pluronic block copolymers: Selective energy depletion, Br J Cancer., 85(12) (2001) 1987–1997

36. V. Alakhov, E. Klinski, P. Lemieux, G. Pietrzynski, A. Kabanov. Block copolymeric biotransport carriers as versatile vehicles for drug delivery, Expert Opin. Biol Ther., 1(4) (2001) 583–602

37. E. V. Batrakova, S. Li, S. V. Vinogradov, V. Yu. Alakhov, D. W. Miller D W, A. V. Kabanov, Mechanism of pluronic effect on P-glycoprotein efflux system in blood-brain barrier: contributions of energy depletion and membrane fluidization, J. Pharmacol. Exp. Ther., 299(2) (2001) 483–493

38. E. Batrakova, S. Lee, S. Li, A. Venne, V. Alakhov, A. Kabanov. Fundamental relationships between the composition of pluronic block copolymers and their hypersensitization effect in MDR cancer cells, Pharm Res. 16(9)(1999) 1373–1379

39. E. V. Batrakova, H. Y. Han, V. Yu. Alakhov, D. W. Miller, A. V. Kabanov. Effects of pluronic block copolymers on drug absorption in Caco-2 cell monolayers, Pharm Res., 15(6)(1998) 850–855

40. V. Alakhov, E. Klinski, S. Li., G. Pietrzynski, A. Venne, E. Batrakova, T. Bronitch, A. Kabanov, Block copolymer-based formulation of doxorubicin. From cell screen to clinical trials, Colloids Surf. B: Biointerfaces, 16 (1999) 113–134

41. M. Yu. Kozlov, N. S. Melik-Nubarov, E. V. Batrakova, A. V. Kabanov, Relationship between Pluronic block copolymer structure, critical micellization concentration and partitioning coefficients of low molecular mass solutes, Macromolecules, 33(9)(2000) 3305–3313

42. V. Pade, S. Stavchansky, Link between drug absorption solubility and permeability measurements in Caco-2 cells, Pharm. Res., 14 (1997) 1210–1215

43. T. J. Mossman, Rapid colorimetric assay for cellular growth and survival: application to proliferation and cytotoxicity assays. J. Immunol. Methods, 65 (1983) 55–63

44. L Bromberg, Biomedical applications of hydrophobically modified polyelectrolytes and polyelectrolyte block-copolymers. in: S. Tripathy, J. Kumar, H. S. Nalwa (Eds) Handbook of Polyelectrolytes and Their Applications. American Scientific Publishers, Stevenson Ranch, Calif., 2002, Vol. 1, Chapter 51.

45. M. Muranishi, Absorption enhancers, Crit. Rev. Ther. Drug Carrier Syst., 7 (1990) 1–33

46. E. V. Batrakova, H.-Y. Han, D. W. Miller, A. V. Kabanov Effects of Pluronic P85 Unimers and Micelles on Drug Permeability in Polarized BBMEC and Caco-2 Cells, Pharm. Res., 15(10)(1998) 1525–1532

47. M. Tomita, M. Hyashi, T. Horie, T. Ishizawa, S. Awazu, Enhancement of colonic drug absorption by the transcellular permeation route, Pharm. Res., 5 (1988) 786–789

48. M. Tomita, M. Hayashi, S. Awazu, Absorption-enhancing mechanism of sodium caprate and decanoyl-camitine in Caco-2 cells, J. Pharmacol. Exp. Ther., 272 (1995) 739–743

49. H. Takahashi, T. Shibasaki, K. Takeshita, F. Kaiho, M. Hayashi, The enhancing mechanism of capric acid (C10) from a suppository on rectal drug absorption through a paracellular pathway, Biol. Pharm. Bull., 20 (1997) 446–448

50. H. L. Lueβen, C.-M. Lehr, C.-O. Rentel, A. B. J. Noach, A. G. de Boer, J. C. Verhoef, H. E. Junginger, Bioadhesive polymers for the peroral delivery of peptide drugs, J.Control.Rel., 29 (1994) 329–338

51. H. L. Lueβen, C.-O. Rentel, A. F. Kotze, C. -M. Lehr, A. G. de Boer, J. C. Verhoef, H. E. Junginger, Mucoadhesive polymers in peroral peptide drug delivery. IV. Polycarbophil and chitosan are potent enhancers of peptide transport across intestinal mucosae in vitro, J. Control. Rel., 45 (1997) 15–23

52. L. Bromberg, Interactions among proteins and hydrophobically modified polyelectrolytes, J. Pharm. Pharmacol., 53 (2001) 541–547

53. P. Artursson. Epithelial transport of drugs in cell culture: a model for studying the passive diffusion of drugs over intestinal absorptive (Caco-2) cells, J. Pharm. Sci. 79 (1990) 476–482

54. A. K. Singla, M. Chawla, A. Singh. Potential applications of carbomer in oral mucoadhesive controlled drug delivery system: a review, Drug Dev. Ind. Pharm. 26(9) (2000) 913–924
55. L. I. Russo, E. S. Ghaly, Drug release from Carbomer 934 matrices, P. R. Health Sci. J., 19(2) (2000) 131–137
56. P. Liu, P. Davis, H. Liu, T. R. Krishnan, Evaluation of cytotoxicity and absorption enhancing effects of melittin-a novel absorption enhancer. Eur. J. Pharm. Biopharm. 48 (1999) 85–87
57. R. G. Riley, K. L. Green, J. D. Smart, J. Tsibouklis, J. A. Davis, F. Hampson, P. W. Dettmar, W. R. Wilber, The gastrointestinal transit profile of $^{14}$C-labelled poly (acrylic acids): an in vivo study, Biomaterials 22(13) (2001)1861–1867
58. R. G. Riley, J. D. Smart, J. Tsibouklis, S. A. Young, F. Hampson, A. Davis, G. Kelly, P. W. Dettmar, W. R. Wilber. An in vitro model for investigating the gastric mucosal retention of $^{14}$C-labelled poly(acrylic acid) dispersions, Int. J. Pharm. 236(1–2)(2002) 87–96

All publications and patents mentioned in this specification are herein incorporated by reference. Various modifications and variations of the described composition of matter, methods of manufacture and methods of useof the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in polymer chemistry and formulation are intended to be within the scope of the following claims.

What is claimed is:

1. A responsive microgel comprised of an ionizable network of covalently cross-linked homopolymeric ionizable monomers wherein the ionizable network is covalently attached to a single terminal region of an amphiphilic copolymer to form a plurality of 'dangling chains' and wherein the 'dangling chains' of amphiphilic copolymer form immobile intra-network aggregates in aqueous solution.

2. A responsive microgel according to claim 1 which responds volumetrically and reversibly to a change in one or more aqueous conditions selected from the group consisting of temperature, pH, and ionic conditions.

3. A responsive microgel according to claim 1 which is able to imbibe or solubilize a therapeutic entity.

4. A responsive microgel according to claim 1 which comprises at least one therapeutic entity.

5. A responsive microgel according to claim 4 which comprises a cationic therapeutic entity.

6. A responsive microgel according to claim 4 which comprises a hydrophobic therapeutic entity.

7. A responsive microgel according to claim 4 which comprises an amphiphilic therapeutic entity.

8. A responsive microgel according to claim 4 which delivers a substanially linear and sustained release of a hydrophobic or amphiphilic therapeutic entity under physiological conditions.

9. A responsive microgel according to claim 1 wherein the ionizable network of covalently cross-linked homopolymeric ionizable monomers is selected from the group consisting of poly(acrylic acid), poly(methcarylic acid), poly(4-vinylpyridinium alkyl halide), poly(sodium acrylate), poly (sodium methacrylate), sulfonated polyisoprene, and sulfonated polystyrene.

10. A responsive microgel according to claim 1 wherein the ionizable network of covalently cross-linked homopolymeric ionizable monomers is selected from the group consisting of poly(2-ethylacrylic acid), polyethyleneimine, and polyethylenepiperazine.

11. A responsive microgel according to claim 1 wherein an amphiphilic copolymer is comprised of a nonionic hydrophilic monomer and nonionic hydrophobic monomer.

12. A responsive microgel according to claim 11 wherein an amphiphilic copolymer is a diblock or triblock copolymer.

13. A responsive microgel according to claim 12 wherein an amphiphilic copolymer is comprised of (poly(ethylene oxide) and a monomer selected from the group consisting of poly(propylene oxide), poly(butylene oxide), polystyrene, polyisobutylene, poly(methyl methacrylate), and poly(tert-butyl acrylate).

14. A responsive microgel according to claim 13 wherein an amphiphilic copolymer is comprised of poly(ethylene oxide) and poly(propylene oxide).

15. A responsive microgel comprised of an ionizable network of covalently cross-linked homopolymeric ionizable monomers, wherein the ionizable network is poly (acrylic acid) or poly(methcarylic acid), covalently attached to a single terminal region of a poly(ethylene oxide) and poly(propylene oxide) amphiphilic copolymer, to form a plurality of 'dangling chains' covalently attached to the ionizable network and wherein the 'dangling chains' of the amphiphilic copolymer form immobile intra-network aggregates in aqueous solution.

* * * * *